(12) United States Patent
Spitzer et al.

(10) Patent No.: US 11,952,410 B2
(45) Date of Patent: Apr. 9, 2024

(54) MESOTHELIN-TARGETED TRAIL TRIMER

(71) Applicants: Dirk M. Spitzer, St. Louis, MO (US); William G. Hawkins, St. Louis, MO (US)

(72) Inventors: Dirk M. Spitzer, St. Louis, MO (US); William G. Hawkins, St. Louis, MO (US)

(73) Assignee: Washington University, St. Louis, MO (US)

( * ) Notice: Subject to any disclaimer, the term of this patent is extended or adjusted under 35 U.S.C. 154(b) by 714 days.

(21) Appl. No.: 16/610,433

(22) PCT Filed: May 2, 2018

(86) PCT No.: PCT/US2018/030700
§ 371 (c)(1),
(2) Date: Nov. 1, 2019

(87) PCT Pub. No.: WO2018/204520
PCT Pub. Date: Nov. 8, 2018

(65) Prior Publication Data
US 2021/0188945 A1    Jun. 24, 2021

Related U.S. Application Data

(60) Provisional application No. 62/527,598, filed on Jun. 30, 2017, provisional application No. 62/500,377, filed on May 2, 2017.

(51) Int. Cl.
| | | |
|---|---|---|
| *C07K 14/705* | (2006.01) | |
| *A61K 38/00* | (2006.01) | |
| *A61P 35/00* | (2006.01) | |
| *C07K 16/30* | (2006.01) | |

(52) U.S. Cl.
CPC ........ *C07K 14/70575* (2013.01); *A61P 35/00* (2018.01); *C07K 16/30* (2013.01); *A61K 38/00* (2013.01); *C07K 2317/567* (2013.01); *C07K 2317/622* (2013.01); *C07K 2317/76* (2013.01); *C07K 2319/30* (2013.01)

(58) Field of Classification Search
CPC ............. C07K 14/70575; C07K 16/30; C07K 2317/567; C07K 2317/622; C07K 2317/76; C07K 2319/30; C07K 2317/73; C07K 2319/00; A61P 35/00; A61K 38/00
See application file for complete search history.

(56) References Cited

U.S. PATENT DOCUMENTS

| | | | |
|---|---|---|---|
| 8,460,660 B2 | 6/2013 | Ho et al. | |
| 8,461,311 B2 * | 6/2013 | Hawkins | C07K 14/52 530/300 |
| 9,127,081 B2 * | 9/2015 | Spitzer | A61K 38/17 |
| 9,815,882 B2 * | 11/2017 | Spitzer | C12N 15/63 |
| 10,072,061 B2 * | 9/2018 | Spitzer | C12N 15/62 |
| 2008/0085539 A1 * | 4/2008 | Scholler | C07K 16/00 435/254.2 |
| 2012/0107933 A1 * | 5/2012 | Ho | C07K 16/30 435/375 |
| 2013/0302270 A1 * | 11/2013 | Spitzer | A61P 35/00 435/375 |

FOREIGN PATENT DOCUMENTS

| | | |
|---|---|---|
| WO | 2013063419 A2 | 5/2013 |
| WO | 2018204520 A1 | 11/2018 |

OTHER PUBLICATIONS

Paul, Fundamental Immunology, 3rd Edition, 1993, pp. 292-295, under the heading "Fv Structure and Diversity in Three Dimensions" (Year: 1993).*
Rudikoff et al. (Proc. Natl. Acad. Sci. USA, 79(6):1979-1983, Mar. 1982) (Year: 1982).*
Colman P. M. (Research in Immunology, 145:33-36, 1994) (Year: 1994).*
Bendig M. M. (Methods: A Companion to Methods in Enzymology, 1995; 8:83-93) (Year: 1995).*
Williams P, Chaudhry Y, Goodfellow IG, Billington J, Powell R, Spiller OB, Evans DJ, Lea S. Mapping CD55 function. The structure of two pathogen-binding domains at 1.7 A. J Biol Chem. Mar. 21, 2003;278(12):10691-6. (Year: 2003).*
Murphy et al. (Journal of Immunological Methods, vol. 463, p. 127-133, 2018) (Year: 2018).*
Chen (Sci Adv. Apr. 1, 2020;6(14):eaaz7825) (Year: 2020).*
Edwards et al. (Edwards et al. 2003. The remarkable flexibility of the human antibody repertoire; isolation of over one thousand different antibodies to a single protein, BlyS. Journal of Molecular Biology 334:103-118) (Year: 2003).*
Almagro, J. et al., "Humanization of antibodies," Front. Biosci., Jan. 1, 2008, pp. 1619-1633, vol. 13.
Bergan, L. et al., "Development and in vitro validation of anti-mesothelin biobodies that prevent CA125/Mesothelin-dependent cell attachment," Cancer Lett., 2007, pp. 263-274, vol. 255.
Chothia, C. et al., "Canonical Structures for the Hypervariable Regions of Immunoglobulins," J. Mol. Biol., 1987, pp. 901-917, vol. 196.
Chowdhury, P. et al., "Isolation of a high-affinity stable single-chain Fv specific for mesothelin from DNA-immunized mice by phage display and construction of a recombinant immunotoxin with antitumor activity," PNAS, Jan. 1998, pp. 669-674, vol. 95.

(Continued)

Primary Examiner — Jessica H Roark
Assistant Examiner — Francesca Edgingtongiordan
(74) Attorney, Agent, or Firm — Polsinelli PC

(57) ABSTRACT

The present disclosure provides constructs that comprise (a) a TNF-related apoptosis-inducing ligand (TRAIL) trimer comprising three consecutive extracellular TRAIL domains fused together in a head-to-tail configuration; (b) an epitope binding agent, and (c) optionally one or more additional components, wherein the epitope binding agent competitively inhibits binding of P4-TR3 or HN1-TR3 to cell surface human mesothelin. Constructs of the present disclosure induce apoptosis in cells expressing human mesothelin and a death receptor (DR4 or DR5) on the cell's surface.

4 Claims, 16 Drawing Sheets
Specification includes a Sequence Listing.

(56) References Cited

OTHER PUBLICATIONS

Clackson, T. et al., "Making antibody fragments using phage display libraries," Nature, Aug. 15, 1991, pp. 624-628, vol. 352.

Garg, G. et al., "Novel treatment option for MUC16-positive malignancies with the targeted TRAIL-based fusion protein Meso-TR3," BMC Cancer, 2014, pp. 1-12, vol. 14, No. 35.

Ho, M. et al., "A novel high-affinity human monoclonal antibody to mesothelin," Int. J. Cancer, 2011, pp. 2020-2030, vol. 128.

International Search Report and Written Opinion dated Jul. 26, 2018 from related Patent Application No. PCT/US2018/030700; 10 pgs.

Kuroki, L. et al., "Adenovirus platform enhances transduction efficiency in human mesenchymal stem cells: An opportunity for cellular carriers of targeted TRAIL-based TR3 biologics in ovarian cancer," PLoS One, 2017, pp. 1-20, vol. 12, No. 12, e0190125.

Maccallum, R. et al., "Antibody-antigen Interactions: Contact Analysis and Binding Site Topography," J. Mol. Biol., Oct. 1996, pp. 732-745, vol. 262, No. 5.

NCBI Reference Sequence NP_003833, "Tumor necrosis factor receptor superfamily member 10B isoform 1 precursor [*Homo sapiens*]," May 9, 2020; 5 pgs.

NCBI Reference Sequence NP_003835, "Tumor necrosis factor receptor superfamily member 10A [*Homo sapiens*]," May 9, 2020; 5 pgs.

NCBI Reference Sequence NP_671716, "Tumor necrosis factor receptor superfamily member 10B isoform 2 precursor [*Homo sapiens*]," Apr. 20, 2020; 5 pgs.

Portolano, S. et al., "Lack of promiscuity in autoantigen-specific H and L chain combinations as revealed by human H and L chain 'routlette'," J. Immunol., Feb. 1993, pp. 880-887, vol. 150, No. 3.

Siegemund, M. et al., "An optimized antibody-single-chain TRAIL fusion protein for cancer therapy," MABS, 2016, pp. 879-891, vol. 8, No. 5.

Spitzer, D. et al., "ScFv-mediated in vivo targeting of DAF to erythrocytes inhibits lysis by complement," Mol. Immunol., 2003, pp. 911-919, vol. 40, No. 13.

Spitzer, D. et al., "Properdin Can Initiate Complement Activation by Binding Specific Target Surfaces and Providing a Platform for De Novo Convertase Assembly," J. Immunol., 2007, pp. 2600-2608, vol. 179.

Spitzer, D. et al., "A Genetically Encoded Multifunctional TRAIL Trimer Facilitates Cell-Specific Targeting and Tumor Cell Killing," Mol. Cancer Ther., 2010, pp. 2142-2151, vol. 9, No. 7.

Su, Y. et al., "Mesothelin's minimal MUC16 binding moiety converts TR3 into a potent cancer therapeutic via hierarchical binding events at the plasma membrane," Oncotarget, 2016, pp. 31534-31549, vol. 7, No. 21.

Tatzel, K. et al., "Membrane-proximal TRAIL species are incapable of inducing short circuit apoptosis signaling: Implications for drug development and basic cytokine biology," Nat. Sci. Rep., 2016, pp. 1-12, vol. 6, No. 22661, with Erratum, 1 pg.

Urbanska, K. et al., "A Universal Strategy for Adoptive Immunotherapy of Cancer through Use of a Novel T-cell Antigen Receptor," Cancer Res., 2012, pp. 1844-1852, vol. 72, No. 7.

Xiang, X. et al., "HN125: A Novel Immunoadhesin Targeting MUC16 with Potential for Cancer Therapy," J. Cancer, 2011, pp. 280-291, vol. 2.

Zhang, Y-F. et al., "New High Affinity Monoclonal Antibodies Recognize Non-Overlapping Epitopes On Mesothelin For Monitoring And Treating Mesothelioma," Nat. Sci. Rep., 2015, pp. 1-14, vol. 5, No. 09928.

\* cited by examiner

MAMMEVQGGPSLGQTCVLIVIFTVLLQSLCVAVTYVYFTNELKQMQDKYS
KSGIACFLKEDDSYWDPNDEESMNSPCWQVKWQLRQLVRKMILRISEEI
STVQEKQQNISPLVRERGPQRVAAHITGTRGRSNTLSSPNSKNEKALGRK
INSWESSRSGHSFLSNLHLRNGELVIHEKGFYYIYSQTYFRFQEEIKENT
KNDKQMVQIIYKYTSYPDPILLMKSARNSCWSKDAEYGLYSIYQGGIFEL
KENDRIFVSVTNEHLIDMDHEASFFGAFLVG

FIG. 1

```
LPPRTPPMILPTSEETISTVQEKQQNISPLVRERGPQRVAAHITGTRGRSNTLSSPNSKNEKAL
GRKINSWESSRSGHSFLSNLHLRNGELVIHEKGFYYIYSQTYFRFQEEIKENTKNDKQMVQYIY
KYTSYPDPILLMKSARNSCWSKDAEYGLYSIYQGGIFELKENDRIFVSVTNEHLIDMDHEASFF
GAFLVGRSQNISPLVRERGPQRVAAHITGTRGRSNTLSSPNSKNEKALGRKINSWESSRSGHSF
LSNLHLRNGELVIHEKGFYYIYSQTYFRFQEEIKENTKNDKQMVQYIYKYTSYPDPILLMKSAR
NSCWSKDAEYGLYSIYQGGIFELKENDRIFVSVTNEHLIDMDHEASFFGAFLVGRSQNISPLVR
ERGPQRVAAHITGTRGRSNTLSSPNSKNEKALGRKINSWESSRSGHSFLSNLHLRNGELVIHEK
GFYYIYSQTYFRFQEEIKENTKNDKQMVQYIYKYTSYPDPILLMKSARNSCWSKDAEYGLYSIY
QGGIFELKENDRIFVSVTNEHLIDMDHEASFFGAFLVGRS
```

FIG. 2

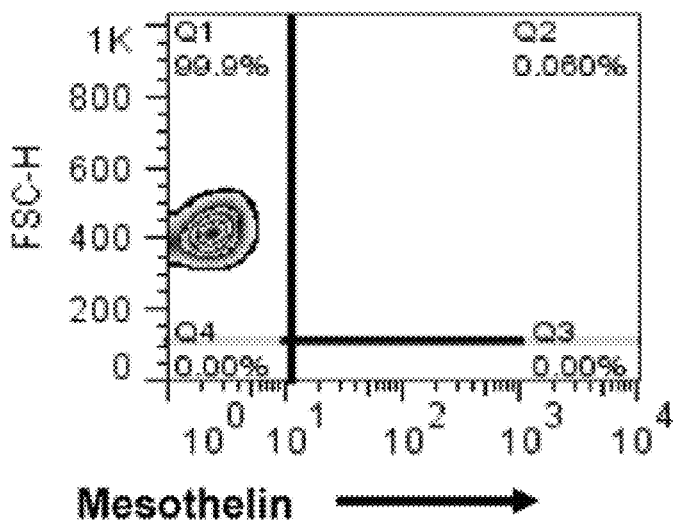
FIG. 10A
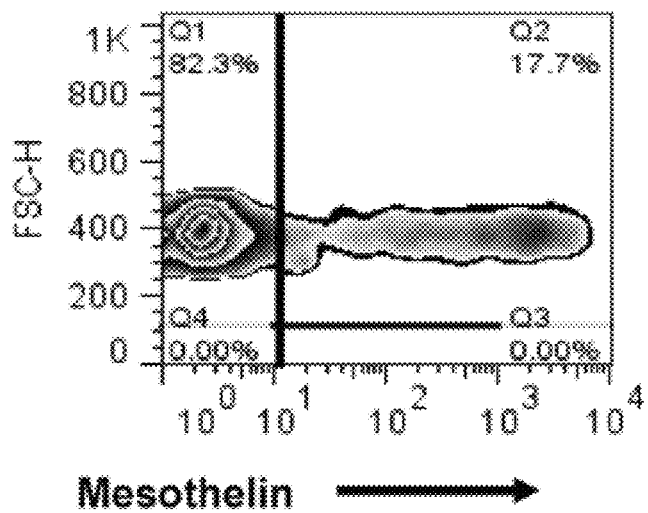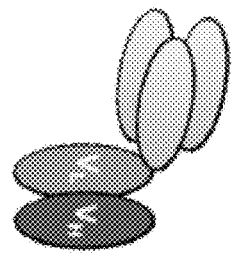
FIG. 10B
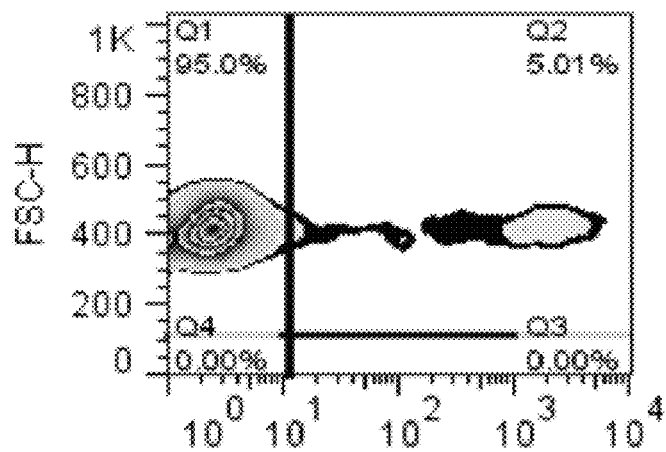
FIG. 10C

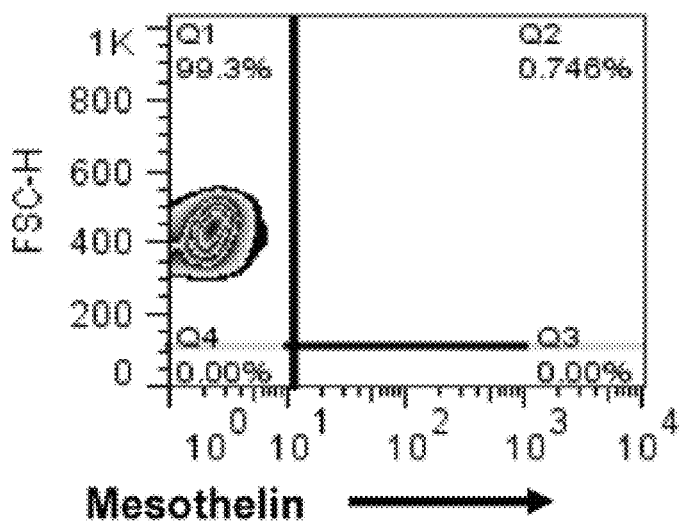
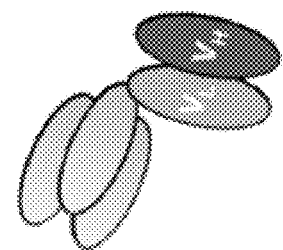
FIG. 10D
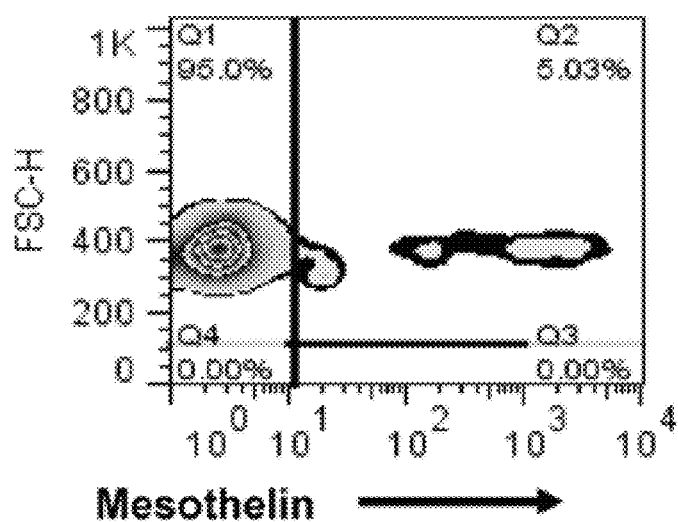
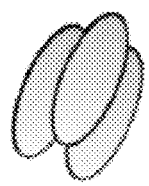
FIG. 10E
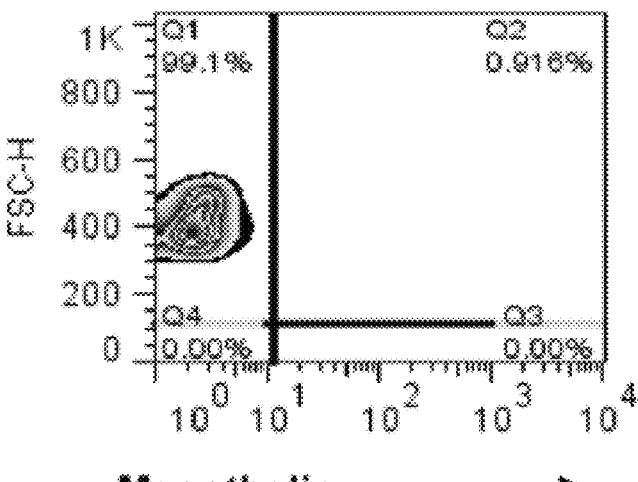
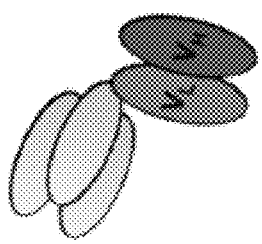
FIG. 10F

MESOTHELIN-TARGETED TRAIL TRIMER

CROSS REFERENCE TO RELATED APPLICATIONS

This application claims priority to PCT/US18/30700, filed May 2, 2018, which claims the benefit of U.S. provisional application No. 62/500,377, filed May 2, 2017, and U.S. provisional application No. 62/527,598, filed Jun. 30, 2017, each of which is hereby incorporated by reference in its entirety.

FIELD OF THE INVENTION

The present disclosure provides constructs that comprise (a) a TNF-related apoptosis-inducing ligand (TRAIL) trimer comprising three consecutive extracellular TRAIL domains fused together in a head-to-tail configuration; (b) an epitope binding agent, and (c) optionally one or more additional components, wherein the epitope binding agent competitively inhibits binding of P4-TR3 or HN1-TR3 to full-length, cell surface human mesothelin. Constructs of the present disclosure induce apoptosis in cells expressing full-length, human mesothelin and a death receptor (DR4 or DR5) on the cell's surface.

REFERENCE TO SEQUENCE LISTING

This application contains a Sequence Listing that has been submitted in ASCII format via EFS-Web and is hereby incorporated by reference in its entirety. The ASCII copy, created on May 1, 2018, is named 594973_SequenceListing_ST25.txt, and is 56 KB in size.

BACKGROUND OF THE INVENTION

Various forms of TNF-related apoptosis-inducing ligand (fusion protein format, in which the 3 extracellular domains of TRAIL are covalently linked. These fusion proteins have been successfully tethered to antibodies or antibody fragments to achieve specific targeting with the aim to enrich the therapeutic protein at the tumor site. For example, Tatzel et al. (*Scientific Reports* 2016, 6: 22661) described a mesothelin-targeted TR3 variant referred to as SS-TR3. However, it has been reported that cell death proceeded exclusively via a bystander mechanism and protected the mesothelin-positive targets from apoptosis rather than leading to their elimination. As such, there remains a need in the art for effective TRAIL-based therapies.

SUMMARY OF THE INVENTION

In an aspect, the present disclosure encompasses a construct comprising (a) a TNF-related apoptosis-inducing ligand (TRAIL) trimer comprising three extracellular TRAIL domains fused together in a head-to-tail configuration that substantially retains the killing capacity of TRAIL; (b) an epitope binding agent, wherein the epitope binding agent competitively inhibits binding of P4 or HN1 to cell surface human mesothelin; and (c) optionally a spacer. The epitope binding agent is an antibody that has a heavy chain variable region comprising SEQ ID NO: 13, SEQ ID NO: 14, and/or SEQ ID NO: 15; and/or a light chain variable region comprising SEQ ID NO: 10, SEQ ID NO: 11, and/or SEQ ID NO: 12; and the TRAIL trimer is a protein comprising a first peptide, a second peptide and third peptide; wherein each of the first peptide, the second peptide, and the third peptide is $TRAIL_{122-281}$ or a peptide that has an amino acid sequence that has at least 80% sequence identity to $TRAIL_{122-281}$, and the C-terminus of the first peptide is indirectly attached to N-terminus of the second peptide, and the C-terminus of the second peptide is indirectly attached to N-terminus of the third domain; and wherein the first peptide is attached to the second peptide by an amino acid linker, and the second peptide is attached to the third peptide by an amino acid linker.

In another aspect, the present disclosure encompasses a construct comprising (a) a TNF-related apoptosis-inducing ligand (TRAIL) trimer comprising three extracellular TRAIL domains fused together in a head-to-tail configuration that substantially retains the killing capacity of TRAIL; (b) an epitope binding agent, wherein the epitope binding agent competitively inhibits binding of P4 or HN1 to cell surface human mesothelin; and (c) optionally a spacer. The epitope binding agent is an antibody that a heavy chain variable region comprising SEQ ID NO: 20, SEQ ID NO: 21, and/or SEQ ID NO: 22; and/or a light chain variable region comprising SEQ ID NO: 18, the amino acid sequence KAS, and/or SEQ ID NO: 19; and the TRAIL trimer is a protein comprising a first peptide, a second peptide and third peptide; wherein each of the first peptide, the second peptide, and the third peptide is $TRAIL_{122-281}$ or a peptide that has an amino acid sequence that has at least 80% sequence identity to $TRAIL_{122-281}$, and the C-terminus of the first peptide is indirectly attached to N-terminus of the second peptide, and the C-terminus of the second peptide is indirectly attached to N-terminus of the third domain; and wherein the first peptide is attached to the second peptide by an amino acid linker, and the second peptide is attached to the third peptide by an amino acid linker.

Other aspects and iterations of the invention are described more thoroughly below.

BRIEF DESCRIPTION OF THE FIGURES

The application file contains at least one photograph executed in color. Copies of this patent application publication with color photographs will be provided by the Office upon request and payment of the necessary fee.

FIG. 1 shows the amino acid sequence of SEQ ID NO: 1, which is human TRAIL. The light grey shading identifies $TRAIL_{108-281}$. The combination of the dark grey shading and the light grey shading identifies $TRAIL_{91-281}$.

FIG. 2 shows the amino acid sequence of SEQ ID NO: 2, which is TR3. The TRAIL domains of TR3 are $TRAIL_{91-281}$, $TRAIL_{108-281}$, and $TRAIL_{108-281}$. The dark grey shading identifies $TRAIL_{91-281}$. The light grey shading identifies $TRAIL_{108-281}$. The N-terminal two seven amino acids are not critical for the killing capacity of the TRAIL trimer. In other embodiments of this disclosure, these two amino acids may be substituted with any other natural or non-natural amino acid, or deleted entirely. The two amino acids at the end of each TRAIL domain are also not critical. In other embodiments of this disclosure, these two amino acids may be substituted with any other natural or non-natural amino acid, or deleted entirely.

FIG. 10A-G shows the phenotypic characterization that reveals the differential cell death mechanisms between SS-TR3 and the humanized variants P4-TR3 and HN1-TR3. A mesothelin-expressing Jurkat-Meso cell pool (~5% mesothelin-positive cells) is treated with vehicle (FIG. 10C), TR3 (FIG. 10E), SS-TR3 (FIG. 10B), HN1-TR3 (FIG. 10D) and P4-TR3 (FIG. 10F) for several days before the mesothelin-expression cell ratio is determined by FACS analysis. SS-TR3 treatment leads to a significant accumulation of the cancer cells whereas P4-TR3 and HN1-TR3 treatment eliminates their cancer targets directly, while treatment with non-targeted TR3 alone does not change this ratio as expected. Representative schematics of TR3 variants are shown beside their corresponding panels. As a negative control, wild type Jurkat cells show absence of mesothelin expression (FIG. 10A). In comparison, the amount of mesothelin-positive cells is statistically higher in SS-TR3-treated Jurkat-Meso cells compared to cells treated with P4-TR3 and HN1-TR3 (FIG. 10G).

DETAILED DESCRIPTION

Figure 3:
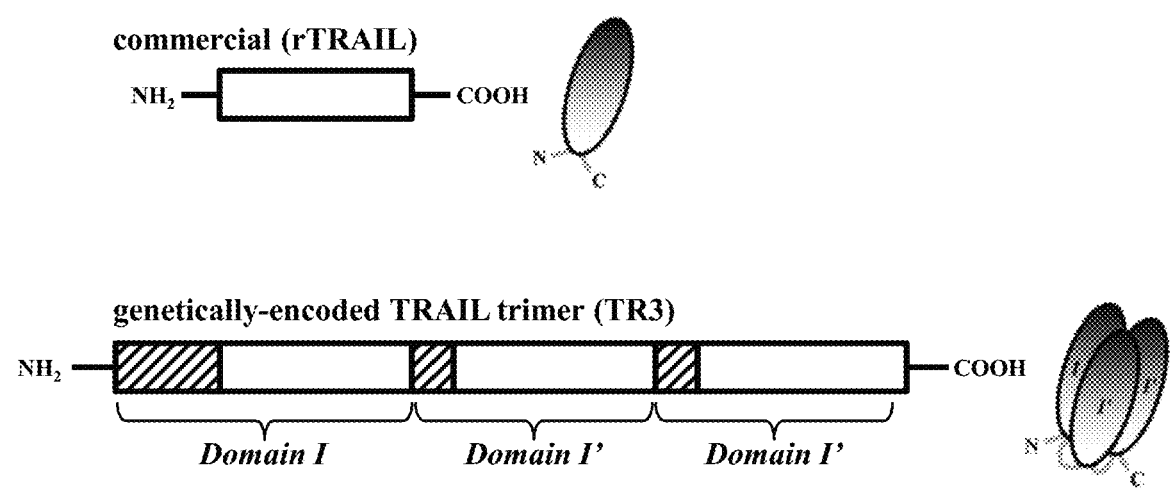
FIG. 3 shows a schematic representation of the TRAIL forms used in this study including a commercially available TRAIL (rTRAIL, aa 114-281) and TR3. A first TRAIL domain (domain I, aa 91-281) has been joined with two shorter TRAIL domain (domain I', aa 108-281) to result in TR3. The striped boxes represent the native TRAIL sequence used to connect the subunits where the sequence length is slightly smaller in domains I' (aa 108-113) compared to domain I (aa 91-113).

The present disclosure provides constructs that preferentially induce apoptosis in transformed and tumor cells. Constructs of the present disclosure comprise (a) a TNF-related apoptosis-inducing ligand (TRAIL) trimer comprising three consecutive extracellular TRAIL domains fused together in a head-to-tail configuration, (b) an epitope binding agent, and (c) optionally one or more additional components, wherein the epitope binding agent competitively inhibits binding of P4-TR3 or HN1-TR3 to cell surface human mesothelin. Advantageously, epitope binding agents disclosed herein target a TRAIL trimer to mesothelin-positive cells in a manner that results in death of the cell to which the construct is bound (i.e., a cis-acting phenotype), as well as bystander cell death (i.e., a trans-acting phenotype).

I. Constructs Comprising a Trail Trimer and an Epitope Binding Agent

The present disclosure provides a construct comprising a TNF-related apoptosis-inducing ligand (TRAIL) trimer and an epitope binding agent that competitively inhibits binding of scFv-P4 (SEQ ID NO: 6) or scFv-HN1 (SEQ ID NO: 7) to cell surface human mesothelin. The epitope binding agent is attached to the TRAIL trimer in manner that preserves the ability of the epitope binding agent to bind its cognate ligand and the killing capacity of the TRAIL trimer. In one embodiment, the epitope binding agent can be directly or indirectly attached to the C-terminus of the TRAIL trimer. In another embodiment, the epitope binding agent can be directly or indirectly attached to the N-terminus of the TRAIL trimer.

(a) TRAIL Trimer

The term "TRAIL trimer" refers to a polypeptide comprising three extracellular TRAIL domains arranged in a head-to-tail configuration that substantially retains the killing capacity of TRAIL.

Endogenous human TRAIL is initially synthesized as a Type-II transmembrane protein with its carboxyl (C)-terminus facing the extracellular milieu. It is subsequently cleaved at amino acid position V114 and is then released from the cell surface. The minimal human TRAIL domain, however, is amino acids 122-281 of human TRAIL. See, for example, Siegemund et al. *MABS* 2016, 8(5): 879-891, which is hereby incorporated by reference in its entirety. As used herein, the term "extracellular TRAIL domain" refers to a polypeptide comprising amino acids 122-281 of human TRAIL (i.e., $TRAIL_{122-281}$), or a polypeptide comprising an amino acid sequence that has at least 80% sequence identity to $TRAIL_{122-281}$ that substantially retains the killing capacity of $TRAIL_{122-281}$. The amino acid sequence of human TRAIL is SEQ ID NO: 1. A skilled artisan will be able to determine if an amino acid sequence has at least 80% sequence identity using methods well known in the art.

A TRAIL trimer of the present disclosure may be a homotrimer (i.e., each domain is the same) or a heterotrimer (i.e., at least two of the domains are unique). In some embodiments, each the extracellular TRAIL domain is independently selected from the group consisting of (a) $TRAIL_{114-281}$, (b) $TRAIL_{113-281}$, (c) $TRAIL_{112-281}$, (d) $TRAIL_{111-281}$, (e) $TRAIL_{110-281}$, (f) $TRAIL_{109-281}$, (g) $TRAIL_{108-281}$, (h) $TRAIL_{107-281}$, (i) $TRAIL_{106-281}$, (j) $TRAIL_{105-281}$, (k) $TRAIL_{104-281}$, (l) $TRAIL_{103-281}$, (m) $TRAIL_{102-281}$, (n) $TRAIL_{101-281}$, (o) $TRAIL_{100-281}$, (p) $TRAIL_{99-281}$, (q) $TRAIL_{98-281}$, (r) $TRAIL_{97-281}$, (s) $TRAIL_{96-281}$, (t) $TRAIL_{95-281}$, (u) $TRAIL_{94-281}$, (v) $TRAIL_{93-281}$, (w) $TRAIL_{92-281}$, (x) $TRAIL_{91-281}$, (y) $TRAIL_{115-281}$, (z) $TRAIL_{116-281}$, (aa) $TRAIL_{117-281}$, (bb) $TRAIL_{118-281}$, (cc) $TRAIL_{119-281}$, (dd) $TRAIL_{120-281}$, (ee) $TRAIL_{121-281}$, (ff) $TRAIL_{122-281}$, and (gg) an amino acid sequence that has at least 80% sequence identity to the peptide of (a) to (ff). In other embodiments, each the extracellular TRAIL domain is independently selected from the group consisting of (a) $TRAIL_{114-281}$, (b) $TRAIL_{108-281}$, (c) $TRAIL_{95-281}$, (d) $TRAIL_{91-281}$, (e) $TRAIL_{122-281}$, or (f) an amino acid sequence that has at least 80% sequence identity to the peptide of (a) to (e).

The term "head-to-tail configuration" means that each extracellular TRAIL domain is arranged N-terminally to C-terminally. Stated another way, a TRAIL trimer comprises a first extracellular TRAIL domain, a second extracellular TRAIL domain, and a third extracellular TRAIL domain, wherein the C-terminus of the first extracellular TRAIL domain is attached to N-terminus of the second extracellular TRAIL domain, and the C-terminus of the second extracellular TRAIL domain is attached to N-terminus of the third extracellular TRAIL domain. Each extracellular TRAIL domain may be directly or indirectly attached to the next. The type of linkage (i.e., direct or indirect) may depend, in part, upon the size of the extracellular TRAIL domain, as there needs to enough flexibility between each extracellular TRAIL domain to allow the domains to interact with each other.

When indirectly attached, one or more amino acids (natural or non-natural) may be between each domain. For example, 1, 2, 3, 4, or 5 amino acids (natural or non-natural) may be between each domain. In another example, 6, 7, 8, 9, or 10 amino acids (natural or non-natural) may be between each domain. In another example, 10 or more amino acids (natural or non-natural) may be between each domain. In certain embodiments, an amino acid linker may encode one or tags or cleavage sites (see below) that indirectly link the first and second extracellular TRAIL domain and/or the second and third extracellular TRAIL domain. Alternatively, or in addition, other peptide and non-peptide linkers may also be used to link one or more domains.

The term "substantially retains the killing capacity of TRAIL", as used herein, means a TRAIL trimer retains at least 80%, preferably at least 85%, more preferably at least 90%, even more preferably at least 95% of the killing capacity of TR3 (SEQ ID NO: 2) as assessed using a cell viability assay, for example as described in Su et al, *Oncotarget*, 2016; 7(21):31534-31549, which is incorporated herein by reference.

Based on the disclosure above, a skilled artisan will appreciate that a TRAIL timer may also be described as a fusion protein comprising a first peptide, a second peptide and third peptide; wherein each peptide comprises $TRAIL_{122-281}$ or a peptide that has an amino acid sequence that has at least 80% sequence identity to $TRAIL_{122-281}$, and the C-terminus of the first peptide is directly or indirectly attached to N-terminus of the second peptide, and the C-terminus of the second peptide is directly or indirectly attached to N-terminus of the third domain; and wherein the fusion protein substantially retains the killing capacity of TRAIL. In certain embodiments, the C-terminus of the first peptide is indirectly attached to N-terminus of the second peptide, and the C-terminus of the second peptide is indirectly attached to N-terminus of the third domain, and in each instance the peptides are attached by an amino acid linker that is 1 to 50 amino acids in length, 1 to 30 amino acids in length, 1 to 10 amino acids in length, or 1 to 5 amino acids in length.

In another embodiment, a TRAIL timer may be described as a fusion protein comprising a first peptide, a second peptide and third peptide; wherein each of the first peptide, the second peptide, and the third peptide is $TRAIL_{122-281}$ or a peptide that has an amino acid sequence that has at least 80% sequence identity to $TRAIL_{122-281}$, and the C-terminus of the first peptide is directly or indirectly attached to N-terminus of the second peptide, and the C-terminus of the second peptide is directly or indirectly attached to N-terminus of the third domain; and wherein the fusion protein substantially retains the killing capacity of TRAIL. In certain embodiments, the C-terminus of the first peptide is indirectly attached to N-terminus of the second peptide, and the C-terminus of the second peptide is indirectly attached to N-terminus of the third domain, and in each instance the peptides are attached by an amino acid linker that is 1 to 50 amino acids in length, 1 to 30 amino acids in length, 1 to 10 amino acids in length, or 1 to 5 amino acids in length.

In another embodiment, a TRAIL timer may also be described as a fusion protein comprising a first peptide, a second peptide and third peptide; wherein each peptide comprises $TRAIL_{114-281}$ or a peptide that has an amino acid sequence that has at least 80% sequence identity to TRAIL$_{114\text{-}281}$, and the C-terminus of the first peptide is directly or indirectly attached to N-terminus of the second peptide, and the C-terminus of the second peptide is directly or indirectly attached to N-terminus of the third domain; and wherein the fusion protein substantially retains the killing capacity of TRAIL. In certain embodiments, the C-terminus of the first peptide is indirectly attached to N-terminus of the second peptide, and the C-terminus of the second peptide is indirectly attached to N-terminus of the third domain, and in each instance the peptides are attached by an amino acid linker that is 1 to 50 amino acids in length, 1 to 30 amino acids in length, 1 to 10 amino acids in length, or 1 to 5 amino acids in length.

In another embodiment, a TRAIL timer may be described as a fusion protein comprising a first peptide, a second peptide and third peptide; wherein each of the first peptide, the second peptide, and the third peptide is TRAIL$_{114\text{-}281}$ or a peptide that has an amino acid sequence that has at least 80% sequence identity to TRAIL$_{114\text{-}281}$, and the C-terminus of the first peptide is directly or indirectly attached to N-terminus of the second peptide, and the C-terminus of the second peptide is directly or indirectly attached to N-terminus of the third domain; and wherein the fusion protein substantially retains the killing capacity of TRAIL. In certain embodiments, the C-terminus of the first peptide is indirectly attached to N-terminus of the second peptide, and the C-terminus of the second peptide is indirectly attached to N-terminus of the third domain, and in each instance the peptides are attached by an amino acid linker that is 1 to 50 amino acids in length, 1 to 30 amino acids in length, 1 to 10 amino acids in length, or 1 to 5 amino acids in length.

In another embodiment, a TRAIL timer may be described as a fusion protein comprising a first peptide, a second peptide and third peptide; wherein the first peptide, the second peptide and the third peptide each have an amino acid sequence comprising (a) TRAIL$_{91\text{-}281}$, (b) an amino acid sequence that has at least 80% sequence identity to TRAIL$_{91\text{-}281}$, (c) TRAIL$_{114\text{-}281}$, or (d) an amino acid sequence that has at least 80% sequence identity to TRAIL$_{114\text{-}281}$, and the C-terminus of the first peptide is directly or indirectly attached to N-terminus of the second peptide, and the C-terminus of the second peptide is directly or indirectly attached to N-terminus of the third domain; and wherein the fusion protein substantially retains the killing capacity of TRAIL. In certain embodiments, the C-terminus of the first peptide is indirectly attached to N-terminus of the second peptide, and the C-terminus of the second peptide is indirectly attached to N-terminus of the third domain, and in each instance the peptides are attached by an amino acid linker that is 1 to 50 amino acids in length, 1 to 30 amino acids in length, 1 to 10 amino acids in length, or 1 to 5 amino acids in length.

In another embodiment, a TRAIL timer may be described as a fusion protein comprising a first peptide, a second peptide and third peptide; wherein the first peptide comprises an amino acid sequence of TRAIL$_{91\text{-}281}$ or an amino acid sequence that has at least 80% sequence identity to TRAIL$_{91\text{-}281}$, the second peptide comprises TRAIL$_{114\text{-}281}$ or amino acid sequence that has at least 80% sequence identity to TRAIL$_{114\text{-}281}$, and third peptide comprises TRAIL$_{114\text{-}281}$ or an amino acid sequence that has at least 80% sequence identity to TRAIL$_{114\text{-}281}$, and the C-terminus of the first peptide is directly or indirectly attached to N-terminus of the second peptide, and the C-terminus of the second peptide is directly or indirectly attached to N-terminus of the third domain; and wherein the fusion protein substantially retains the killing capacity of TRAIL. In certain embodiments, the C-terminus of the first peptide is indirectly attached to N-terminus of the second peptide, and the C-terminus of the second peptide is indirectly attached to N-terminus of the third domain, and in each instance the peptides are attached by an amino acid linker that is 1 to 50 amino acids in length, 1 to 30 amino acids in length, 1 to 10 amino acids in length, or 1 to 5 amino acids in length.

In another embodiment, a TRAIL timer may also be described as a fusion protein comprising a first peptide, a second peptide and third peptide; wherein the first peptide is TRAIL$_{91\text{-}281}$ or a peptide that has an amino acid sequence that has at least 80% sequence identity to TRAIL$_{91\text{-}281}$, the second peptide is TRAIL$_{114\text{-}281}$ or a peptide that has an amino acid sequence that has at least 80% sequence identity to TRAIL$_{114\text{-}281}$, and the third peptide is TRAIL$_{114\text{-}281}$ or a peptide that has an amino acid sequence that has at least 80% sequence identity to TRAIL$_{114\text{-}281}$, and the C-terminus of the first peptide is directly or indirectly attached to N-terminus of the second peptide, and the C-terminus of the second peptide is directly or indirectly attached to N-terminus of the third domain; and wherein the fusion protein substantially retains the killing capacity of TRAIL. In certain embodiments, the C-terminus of the first peptide is indirectly attached to N-terminus of the second peptide, and the C-terminus of the second peptide is indirectly attached to N-terminus of the third domain, and in each instance the peptides are attached by an amino acid linker that is 1 to 50 amino acids in length, 1 to 30 amino acids in length, 1 to 10 amino acids in length, or 1 to 5 amino acids in length.

In another embodiment, a TRAIL timer may be described as a fusion protein comprising a first peptide, a second peptide and third peptide; wherein the first peptide comprises an amino acid sequence of TRAIL$_{91\text{-}281}$ or an amino acid sequence that has at least 80% sequence identity to TRAIL$_{91\text{-}281}$, the second peptide comprises TRAIL$_{108\text{-}281}$ or amino acid sequence that has at least 80% sequence identity to TRAIL$_{108\text{-}281}$, and third peptide comprises TRAIL$_{108\text{-}281}$ or an amino acid sequence that has at least 80% sequence identity to TRAIL$_{108\text{-}281}$, and the C-terminus of the first peptide is directly or indirectly attached to N-terminus of the second peptide, and the C-terminus of the second peptide is directly or indirectly attached to N-terminus of the third domain; and wherein the fusion protein substantially retains the killing capacity of TRAIL. In certain embodiments, the C-terminus of the first peptide is indirectly attached to N-terminus of the second peptide, and the C-terminus of the second peptide is indirectly attached to N-terminus of the third domain, and in each instance the peptides are attached by an amino acid linker that is 1 to 50 amino acids in length, 1 to 30 amino acids in length, or 1 to 5 amino acids in length 1 to 10 amino acids in length, or 1 to 5 amino acids in length.

In another embodiment, a TRAIL timer may be described as a fusion protein comprising a first peptide, a second peptide and third peptide; wherein the first peptide is TRAIL$_{91\text{-}281}$ or a peptide that has an amino acid sequence that has at least 80% sequence identity to TRAIL$_{91\text{-}281}$, the second peptide is TRAIL$_{109\text{-}281}$ or a peptide that has an amino acid sequence that has at least 80% sequence identity to TRAIL$_{108\text{-}281}$, and the third peptide is TRAIL$_{108\text{-}281}$ or a peptide that has an amino acid sequence that has at least 80% sequence identity to TRAIL$_{108\text{-}281}$, and the C-terminus of the first peptide is directly or indirectly attached to N-terminus of the second peptide, and the C-terminus of the second peptide is directly or indirectly attached to N-terminus of the third domain; and wherein the fusion protein substantially retains the killing capacity of TRAIL.

In an exemplary embodiment, a TRAIL trimer is TR3 (SEQ ID NO: 2). In another exemplary embodiment, a TRAIL trimer is a protein that (a) has at least 80% sequence identity to SEQ ID NO: 2, and (b) substantially retains the killing capacity of TRAIL. In another exemplary embodiment, a TRAIL trimer is a protein that (a) has at least 85% sequence identity to SEQ ID NO: 2, and (b) substantially retains the killing capacity of TRAIL. In another exemplary embodiment, a TRAIL trimer is a protein that (a) has at least 90% sequence identity to SEQ ID NO: 2, and (b) substantially retains the killing capacity of TRAIL. In another exemplary embodiment, a TRAIL trimer is a protein that (a) has at least 95% sequence identity to SEQ ID NO: 2, and (b) substantially retains the killing capacity of TRAIL.

(b) Epitope Binding Agent

The term "epitope-binding agent," as used herein, is used in the broadest sense and encompasses oligonucleic acids, polypeptides, and proteins that specifically bind to an antigen. The domain(s) of an epitope-binding agent that is involved in binding the antigen is referred to, herein, as a "variable region" or "variable domain". Non-limiting examples of epitope-binding agents include antibodies, antibody mimetics, and aptamers. In some embodiments, an epitope-binding agent is an antibody. In other embodiments, an epitope-binding agent is an antibody mimetic. In other embodiments, an epitope-binding agent is an aptamer.

Epitope-binding agents disclosed herein can be described or specified in terms of the epitope(s) that they recognize or bind. The portion of a target polypeptide that specifically interacts with the variable domain of an epitope-binding agent is an "epitope." The term "affinity" refers to a measure of the strength of the binding of an individual epitope with an epitope-binding agent's variable domain. Methods for determining affinity are known in the art.

Epitope binding agents of the present disclosure bind to cell surface human mesothelin with an affinity constant or affinity of interaction (KD) between about 0.1 pM to about 10 µM, preferably about 0.1 pM to about 1 µM, more preferably about 0.1 pM to about 100 nM. Human mesothelin can comprise any number of epitopes, depending on processing, conformational state, and location. Furthermore, it should be noted that an "epitope" on human mesothelin can be a linear epitope or a conformational epitope, and in both instances can include non-polypeptide elements, e.g., an epitope can include a carbohydrate or lipid side chain. As used herein, cell surface human mesothelin refers to a 40 kDa protein that is physiologically or recombinantly expressed and attached at the cell surface by a GPI anchor. The amino acid sequence of the 40 kDa protein, also referred to as membrane-bound, mature mesothelin, is provided in SEQ ID NO: 4. Non-limiting examples of suitable cell types include epithelial cells, mesothelial cells, and tumor cells. Non-limiting examples of suitable tumor cell types include mesothelioma cells, pancreatic tumor cells, ovarian tumor cells, stomach tumor cells, lung tumor cells and endometrial tumor cells. Additional non-limiting examples of tumor cells include tumor cells from a cancer selected from the group consisting of mesothelioma, papillary serous ovarian adenocarcinoma, clear cell ovarian carcinoma, mixed Mullerian ovarian carcinoma, endometroid mucinous ovarian carcinoma, pancreatic adenocarcinoma, ductal pancreatic adenocarcinoma, uterine serous carcinoma, lung adenocarcinoma, extrahepatic bile duct carcinoma, gastric adenocarcinoma, esophageal adenocarcinoma, colorectal adenocarcinoma and breast adenocarcinoma. Cell types that do not physiologically express mesothelin can also be used to recombinantly express human mesothelin. For example, the Examples detail recombinant expression of human mesothelin in Jurkat cells. Other cell line and cell types are also contemplated. In other embodiments, an epitope-binding agent of the present disclosure binds to an epitope on soluble mesothelin. As used herein, "soluble mesothelin" refers to fragment of mature mesothelin that results from cleavage of mesothelin from the cell's surface. Soluble mesothelin may be obtained from cell culture supernatant or soluble mesothelin in a body fluid sample, such as, for example, a blood, ascites, or serum sample. The epitope(s) to which epitope-binding agents of this disclosure bind may or may not be unique to cell surface human mesothelin.

An epitope binding agent of the present disclosure also competitively inhibits binding of the scFv-P4 (SEQ ID NO: 6) or the scFv-HN1 (SEQ ID NO: 7) to cell surface human mesothelin. As used herein, "scFv-P4" and "P4" are used interchangeably. Similarly, "scFv-HN1" and "HN1" are also used interchangeably. An epitope binding agent is said to competitively inhibit binding of scFv-P4 or scFv-HN1 to cell surface human mesothelin if the epitope binding agent binds to cell surface human mesothelin to the extent that it reduces binding of scFv-P4 or scFv-HN1 by at least 50%, at least 60%, at least 70%, at least 80%, or at least 90%. Competitive inhibition can be determined by any method known in the art, including but not limited to any antibody-antigen binding assay, for example, radioimmunoassay (RIA), ELISA, Western blot, immunoprecipitation, and competitive inhibition assays. A non-limiting example of a suitable assay is also described in Garg et al, *BMC Cancer.* 2014; 14:35.

An epitope-binding agent need not bind the exact same epitope as scFv-P4 to competitively inhibit binding of scFv-P4 to cell surface human mesothelin. Similarly, an epitope-binding agent need not bind the exact same epitope as scFv-HN1 to competitively inhibit binding of scFv-HN1 to cell surface human mesothelin. In some embodiments, an epitope-binding agent binds to the same epitope as scFv-P4 or to a cross-reactive epitope of scFv-P4. In other embodiments, an epitope-binding agent binds to the same epitope as scFv-HN1 or a cross-reactive epitope of scFv-HN1. A cross-reactive epitope generally contains many of the same complementary structural features as the inducing epitope, and in some cases, can actually fit better than the original. For example, certain antibodies have some degree of cross-reactivity, in that they bind related, but non-identical epitopes, e.g., epitopes with at least about 85%, at least about 90%, or at least about 95% identity (as calculated using methods known in the art) to a reference epitope.

In preferred embodiments, an epitope-binding agent is an antibody. The term "antibody," as used herein, is used in the broadest sense and encompasses various antibody and antibody-like structures, including but not limited to full-length monoclonal, polyclonal, and multispecific (e.g., bispecific, trispecific, etc.) antibodies, as well as heavy chain antibodies and antibody fragments provided they exhibit the desired antigen-binding activity. The domain(s) of an antibody that is involved in binding an antigen is referred to as a "variable region" or "variable domain," and is described in further detail below. A single variable domain may be sufficient to confer antigen-binding specificity. Preferably, but not necessarily, antibodies useful in the discovery are produced recombinantly. Antibodies may or may not be glycosylated, though glycosylated antibodies may be preferred. An "isolated" antibody is one which has been separated from a component of its natural environment. In some embodiments, an antibody is purified to greater than 95% or 99% purity as determined by methods known in the art.

In addition to antibodies described herein, it may be possible to design an antibody mimetic or an aptamer using methods known in the art that functions substantially the same as an antibody of the invention. An "antibody mimetic" refers to a polypeptide or a protein that can specifically bind to an antigen but is not structurally related to an antibody. Antibody mimetics have a mass of about 3 kDa to about 20 kDa. Non-limiting examples of antibody mimetics are affibody molecules, affilins, affimers, affitins, alphabodies, anticalins, avimers, knottins, DARPins, and monobodies. Aptamers interact with and bind to their targets through structural recognition, a process similar to that of an antigen-antibody reaction. Aptamers have a lower molecular weight than antibodies, typically about 8-25 kDa.

The terms "full length antibody" and "intact antibody" may be used interchangeably, and refer to an antibody having a structure substantially similar to a native antibody structure or having heavy chains that contain an Fc region as defined herein. The basic structural unit of a native antibody comprises a tetramer. Each tetramer is composed of two identical pairs of polypeptide chains, each pair having one "light" chain (about 25 kDa) and one "heavy" chain (about 50-70 kDa). Light chains are classified as gamma, mu, alpha, and lambda. Heavy chains are classified as gamma, mu, alpha, delta, or epsilon, and define the antibody's isotype as IgG, IgM, IgA, IgD and IgE, respectively. The amino-terminal portion of each light and heavy chain includes a variable region of about 100 to 110 or more amino acid sequences primarily responsible for antigen recognition (VL and VH, respectively). The carboxy-terminal portion of each chain defines a constant region primarily responsible for effector function. Within light and heavy chains, the variable and constant regions are joined by a "J" region of about 12 or more amino acid sequences, with the heavy chain also including a "D" region of about 10 more amino acid sequences. Intact antibodies are properly cross-linked via disulfide bonds, as is known in the art.

The variable domains of the heavy chain and light chain of an antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

"Framework region" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence: FR1-HVR1-FR2-HVR2-FR3-HVR3-FR4. The FR domains of a heavy chain and a light chain may differ, as is known in the art.

The term "hypervariable region" or "HVR" as used herein refers to each of the regions of a variable domain which are hypervariable in sequence (also commonly referred to as "complementarity determining regions" or "CDR") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). As used herein, "an HVR derived from a variable region" refers to an HVR that has no more than two amino acid substitutions, as compared to the corresponding HVR from the original variable region. Exemplary HVRs herein include: (a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987)); (b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991)); (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), as defined below for various antibodies of this disclosure. Unless otherwise indicated, HVR residues and other residues in the variable domain (e.g., FR residues) are numbered herein according to Kabat et al., supra.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

A "variant Fc region" comprises an amino acid sequence that can differ from that of a native Fc region by virtue of one or more amino acid substitution(s) and/or by virtue of a modified glycosylation pattern, as compared to a native Fc region or to the Fc region of a parent polypeptide. In an example, a variant Fc region can have from about one to about ten amino acid substitutions, or from about one to about five amino acid substitutions in a native sequence Fc region or in the Fc region of the parent polypeptide. The variant Fc region herein may possess at least about 80% homology, at least about 90% homology, or at least about 95% homology with a native sequence Fc region and/or with an Fc region of a parent polypeptide.

An "antibody fragment" refers to a molecule other than an intact antibody that comprises a portion of an intact antibody that binds the antigen to which the intact antibody binds. Non-limiting examples of antibody fragments include but are not limited to Fv, Fab, Fab', Fab'-SH, F(ab')$_2$; single-chain forms of antibodies and higher order variants thereof; single-domain antibodies, and multispecific antibodies formed from antibody fragments.

Single-chain forms of antibodies, and their higher order forms, may include, but are not limited to, single-domain antibodies, single chain variant fragments (scFvs), divalent scFvs (di-scFvs), trivalent scFvs (tri-scFvs), tetravalent scFvs (tetra-scFvs), diabodies, and triabodies and tetrabodies. ScFv's are comprised of heavy and light chain variable regions connected by a linker. In most instances, but not all, the linker may be a peptide. A linker peptide is preferably from about 5 to 30 amino acids in length, or from about 10 to 25 amino acids in length. Typically, the linker allows for stabilization of the variable domains without interfering with the proper folding and creation of an active binding site. In preferred embodiments, a linker peptide is rich in glycine, as well as serine or threonine. ScFvs can be used to facilitate phage display or can be used for flow cytometry, immunohistochemistry, or as targeting domains. Methods of making and using scFvs are known in the art. ScFvs may also be conjugated to a human constant domain (e.g. a heavy constant domain is derived from an IgG domain, such as IgG1, IgG2, IgG3, or IgG4, or a heavy chain constant domain derived from IgA, IgM, or IgE). Diabodies, triabodies, and tetrabodies and higher order variants are typically created by varying the length of the linker peptide from zero to several amino acids. Alternatively, it is also well known in the art that multivalent binding antibody variants can be generated using self-assembling units linked to the variable domain.

A "single-domain antibody" refers to an antibody fragment consisting of a single, monomeric variable antibody domain.

Multispecific antibodies include bi-specific antibodies, tri-specific, or antibodies of four or more specificities. Multispecific antibodies may be created by combining the heavy and light chains of one antibody with the heavy and light chains of one or more other antibodies. These chains can be covalently linked.

"Monoclonal antibody" refers to an antibody that is derived from a single copy or clone, including e.g., any eukaryotic, prokaryotic, or phage clone. "Monoclonal antibody" is not limited to antibodies produced through hybridoma technology. Monoclonal antibodies can be produced using hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

A "heavy chain antibody" refers to an antibody that consists of two heavy chains. A heavy chain antibody may be an IgG-like antibody from camels, llamas, alpacas, sharks, etc., or an IgNAR from a cartiliaginous fish.

A "humanized antibody" refers to a non-human antibody that has been modified to reduce the risk of the non-human antibody eliciting an immune response in humans following administration but retains similar binding specificity and affinity as the starting non-human antibody. A humanized antibody binds to the same or similar epitope as the non-human antibody. The term "humanized antibody" includes an antibody that is composed partially or fully of amino acid sequences derived from a human antibody germline by altering the sequence of an antibody having non-human hypervariable regions ("HVR"). The simplest such alteration may consist simply of substituting the constant region of a human antibody for the murine constant region, thus resulting in a human/murine chimera which may have sufficiently low immunogenicity to be acceptable for pharmaceutical use. Preferably, the variable region of the antibody is also humanized by techniques that are by now well known in the art. For example, the framework regions of a variable region can be substituted by the corresponding human framework regions, while retaining one, several, or all six non-human HVRs. Some framework residues can be substituted with corresponding residues from a non-human VL domain or VH domain (e.g., the non-human antibody from which the HVR residues are derived), e.g., to restore or improve specificity or affinity of the humanized antibody. Substantially human framework regions have at least about 75% homology with a known human framework sequence (i.e. at least about 75%, at least about 80%, at least about 85%, at least about 90%, at least about 95%, or at least about 99% sequence identity). HVRs may also be randomly mutated such that binding activity and affinity for the antigen is maintained or enhanced in the context of fully human germline framework regions or framework regions that are substantially human. As mentioned above, it is sufficient for use in the methods of this discovery to employ an antibody fragment. Further, as used herein, the term "humanized antibody" refers to an antibody comprising a substantially human framework region, at least one HVR from a nonhuman antibody, and in which any constant region present is substantially human. Substantially human constant regions have at least about 90% with a known human constant sequence (i.e. about 90%, about 95%, or about 99% sequence identity). Hence, all parts of a humanized antibody, except possibly the HVRs, are substantially identical to corresponding pairs of one or more germline human immunoglobulin sequences.

If desired, the design of humanized immunoglobulins may be carried out as follows, or using similar methods familiar to those with skill in the art (for example, see Almagro, et al. *Front. Biosci.* 2008, 13(5):1619-33). A murine antibody variable region is aligned to the most similar human germline sequences (e.g. by using BLAST or similar algorithm). The CDR residues from the murine antibody sequence are grafted into the similar human "acceptor" germline. Subsequently, one or more positions near the CDRs or within the framework (e.g., Vernier positions) may be reverted to the original murine amino acid in order to achieve a humanized antibody with similar binding affinity to the original murine antibody. Typically, several versions of humanized antibodies with different reversion mutations are generated and empirically tested for activity. The humanized antibody variant with properties most similar to the parent murine antibody and the fewest murine framework reversions is selected as the final humanized antibody candidate.

In an exemplary embodiment, an epitope binding agent of the present disclosure is an antibody that (a) competitively inhibits binding of scFv-P4, and (b) comprises a VL that has one or more HVRs derived from SEQ ID NO: 8 or a VH that has one or more HVRs derived from SEQ ID NO: 9. The HVR derived from SEQ ID NO: 8 may be L1, L2, L3, or any combination thereof. In certain embodiments, the VL may comprise an L1 of SEQ ID NO: 10, an L2 of SEQ ID NO: 11, an L3 of SEQ ID NO: 12, or any combination thereof (e.g. antibodies 1-7 in Table A). The HVR derived from SEQ ID NO: 9 may be H1, H2, H3, or any combination thereof. In certain embodiments, the VH may comprise an H1 of SEQ ID NO: 13, an H2 of SEQ ID NO: 14, an H3 of SEQ ID NO: 15, or any combination thereof (e.g. antibodies 8-14 in Table A). The antibody comprising one or more HVRs derived from SEQ ID NO: 9 may further comprise a light chain variable region (VL) comprising one or more HVRs derived from SEQ ID NO: 8. The HVR may be L1, L2, L3, or any combination thereof. In a preferred embodiment, the VL may comprise an L1 of SEQ ID NO: 10, an L2 of SEQ ID NO: 11, an L3 of SEQ ID NO: 12, or any combination thereof (e.g. antibodies 15-63 in Table A). In various embodiments above, the antibody may be a humanized antibody, or the antibody may have a VL with 90, 91, 92, 93, 94, 95, 96, 97, 98, 99, or 100% identity to SEQ ID NO: 8 and/or a VH with 90, 91, 92, 93, 94, 95, 96, 97, 98, 99 or 100% identity to SEQ ID NO: 9. In each of the above embodiments, the antibody may optionally comprise one or more constant regions, or a portion of a constant region, that is substantially human (i.e. at least 90%, 95%, or 99% sequence identity with a known human framework sequence). In each of the above embodiments, the antibody may be multivalent (e.g., recognize a second target in addition to mesothelin.) The present disclosure also encompasses the corresponding nucleic acid sequences of SEQ ID NO: 8, 9, 10, 11, 12, 13, 14, and 15, which can readily be determined by one of skill in the art, and may be incorporated into a vector or other large DNA molecule, such as a chromosome, in order to express an antibody of the disclosure.

In another exemplary embodiment, an epitope binding agent of the present disclosure is an antibody that (a) competitively inhibits binding of scFv-HN1, and (b) comprises a VL that has one or more HVRs derived from SEQ ID NO: 16 or a VH that has one or more HVRs derived from SEQ ID NO: 17. The HVR derived from SEQ ID NO: 16 may be L1, L2, L3, or any combination thereof. In certain embodiments, the VL may comprise an L1 of SEQ ID NO: 18, an L2 of the amino acid sequence KAS, an L3 of SEQ ID NO: 19, or any combination thereof (e.g. antibodies 64-70 in Table A). The HVR derived from SEQ ID NO: 17 may be H1, H2, H3, or any combination thereof. In certain embodiments, the VH may comprise an H1 of SEQ ID NO: 20, an H2 of SEQ ID NO: 21, an H3 of SEQ ID NO: 22, or any combination thereof (e.g. antibodies 71-77 in Table A). The antibody comprising one or more HVRs derived from SEQ ID NO: 17 may further comprise a light chain variable region (VL) comprising one or more HVRs derived from SEQ ID NO: 16. The HVR may be L1, L2, L3, or any combination thereof. In a preferred embodiment, the VL may comprise an L1 of SEQ ID NO: 18, an L2 of the amino acid sequence KAS, an L3 of SEQ ID NO: 19, or any combination thereof (e.g. antibodies 78-126 in Table A). In various embodiments above, the antibody may be a humanized antibody, or the antibody may have a VL with 90, 91, 92, 93, 94, 95, 96, 97, 98, 99, or 100% identity to SEQ ID NO: 16 and/or a VH with 90, 91, 92, 93, 94, 95, 96, 97, 98, 99 or 100% identity to SEQ ID NO: 17. In each of the above embodiments, the epitope binding agent may optionally comprise one or more constant regions, or a portion of a constant region, that is substantially human (i.e. at least 90%, 95%, or 99% sequence identity with a known human framework sequence). In each of the above embodiments, the antibody may be multivalent (e.g., recognize a second target in addition to mesothelin.) The present disclosure also encompasses the corresponding nucleic acid sequences of SEQ ID NO: 16, 17, 18, 19, 20, 21, 22, and 23, which can readily be determined by one of skill in the art, and may be incorporated into a vector or other large DNA molecule, such as a chromosome, in order to express an antibody of the disclosure.

In another exemplary embodiment, an epitope binding agent of the present disclosure is the scFv-P4 (SEQ ID NO: 6). In another exemplary embodiment, an epitope binding agent of the present disclosure is a polypeptide that (a) has at least 80% sequence identity to SEQ ID NO: 6, and (b) competitively inhibits binding of scFv-P4. In another exemplary embodiment, an epitope binding agent of the present disclosure is a polypeptide that (a) has at least 85% sequence identity to SEQ ID NO: 6, and (b) competitively inhibits binding of scFv-P4. In another exemplary embodiment, an epitope binding agent of the present disclosure is a polypeptide that (a) has at least 90% sequence identity to SEQ ID NO: 6, and (b) competitively inhibits binding of scFv-P4. In another exemplary embodiment, an epitope binding agent of the present disclosure is a polypeptide that (a) has at least 95% sequence identity to SEQ ID NO: 6, and (b) competitively inhibits binding of scFv-P4.

In another exemplary embodiment, an epitope binding agent of the present disclosure is the scFv-HN1 (SEQ ID NO: 7). In another exemplary embodiment, an epitope binding agent of the present disclosure is a polypeptide that (a) has at least 80% sequence identity to SEQ ID NO: 7, and (b) competitively inhibits binding of scFv-HN1. In another exemplary embodiment, an epitope binding agent of the present disclosure is a polypeptide that (a) has at least 85% sequence identity to SEQ ID NO: 7, and (b) competitively inhibits binding of scFv-HN1. In another exemplary embodiment, an epitope binding agent of the present disclosure is a polypeptide that (a) has at least 90% sequence identity to SEQ ID NO: 7, and (b) competitively inhibits binding of scFv-HN1. In another exemplary embodiment, an epitope binding agent of the present disclosure is a polypeptide that (a) has at least 95% sequence identity to SEQ ID NO: 7, and (b) competitively inhibits binding of scFv-HN1.

TABLE A

Exemplary Antibodies

| Antibody | Light Chain HVR | | | Heavy Chain HVR | | |
|---|---|---|---|---|---|---|
| | L1 | L2 | L3 | H1 | H2 | H3 |
| 1 | SEQ ID NO: 10 | | | | | |
| 2 | SEQ ID NO: 10 | SEQ ID NO: 11 | | | | |
| 3 | SEQ ID NO: 10 | SEQ ID NO: 11 | SEQ ID NO: 12 | | | |
| 4 | | SEQ ID NO: 11 | | | | |
| 5 | | SEQ ID NO: 11 | SEQ ID NO: 12 | | | |
| 6 | | | SEQ ID NO: 12 | | | |
| 7 | SEQ ID NO: 10 | | SEQ ID NO: 12 | | | |
| 8 | | | | SEQ ID NO: 13 | | |
| 9 | | | | SEQ ID NO: 13 | SEQ ID NO: 14 | |
| 10 | | | | SEQ ID NO: 13 | SEQ ID NO: 14 | SEQ ID NO: 15 |
| 11 | | | | | SEQ ID NO: 14 | |
| 12 | | | | | SEQ ID NO: 14 | SEQ ID NO: 15 |
| 13 | | | | | | SEQ ID NO: 15 |
| 14 | | | | SEQ ID NO: 13 | | SEQ ID NO: 15 |
| 15 | SEQ ID NO: 10 | | | SEQ ID NO: 13 | | |
| 16 | SEQ ID NO: 10 | | | SEQ ID NO: 13 | SEQ ID NO: 14 | |
| 17 | SEQ ID NO: 10 | | | SEQ ID NO: 13 | SEQ ID NO: 14 | SEQ ID NO: 15 |
| 18 | SEQ ID NO: 10 | | | | SEQ ID NO: 14 | |

TABLE A-continued

Exemplary Antibodies

| | Light Chain HVR | | | Heavy Chain HVR | | |
|---|---|---|---|---|---|---|
| Antibody | L1 | L2 | L3 | H1 | H2 | H3 |
| 19 | SEQ ID NO: 10 | | | | SEQ ID NO: 14 | SEQ ID NO: 15 |
| 20 | SEQ ID NO: 10 | | | | | SEQ ID NO: 15 |
| 21 | SEQ ID NO: 10 | | | SEQ ID NO: 13 | | SEQ ID NO: 15 |
| 22 | SEQ ID NO: 10 | SEQ ID NO: 11 | | SEQ ID NO: 13 | | |
| 23 | SEQ ID NO: 10 | SEQ ID NO: 11 | | SEQ ID NO: 13 | SEQ ID NO: 14 | |
| 24 | SEQ ID NO: 10 | SEQ ID NO: 11 | | SEQ ID NO: 13 | SEQ ID NO: 14 | SEQ ID NO: 15 |
| 25 | SEQ ID NO: 10 | SEQ ID NO: 11 | | | SEQ ID NO: 14 | |
| 26 | SEQ ID NO: 10 | SEQ ID NO: 11 | | | SEQ ID NO: 14 | SEQ ID NO: 15 |
| 27 | SEQ ID NO: 10 | SEQ ID NO: 11 | | | | SEQ ID NO: 15 |
| 28 | SEQ ID NO: 10 | SEQ ID NO: 11 | | SEQ ID NO: 13 | | SEQ ID NO: 15 |
| 29 | SEQ ID NO: 10 | SEQ ID NO: 11 | SEQ ID NO: 12 | SEQ ID NO: 13 | | |
| 30 | SEQ ID NO: 10 | SEQ ID NO: 11 | SEQ ID NO: 12 | SEQ ID NO: 13 | SEQ ID NO: 14 | |
| 31 | SEQ ID NO: 10 | SEQ ID NO: 11 | SEQ ID NO: 12 | SEQ ID NO: 13 | SEQ ID NO: 14 | SEQ ID NO: 15 |
| 32 | SEQ ID NO: 10 | SEQ ID NO: 11 | SEQ ID NO: 12 | | SEQ ID NO: 14 | |
| 33 | SEQ ID NO: 10 | SEQ ID NO: 11 | SEQ ID NO: 12 | | SEQ ID NO: 14 | SEQ ID NO: 15 |
| 34 | SEQ ID NO: 10 | SEQ ID NO: 11 | SEQ ID NO: 12 | SEQ ID NO: 13 | | SEQ ID NO: 15 |
| 35 | SEQ ID NO: 10 | SEQ ID NO: 11 | SEQ ID NO: 12 | | | SEQ ID NO: 15 |
| 36 | | SEQ ID NO: 11 | | SEQ ID NO: 13 | | |
| 37 | | SEQ ID NO: 11 | | SEQ ID NO: 13 | SEQ ID NO: 14 | |
| 38 | | SEQ ID NO: 11 | | SEQ ID NO: 13 | SEQ ID NO: 14 | SEQ ID NO: 15 |
| 39 | | SEQ ID NO: 11 | | | SEQ ID NO: 14 | |
| 40 | | SEQ ID NO: 11 | | | SEQ ID NO: 14 | SEQ ID NO: 15 |
| 41 | | SEQ ID NO: 11 | | | | SEQ ID NO: 15 |
| 42 | | SEQ ID NO: 11 | | SEQ ID NO: 13 | | SEQ ID NO: 15 |
| 43 | | SEQ ID NO: 11 | SEQ ID NO: 12 | SEQ ID NO: 13 | | |
| 44 | | SEQ ID NO: 11 | SEQ ID NO: 12 | SEQ ID NO: 13 | SEQ ID NO: 14 | |
| 45 | | SEQ ID NO: 11 | SEQ ID NO: 12 | SEQ ID NO: 13 | SEQ ID NO: 14 | SEQ ID NO: 15 |
| 46 | | SEQ ID NO: 11 | SEQ ID NO: 12 | | SEQ ID NO: 14 | |
| 47 | | SEQ ID NO: 11 | SEQ ID NO: 12 | | SEQ ID NO: 14 | SEQ ID NO: 15 |
| 48 | | SEQ ID NO: 11 | SEQ ID NO: 12 | | | SEQ ID NO: 15 |
| 49 | | SEQ ID NO: 11 | SEQ ID NO: 12 | SEQ ID NO: 13 | | SEQ ID NO: 15 |
| 50 | | | SEQ ID NO: 12 | SEQ ID NO: 13 | | |
| 51 | | | SEQ ID NO: 12 | SEQ ID NO: 13 | SEQ ID NO: 14 | |
| 52 | | | SEQ ID NO: 12 | SEQ ID NO: 13 | SEQ ID NO: 14 | SEQ ID NO: 15 |
| 53 | | | SEQ ID NO: 12 | | SEQ ID NO: 14 | |
| 54 | | | SEQ ID NO: 12 | | SEQ ID NO: 14 | SEQ ID NO: 15 |
| 55 | | | SEQ ID NO: 12 | | | SEQ ID NO: 15 |
| 56 | | | SEQ ID NO: 12 | SEQ ID NO: 13 | | SEQ ID NO: 15 |
| 57 | SEQ ID NO: 10 | | SEQ ID NO: 12 | SEQ ID NO: 13 | | |
| 58 | SEQ ID NO: 10 | | SEQ ID NO: 12 | SEQ ID NO: 13 | SEQ ID NO: 14 | |
| 59 | SEQ ID NO: 10 | | SEQ ID NO: 12 | SEQ ID NO: 13 | SEQ ID NO: 14 | SEQ ID NO: 15 |
| 60 | SEQ ID NO: 10 | | SEQ ID NO: 12 | | SEQ ID NO: 14 | |
| 61 | SEQ ID NO: 10 | | SEQ ID NO: 12 | | SEQ ID NO: 14 | SEQ ID NO: 15 |
| 62 | SEQ ID NO: 10 | | SEQ ID NO: 12 | | | SEQ ID NO: 15 |
| 63 | SEQ ID NO: 10 | | SEQ ID NO: 12 | SEQ ID NO: 13 | | SEQ ID NO: 15 |
| 64 | SEQ ID NO: 18 | | | | | |
| 65 | SEQ ID NO: 18 | KAS | | | | |
| 66 | SEQ ID NO: 18 | KAS | SEQ ID NO: 19 | | | |
| 67 | | KAS | | | | |
| 68 | | KAS | SEQ ID NO: 19 | | | |
| 69 | | | SEQ ID NO: 19 | | | |
| 70 | SEQ ID NO: 18 | | SEQ ID NO: 19 | | | |
| 71 | | | | SEQ ID NO: 102 | | |
| 72 | | | | SEQ ID NO: 102 | SEQ ID NO: 21 | |
| 73 | | | | SEQ ID NO: 102 | SEQ ID NO: 21 | SEQ ID NO: 22 |
| 74 | | | | | SEQ ID NO: 21 | |
| 75 | | | | | SEQ ID NO: 21 | SEQ ID NO: 22 |
| 76 | | | | | | SEQ ID NO: 22 |
| 77 | | | | SEQ ID NO: 20 | | SEQ ID NO: 22 |
| 78 | SEQ ID NO: 18 | | | SEQ ID NO: 20 | | |
| 79 | SEQ ID NO: 18 | | | SEQ ID NO: 20 | SEQ ID NO: 21 | |
| 80 | SEQ ID NO: 18 | | | SEQ ID NO: 20 | SEQ ID NO: 21 | SEQ ID NO: 22 |
| 81 | SEQ ID NO: 18 | | | | SEQ ID NO: 21 | |
| 82 | SEQ ID NO: 18 | | | | SEQ ID NO: 21 | SEQ ID NO: 22 |
| 83 | SEQ ID NO: 18 | | | | | SEQ ID NO: 22 |
| 84 | SEQ ID NO: 18 | | | SEQ ID NO: 20 | | SEQ ID NO: 22 |
| 85 | SEQ ID NO: 18 | KAS | | SEQ ID NO: 20 | | |
| 86 | SEQ ID NO: 18 | KAS | | SEQ ID NO: 20 | SEQ ID NO: 21 | |
| 87 | SEQ ID NO: 18 | KAS | | SEQ ID NO: 20 | SEQ ID NO: 21 | SEQ ID NO: 22 |
| 88 | SEQ ID NO: 18 | KAS | | | SEQ ID NO: 21 | |
| 89 | SEQ ID NO: 18 | KAS | | | SEQ ID NO: 21 | SEQ ID NO: 22 |
| 90 | SEQ ID NO: 18 | KAS | | | | SEQ ID NO: 22 |
| 91 | SEQ ID NO: 18 | KAS | | SEQ ID NO: 20 | | SEQ ID NO: 22 |
| 92 | SEQ ID NO: 18 | KAS | SEQ ID NO: 19 | SEQ ID NO: 20 | | |

TABLE A-continued

Exemplary Antibodies

| Antibody | Light Chain HVR | | | Heavy Chain HVR | | |
|---|---|---|---|---|---|---|
| | L1 | L2 | L3 | H1 | H2 | H3 |
| 93 | SEQ ID NO: 18 | KAS | SEQ ID NO: 19 | SEQ ID NO: 20 | SEQ ID NO: 21 | |
| 94 | SEQ ID NO: 18 | KAS | SEQ ID NO: 19 | SEQ ID NO: 20 | SEQ ID NO: 21 | SEQ ID NO: 22 |
| 95 | SEQ ID NO: 18 | KAS | SEQ ID NO: 19 | | SEQ ID NO: 21 | |
| 96 | SEQ ID NO: 18 | KAS | SEQ ID NO: 19 | | SEQ ID NO: 21 | SEQ ID NO: 22 |
| 97 | SEQ ID NO: 18 | KAS | SEQ ID NO: 19 | SEQ ID NO: 20 | | SEQ ID NO: 22 |
| 98 | SEQ ID NO: 18 | KAS | SEQ ID NO: 19 | | | SEQ ID NO: 22 |
| 99 | | KAS | | SEQ ID NO: 20 | | |
| 100 | | KAS | | SEQ ID NO: 20 | SEQ ID NO: 21 | |
| 101 | | KAS | | SEQ ID NO: 20 | SEQ ID NO: 21 | SEQ ID NO: 22 |
| 102 | | KAS | | | SEQ ID NO: 21 | |
| 103 | | KAS | | | SEQ ID NO: 21 | SEQ ID NO: 22 |
| 104 | | KAS | | | | SEQ ID NO: 22 |
| 105 | | KAS | | SEQ ID NO: 20 | | SEQ ID NO: 22 |
| 106 | | KAS | SEQ ID NO: 19 | SEQ ID NO: 20 | | |
| 107 | | KAS | SEQ ID NO: 19 | SEQ ID NO: 20 | SEQ ID NO: 21 | |
| 108 | | KAS | SEQ ID NO: 19 | SEQ ID NO: 20 | SEQ ID NO: 21 | SEQ ID NO: 22 |
| 109 | | KAS | SEQ ID NO: 19 | | SEQ ID NO: 21 | |
| 110 | | KAS | SEQ ID NO: 19 | | SEQ ID NO: 21 | SEQ ID NO: 22 |
| 111 | | KAS | SEQ ID NO: 19 | | | SEQ ID NO: 22 |
| 112 | | KAS | SEQ ID NO: 19 | SEQ ID NO: 20 | | SEQ ID NO: 22 |
| 113 | | | SEQ ID NO: 19 | SEQ ID NO: 20 | | |
| 114 | | | SEQ ID NO: 19 | SEQ ID NO: 20 | SEQ ID NO: 21 | |
| 115 | | | SEQ ID NO: 19 | SEQ ID NO: 20 | SEQ ID NO: 21 | SEQ ID NO: 22 |
| 116 | | | SEQ ID NO: 19 | | SEQ ID NO: 21 | |
| 117 | | | SEQ ID NO: 19 | | SEQ ID NO: 21 | SEQ ID NO: 22 |
| 118 | | | SEQ ID NO: 19 | | | SEQ ID NO: 22 |
| 119 | | | SEQ ID NO: 19 | SEQ ID NO: 20 | | SEQ ID NO: 22 |
| 120 | SEQ ID NO: 18 | | SEQ ID NO: 19 | SEQ ID NO: 20 | | |
| 121 | SEQ ID NO: 18 | | SEQ ID NO: 19 | SEQ ID NO: 20 | SEQ ID NO: 21 | |
| 122 | SEQ ID NO: 18 | | SEQ ID NO: 19 | SEQ ID NO: 20 | SEQ ID NO: 21 | SEQ ID NO: 22 |
| 123 | SEQ ID NO: 18 | | SEQ ID NO: 19 | | SEQ ID NO: 21 | |
| 124 | SEQ ID NO: 18 | | SEQ ID NO: 19 | | SEQ ID NO: 21 | SEQ ID NO: 22 |
| 125 | SEQ ID NO: 18 | | SEQ ID NO: 19 | | | SEQ ID NO: 22 |
| 126 | SEQ ID NO: 18 | | SEQ ID NO: 19 | SEQ ID NO: 20 | | SEQ ID NO: 22 |

(c) Spacer

As used herein, the term "spacer" refers to a flexible linker that is positioned between an epitope binding agent and a TRAIL trimer. Prior research in this field indicated that it was necessary to include a large molecular spacer (~40 kDa) between an anti-mesothelin scFv and TR3 to allow the membrane-tethered TRAIL trimer to bend over and engage receptors on the same cell in a productive fashion (i.e., a cis-acting cell death phenotype). See Tatzel et al., "Membrane-proximal TRAIL species are incapable of inducing short circuit apoptosis signaling: Implications for drug development and basic cytokine biology," *Scientific Reports*, 2016, 6: 22661. In the absence of the spacer, mesothelin-positive targets were unexpectedly protected from cell death and were actively enriched following exposure to a spacer-deficient SS-TR3 construct.

In contrast, constructs of the present disclosure do not require a large molecular spacer between the epitope binding agent and the TRAIL trimer to achieve cis-killing of mesothelin positive cells. Without wishing to be bound by theory, it is believed that the epitopes on cell surface human mesothelin that are recognized by the epitope binding agents disclosed herein favorably contribute to the spatial requirements needed for a functional interaction between the TRAIL trimer and DR5 (or other death receptors) at the plasma membrane. Although a spacer is not necessary for constructs disclosed herein to achieve cis-killing, inclusion of a spacer may be desired to further improve cis-killing and/or improve trans-killing.

In some embodiments, a construct comprises a TNF-related apoptosis-inducing ligand (TRAIL) trimer and an epitope binding agent that competitively inhibits binding of scFv-P4 (SEQ ID NO: 6) or scFv-HN1 (SEQ ID NO: 7) to cell surface human mesothelin, wherein the construct does not comprise a spacer.

In other embodiments, a construct comprises (a) a TNF-related apoptosis-inducing ligand (TRAIL) trimer; (b) a spacer; and (c) an epitope binding agent that competitively inhibits binding of scFv-P4 (SEQ ID NO: 6) or scFv-HN1 (SEQ ID NO: 7) to cell surface human mesothelin; wherein the spacer is directly attached to the TRAIL trimer at one end and the epitope binding agent on the other end. In certain embodiments, the spacer is less than about 200 amino acids in length, preferably less than about 100 amino acids in length, more preferably less than preferably less than about 50 amino acids in length, even more preferably less than preferably less than about 25 amino acids in length. In certain embodiments, the spacer is more than about 200 amino acids or less in length. For example, a spacer domain may comprise one or more protein domains from human DAF (SCR1) and CR1 (SCRs 15-17), or any other suitable spacer known in the art. See, for example, U.S. Pat. No. 8,461,311. Generally, an amino acid sequence is selected such that the spacer is flexible. In exemplary embodiments, the spacer comprises one or more glycosylation sites.

(d) Optional Construct Components

Constructs of the present disclosure may further comprise a signal peptide, one or more cleavage sites, and/or one or more epitope tags.

In some embodiments, a construct of the disclosure may further comprise an N-terminal signal peptide. Addition of a signal peptide may be advantageous when secretion of the construct is desired for purification purposes. Suitable signal peptides are known in the art.

In some embodiments, a construct of the disclosure may further comprise one or more cleavage sites. For example, a cleavage site may be between the epitope binding agent and the TRAIL trimer. Alternatively, or in addition, a cleavage site may be between one or more of the extracellular TRAIL domains. In embodiments where the construct comprises a signal peptide, a cleavage site may also be between the signal peptide and the epitope binding agent or the TRAIL trimer, whichever is proximal to the signal peptide. Cleavage sites recognized by various proteases are well known in the art.

In some embodiments, a construct of the disclosure may further comprise one or more tags. A tag may be attached at various positions within the construct including but not limited to the N-terminus, the C-terminus, between the epitope binding agent and the TRAIL trimer, between one or more of the extracellular TRAIL domains of the TRAIL trimer, or to a side chain of any amino acid in the construct provided construct substantially retains the killing capacity of the TRAIL trimer and the ability of the epitope binding agent to competitively inhibit binding of scFv-P4 or scFv-HN1 to cell surface human mesothelin. Non-limiting examples of suitable tags include radioisotopes, fluorophores, chromophores, protein tags, and peptide tags. Techniques for incorporating these tags into a polypeptide are well known in the art.

(e) Exemplary Embodiments

As disclosed herein, a construct of the present disclosure comprises (a) a TNF-related apoptosis-inducing ligand (TRAIL) trimer comprising three extracellular TRAIL domains fused together in a head-to-tail configuration that substantially retains the killing capacity of TRAIL; and (b) an epitope binding agent, wherein the epitope binding agent competitively inhibits binding of scFv-P4 or scFv-HN1 to cell surface human mesothelin.

In an exemplary embodiment, the epitope binding agent is an antibody that has a heavy chain variable region comprising SEQ ID NO: 13, SEQ ID NO: 14, and/or SEQ ID NO: 15; and/or a light chain variable region comprising SEQ ID NO: 10, SEQ ID NO: 11, and/or SEQ ID NO: 12; and the TRAIL trimer is a protein comprising a first peptide, a second peptide and third peptide; wherein each of the first peptide, the second peptide, and the third peptide is $TRAIL_{122-281}$ or a peptide that has an amino acid sequence that has at least 80% sequence identity to $TRAIL_{122-281}$, and the C-terminus of the first peptide is indirectly attached to N-terminus of the second peptide, and the C-terminus of the second peptide is indirectly attached to N-terminus of the third domain; and wherein the first peptide is attached to the second peptide by an amino acid linker that is 1 to 50 amino acids in length, and the second peptide is attached to the third peptide by an amino acid linker that is 1 to 50 amino acids in length.

In another exemplary embodiment, the epitope binding agent is an antibody that has a heavy chain variable region comprising SEQ ID NO: 13, SEQ ID NO: 14, and/or SEQ ID NO: 15; and/or a light chain variable region comprising SEQ ID NO: 10, SEQ ID NO: 11, and/or SEQ ID NO: 12; and the TRAIL trimer is a protein comprising a first peptide, a second peptide and third peptide; wherein each of the first peptide, the second peptide, and the third peptide is $TRAIL_{114-281}$ or a peptide that has an amino acid sequence that has at least 80% sequence identity to $TRAIL_{114-281}$, and the C-terminus of the first peptide is directly or indirectly attached to N-terminus of the second peptide, and the C-terminus of the second peptide is directly or indirectly attached to N-terminus of the third domain When indirectly attached, the first peptide is attached to the second peptide by an amino acid linker that is 1 to 50 amino acids in length, and the second peptide is attached to the third peptide by an amino acid linker that is 1 to 50 amino acids in length.

In another exemplary embodiment, the epitope binding agent is an antibody that a heavy chain variable region comprising SEQ ID NO: 20, SEQ ID NO: 21, and/or SEQ ID NO: 22; and/or a light chain variable region comprising SEQ ID NO: 18, the amino acid sequence KAS, and/or SEQ ID NO: 19; and the TRAIL trimer is a protein comprising a first peptide, a second peptide and third peptide; wherein each of the first peptide, the second peptide, and the third peptide is $TRAIL_{122-281}$ or a peptide that has an amino acid sequence that has at least 80% sequence identity to $TRAIL_{122-281}$, and the C-terminus of the first peptide is indirectly attached to N-terminus of the second peptide, and the C-terminus of the second peptide is indirectly attached to N-terminus of the third domain; and wherein the first peptide is attached to the second peptide by an amino acid linker that is 1 to 50 amino acids in length, and the second peptide is attached to the third peptide by an amino acid linker that is 1 to 50 amino acids in length.

In another exemplary embodiment, the epitope binding agent is an antibody that a heavy chain variable region comprising SEQ ID NO: 20, SEQ ID NO: 21 and/or SEQ ID NO: 22; and/or a light chain variable region comprising SEQ ID NO: 18, the amino acid sequence KAS, and/or SEQ ID NO: 19]; and the TRAIL trimer is a protein comprising a first peptide, a second peptide and third peptide; wherein each of the first peptide, the second peptide, and the third peptide is $TRAIL_{114-281}$ or a peptide that has an amino acid sequence that has at least 80% sequence identity to $TRAIL_{114-281}$, and the C-terminus of the first peptide is directly or indirectly attached to N-terminus of the second peptide, and the C-terminus of the second peptide is directly or indirectly attached to N-terminus of the third domain. When indirectly attached, the first peptide is attached to the second peptide by an amino acid linker that is 1 to 50 amino acids in length, and the second peptide is attached to the third peptide by an amino acid linker that is 1 to 50 amino acids in length.

In another exemplary embodiment, the epitope binding agent is an antibody that has a heavy chain variable region comprising SEQ ID NO: 13, SEQ ID NO: 14, and/or SEQ ID NO: 15; and/or a light chain variable region comprising SEQ ID NO: 10, SEQ ID NO: 11, and/or SEQ ID NO: 12; and the TRAIL trimer is a protein comprising a first peptide, a second peptide and third peptide; wherein the first peptide is $TRAIL_{91-281}$ or a peptide that has an amino acid sequence that has at least 80% sequence identity to $TRAIL_{91-281}$, and each of the second peptide, and the third peptide is $TRAIL_{114-281}$ or a peptide that has an amino acid sequence that has at least 80% sequence identity to $TRAIL_{114-281}$, and the C-terminus of the first peptide is directly or indirectly attached to N-terminus of the second peptide, and the C-terminus of the second peptide is directly or indirectly attached to N-terminus of the third domain. When indirectly attached, the first peptide is attached to the second peptide by an amino acid linker that is 1 to 50 amino acids in length, and the second peptide is attached to the third peptide by an amino acid linker that is 1 to 50 amino acids in length.

In another exemplary embodiment, the epitope binding agent is an antibody that a heavy chain variable region comprising SEQ ID NO: 20, SEQ ID NO: 21 and/or SEQ ID NO: 22; and/or a light chain variable region comprising SEQ ID NO: 18, the amino acid sequence KAS, and/or SEQ ID NO: 19; and the TRAIL trimer is a protein comprising a first peptide, a second peptide and third peptide; wherein the first peptide is $TRAIL_{91-281}$ or a peptide that has an amino acid sequence that has at least 80% sequence identity to $TRAIL_{91-281}$, and each of the second peptide, and the third peptide is $TRAIL_{114-281}$ or a peptide that has an amino acid sequence that has at least 80% sequence identity to $TRAIL_{114-281}$, and the C-terminus of the first peptide is directly or indirectly attached to N-terminus of the second peptide, and the C-terminus of the second peptide is directly or indirectly attached to N-terminus of the third domain. When indirectly attached, the first peptide is attached to the second peptide by an amino acid linker that is 1 to 50 amino acids in length, and the second peptide is attached to the third peptide by an amino acid linker that is 1 to 50 amino acids in length.

In another exemplary embodiment, the epitope binding agent is scFv-HN1 and the TRAIL trimer is a protein comprising a first peptide, a second peptide and third peptide; wherein each of the first peptide, the second peptide, and the third peptide is $TRAIL_{114-281}$ or a peptide that has an amino acid sequence that has at least 80% sequence identity to $TRAIL_{114-281}$, and the C-terminus of the first peptide is directly or indirectly attached to N-terminus of the second peptide, and the C-terminus of the second peptide is directly or indirectly attached to N-terminus of the third domain. When indirectly attached, the first peptide is attached to the second peptide by an amino acid linker that is 1 to 50 amino acids in length, and the second peptide is attached to the third peptide by an amino acid linker that is 1 to 50 amino acids in length.

In another exemplary embodiment, the epitope binding agent is scFv-P4 and the TRAIL trimer is a protein comprising a first peptide, a second peptide and third peptide; wherein each of the first peptide, the second peptide, and the third peptide is $TRAIL_{114-281}$ or a peptide that has an amino acid sequence that has at least 80% sequence identity to $TRAIL_{114-281}$, and the C-terminus of the first peptide is directly or indirectly attached to N-terminus of the second peptide, and the C-terminus of the second peptide is directly or indirectly attached to N-terminus of the third domain. When indirectly attached, the first peptide is attached to the second peptide by an amino acid linker that is 1 to 50 amino acids in length, and the second peptide is attached to the third peptide by an amino acid linker that is 1 to 50 amino acids in length.

In another exemplary embodiment, the epitope binding agent is scFv-HN1 and the TRAIL trimer is a protein comprising a first peptide, a second peptide and third peptide; wherein the first peptide is $TRAIL_{91-281}$ or a peptide that has an amino acid sequence that has at least 80% sequence identity to $TRAIL_{91-281}$, and each of the second peptide, and the third peptide is $TRAIL_{114-281}$ or a peptide that has an amino acid sequence that has at least 80% sequence identity to $TRAIL_{114-281}$, and the C-terminus of the first peptide is directly or indirectly attached to N-terminus of the second peptide, and the C-terminus of the second peptide is directly or indirectly attached to N-terminus of the third domain. When indirectly attached, the first peptide is attached to the second peptide by an amino acid linker that is 1 to 50 amino acids in length, and the second peptide is attached to the third peptide by an amino acid linker that is 1 to 50 amino acids in length.

In another exemplary embodiment, the epitope binding agent is scFv-P4 and the TRAIL trimer is a protein comprising a first peptide, a second peptide and third peptide; wherein the first peptide is $TRAIL_{91-281}$ or a peptide that has an amino acid sequence that has at least 80% sequence identity to $TRAIL_{91-281}$, and each of the second peptide, and the third peptide is $TRAIL_{114-281}$ or a peptide that has an amino acid sequence that has at least 80% sequence identity to $TRAIL_{114-281}$, and the C-terminus of the first peptide is directly or indirectly attached to N-terminus of the second peptide, and the C-terminus of the second peptide is directly or indirectly attached to N-terminus of the third domain. When indirectly attached, the first peptide is attached to the second peptide by an amino acid linker that is 1 to 50 amino acids in length, and the second peptide is attached to the third peptide by an amino acid linker that is 1 to 50 amino acids in length.

In another exemplary embodiment, the epitope binding agent is an antibody that has a heavy chain variable region comprising SEQ ID NO: 13, SEQ ID NO: 14, and/or SEQ ID NO: 15; and/or a light chain variable region comprising SEQ ID NO: 10, SEQ ID NO: 11, and/or SEQ ID NO: 12; and the TRAIL trimer is TR3.

In another exemplary embodiment, the epitope binding agent is an antibody that a heavy chain variable region comprising SEQ ID NO: 20, SEQ ID NO: 21, and/or SEQ ID NO: 22; and/or a light chain variable region comprising SEQ ID NO: 18, the amino acid sequence KAS, and/or SEQ ID NO: 19; and the TRAIL trimer is TR3.

In each of the above exemplary embodiments, the epitope binding agent is either N-terminal or C-terminal to the TRAIL trimer; and the epitope binding agent is either directly attached to the TRAIL trimer or attached by a spacer that consists of no more than 100 amino acids (or a non-amino acid spacer that is equivalent in terms of size and flexibility).

In another exemplary embodiment, the construct is P4-TR3 (SEQ ID NO: 26).

In another exemplary embodiment, the construct is HN1-TR3 (SEQ ID NO: 25).

II. Nucleic Acids Encoding Constructs

Another aspect of the present disclosure provides nucleic acids encoding any of the constructs described above in Section I. The nucleic acid can be RNA or DNA. In one embodiment, the nucleic acid encoding the construct is mRNA. The m RNA can be 5' capped and/or 3' polyadenylated. In another embodiment, the nucleic acid encoding the construct is DNA. The DNA can be present in a vector (see below).

In some embodiments, DNA encoding the construct can be operably linked to at least one promoter control sequence. In some iterations, the DNA coding sequence can be operably linked to a promoter control sequence for expression in a eukaryotic cell of interest. The promoter control sequence can be constitutive or regulated. Suitable constitutive promoter control sequences include, but are not limited to, cytomegalovirus immediate early promoter (CMV), simian virus (SV40) promoter, human elongation factor-1 alpha (EF-1 alpha) promoter, adenovirus major late promoter, Rous sarcoma virus (RSV) promoter, mouse mammary tumor virus (MMTV) promoter, phosphoglycerate kinase (PGK) promoter, elongation factor (EDI)-alpha promoter, ubiquitin promoters, actin promoters, tubulin promoters, immunoglobulin promoters, fragments thereof, or combinations of any of the foregoing. Examples of suitable regulated promoter control sequences include without limit those regulated by heat shock, metals, steroids, antibiotics, or alcohol. Non-limiting examples of tissue-specific promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, Nphsl promoter, OG-2 promoter, SP-B promoter, SYN1 promoter, and WASP promoter. The promoter sequence can be wild type or it can be modified for more efficient or efficacious expression. The promoter sequence can be wild type or it can be modified for more efficient or efficacious expression.

In certain embodiments, the sequence encoding the construct can be operably linked to a promoter sequence that is recognized by a phage RNA polymerase for in vitro mRNA synthesis. For example, the promoter sequence can be a T7, T3, or SP6 promoter sequence or a variation of a T7, T3, or SP6 promoter sequence.

In alternate embodiments, the sequence encoding the construct can be operably linked to a promoter sequence for in vivo expression of the construct in bacterial or eukaryotic cells. In such embodiments, the expressed protein can be purified for use in the methods detailed below in Sections III and IV. Suitable bacterial promoters include, without limit, T7 promoters, lac operon promoters, trp promoters, variations thereof, and combinations thereof. An exemplary bacterial promoter is tac which is a hybrid of trp and lac promoters. Non-limiting examples of suitable eukaryotic promoters are listed above.

In additional aspects, the DNA encoding the construct can be linked to a polyadenylation signal (e.g., SV40 polyA signal, bovine growth hormone (BGH) polyA signal, etc.) and/or at least one transcriptional termination sequence. Additionally, the sequence encoding the construct also can be linked to a sequence encoding at least one nuclear localization signal or at least one cell-penetrating domain.

In various embodiments, the DNA sequence encoding the construct can be present in a vector. Suitable vectors include plasmid vectors, phagemids, cosmids, artificial/mini-chromosomes, transposons, and viral vectors. In one embodiment, the DNA encoding the construct is present in a plasmid vector. Non-limiting examples of suitable plasmid vectors include pUC, pBR322, pET, pBluescript, and variants thereof. In another embodiment, the DNA encoding the construct is present in a viral vector. Non-limiting examples of suitable plasmid vectors include lentiviral vectors, adeno-associated viral vectors, adenovirus vectors, alphavirus vectors, herpesvirus vectors, and vaccinia virus vectors. In such embodiments, the expressed viral vector can be purified for use in the methods detailed below in Sections III and IV. In an exemplary embodiment, a DNA sequence encoding a construct of Section I is present in an Ad5 vector or a modified Ad5 vector. In another exemplary embodiment, a DNA sequence encoding a construct of Section I is present in Ad5pK7. The vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. Additional information can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, NY, 3rd edition, 2001.

In some embodiments, the expression vector comprising the DNA sequence encoding the construct is operably linked to at least one transcriptional control sequence for expression of the construct in a cell of interest. For example, DNA encoding the construct can be operably linked to a promoter sequence that is recognized by RNA polymerase III (Pol III). Examples of suitable Pol III promoters include, but are not limited to, mammalian U6, U3, H1, and 7SL RNA promoters.

III. Methods of Treatment

Another aspect of the present disclosure provides methods of treatment that comprise administering to a subject in need thereof a therapeutically effective amount of a construct of Section I or Section II, or a DNA or an RNA virus encoding a construct of Section I. As used herein, the terms "treat," "treating," or "treatment" refer to both therapeutic treatment and prophylactic or preventative measures, wherein the object is to prevent or slow down (lessen) an undesired physiological change or disease/disorder as compared to an untreated subject with a similar disease, condition or disorder. Beneficial or desired clinical results include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment.

Subjects in need of treatment include those already with a disease, a condition, or a disorder associated with increased cell-surface expression of mesothelin, as well as those prone to have the disease, condition or disorder or those in which the disease, condition or disorder is to be prevented. Preferred subjects are mammals, more preferably humans, and include both adult and pediatric subjects. Non-limiting examples of diseases, conditions, or disorders associated with increased expression of cell-surface mesothelin include liver fibrosis, lung fibrosis, acute kidney injury, chronic kidney disease, and cancer (i.e., a malignant tumor).

When a subject in need of treatment is a subject diagnosed with cancer, the subject may have active disease or may be in remission (complete or partial). When a subject with cancer has active disease, treatment may reduce the size of the tumor, slow or inhibit growth of the tumor, slow or inhibit metastasis, or any combination thereof. For subjects in partial remission, treatment may reduce the size of the tumor, slow or inhibit growth of the tumor, slow or inhibit metastasis, or any combination thereof. When a subject is in complete remission, treatment may prevent a cancer from re-growing (i.e. disease progression). In subjects with active disease or in remission, treatment may also prolong survival as compared to an untreated patient.

As used herein, the term "cancer" includes solid tumors, non-solid tumors, and circulating tumor cells. Solid tumors are formed by an abnormal growth of cells other than blood, bone marrow or lymphatic cells, and include tumors that are not vascularized, or not yet substantially vascularized, as well as vascularized tumors. Non-limiting examples of solid tumors include sarcomas and carcinomas. Different types of solid tumors are named for the type of cells that form them. Non-limiting examples of malignant solid tumors associated with overexpression of mesothelin include ovarian cancer, pancreatic cancer, lung cancer, esophageal cancer, gastric cancer, colon cancer, kidney cancer, liver cancer, synovial sarcoma, triple-negative breast cancer, cervical cancer, or mesothelioma. Non-solid tumors usually originate from blood-forming tissues. Non-limiting examples of malignant non-solid tumors associated with overexpression of mesothelin include leukemia, lymphoma and multiple myeloma. Circulating tumor cells are cancer cells that detach from a primary tumor and travel through the bloodstream or lymphatic system to other parts of the body. Methods for detecting circulating tumor cells.

In one embodiment, treating a subject in need thereof by administering to the subject a therapeutically effective amount of a construct of Section I or Section II, or a DNA or an RNA virus encoding a construct of Section I, may increase survival of the subject as compared to expected survival if the subject did not receive treatment. Survival may be increased at least about 5%. For example, survival may be increase at least about 5%, at least about 10%, at least about 15%, or at least about 20%. In another example, survival may be increased by at least about 25%, at least about 30%, at least about 35%, or at least about 40%. In still another example, survival may be increased by at least about 50%, at least about 100%, at least about 150%, at least about 200%, or more. In subjects diagnosed with cancer, survival may refer to overall survival or progression free survival (i.e., the length of time the subject is both alive and free from any significant increase in cancer).

In another embodiment, treating a subject in need thereof by administering to the subject therapeutically effective amount of a construct of Section I or Section II, or a DNA or an RNA virus encoding a construct of Section I, may alleviate or ameliorate one or more signs or symptoms of a disease, a condition, or a disorder associated with increased expression of cell-surface mesothelin. In certain embodiments, the subject is diagnosed with cancer. Non-limiting examples symptoms associated with cancer that may be alleviated include, fatigue, unintended weight loss or gain, pain, fevers, frequent infections, and easy bleeding or bruising.

In another embodiment, treating a subject diagnosed with cancer by administering to the subject a therapeutically effective amount of a construct of Section I or Section II, or a DNA or an RNA virus encoding a construct of Section I, may decrease tumor volume. For example, tumor volume may decrease by less than 25%, by about 25% to about 50%, or by about 50% to about 100%. In certain embodiments, treatment may result in no evidence of disease, i.e., all detectable tumor has disappeared in the subject. Response duration may vary depending upon the type of cancer and the severity of disease. In certain embodiments, the cancer is selected from ovarian cancer, cervical cancer, pancreatic cancer, mesothelioma or lung cancer.

In another embodiment, treating a subject diagnosed with cancer by administering to the subject a therapeutically effective amount of a construct of Section I or Section II, or a DNA or an RNA virus encoding a construct of Section I, may decrease the number of circulating tumor cells. For example, the number of circulating tumor cells may decrease by less than 25%, by about 25% to about 50%, or by about 50% to about 100%. Method for detecting circulating tumor cells are known in the art. In certain embodiments, the cancer is selected from cervical cancer, pancreatic cancer, mesothelioma or lung cancer.

In another embodiment, administering to a subject diagnosed with cancer a therapeutically effective amount of a construct of Section I or Section II, or a DNA or an RNA virus encoding a construct of Section I, may decrease the risk of metastasis as compared to an untreated patient. The risk of metastasis may be decreased by at least about 5%. For example, the risk of metastasis may be decreased (as compared to an untreated patient) by at least about 5%, at least about 10%, at least about 15%, or at least about 20%. In another example, the risk of metastasis may be decreased (as compared to an untreated patient) by at least about 25%, at least about 30%, at least about 35%, or at least about 40%. In still another example, the risk of metastasis may be decreased (as compared to an untreated patient) by at least about 50%, at least about 75%, or at least about 90%, or more. In certain embodiments, the cancer is selected from ovarian cancer, cervical cancer, pancreatic cancer, mesothelioma or lung cancer.

For each of the above embodiments, suitable constructs are described in Section I or Section II. In an exemplary embodiment, the construct comprises scFv-HN1 (SEQ ID NO: 7) and TR3 (SEQ ID NO: 2). In another exemplary embodiment, the construct comprises scFv-P4 (SEQ ID NO: 6) and TR3 (SEQ ID NO: 2).

Constructs of the present disclosure may be used alone or in combination with one or more additional therapeutic agent known to effectively treat a disease, a condition, or a disorder associated with dysregulated expression of mesothelin. For example, when a subject is diagnosed with cancer, constructs of the present disclosure may be combined with standard-of-care cancer therapies. As used herein, "standard-of-care cancer therapies" refer to one or more treatments accepted by medical experts as a proper treatment for a certain type of disease and that is widely used by healthcare professionals. Standard-of-care cancer therapies for cancer include, but are not limited to, cytotoxic agents, cytostatic agents, chemotherapeutic agents, targeted anti-cancer agents, biological response modifiers, immunotherapeutic agents, cancer vaccines, anti-angiogenic agents, cytokines, hormone therapies, radiation therapy and anti-metastatic agents.

Administration of a construct of Section I, Section II, or a DNA or an RNA virus encoding a construct of Section I, or a composition comprising a construct of Section I, Section II, or a DNA or an RNA virus encoding a construct of Section I, is performed using standard effective techniques. Administration may occur orally, parenterally, by inhalation, rectally, intradermally, transdermally, or topically in dosage unit formulations containing conventional nontoxic pharmaceutically acceptable carriers, adjuvants, and vehicles as desired. The term parenteral as used herein includes subcutaneous, intravenous, intramuscular, intrathecal, or intrasternal injection, or infusion techniques.

Although the foregoing methods appear the most convenient and most appropriate and effective for administration, by suitable adaptation other effective techniques for administration may be employed provided proper formulation is utilized herein. For example, a person skilled in the art can use a nucleic acid of the invention encoding a construct of Section I instead of the protein material itself.

In addition, it may be desirable to employ controlled release formulations using biodegradable films and matrices, or osmotic mini-pumps, or delivery systems based on dextran beads, alginate, or collagen.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

The concentration of a construct or combination of constructs in formulations to be administered is an effective amount and ranges from as low as about 0.1% by weight to as much as about 15 or about 20% by weight and will be selected primarily based on fluid volumes, viscosities, and so forth, in accordance with the particular mode of administration selected if desired. A typical composition for injection to a living subject could be made up to contain 1 mL sterile buffered water of phosphate buffered saline and about 1-1000 mg of any one of or a combination of constructs of Section I or Section II disclosed herein. The formulation could be sterile filtered after making the formulation, or otherwise made microbiologically acceptable. A typical composition for intravenous infusion could have volumes between 1-250 mL of fluid, such as sterile Ringer's solution, and 1-100 mg per ml, or more in concentration of a construct of Section I or Section II. The construct of Section I or Section II disclosed herein can be frozen or lyophilized for storage and reconstituted in a suitable sterile carrier prior to use. Lyophilization and reconstitution may lead to varying degrees of activity loss of a construct of Section I or Section II. Dosages administered are effective dosages and may have to be adjusted to compensate. The pH of the formulations, generally pharmaceutical grade quality, will be selected to balance recombinant protein stability (chemical and physical) and comfort to the subject when administered. Generally, a pH between 4 and 8 is tolerated. Doses will vary from individual to individual based on size, weight, and other physiobiological characteristics of the individual receiving the successful administration.

Methods for administering a DNA or an RNA virus are well-known in the art. Although the exact dosage will be determined on a drug-by-drug basis, in most cases, some generalizations regarding the dosage can be made. In some embodiments, the recombinant a DNA or an RNA virus encoding a construct of Section I can be administered via injection to a subject at a dose of about $1\times10^9$ genome copies (GC) of the recombinant virus per kg of the subject to about $1\times10^{13}$ GC per kg, for example about $1\times10^9$ GC/kg to $1\times10^{10}$ GC/kg, about $1\times10^9$ GC/kg to $5\times10^{10}$ GC/kg, about $1\times10^9$ GC/kg to $1\times10^{11}$ GC/kg, about $1\times10^9$ GC/kg to $5\times10^{11}$ GC/kg, about $1\times10^9$ GC/kg to $1\times10^{12}$ GC/kg, about $1\times10^9$ GC/kg to $5\times10^{12}$ GC/kg, about $1\times10^9$ GC/kg to $1\times10^{13}$ GC/kg, about $5\times10^9$ GC/kg to $1\times10^{10}$ GC/kg, about $5\times10^9$ GC/kg to $5\times10^{10}$ GC/kg, about $5\times10^9$ GC/kg to $1\times10^{11}$ GC/kg, about $5\times10^9$ GC/kg to $5\times10^{11}$ GC/kg, about $5\times10^9$ GC/kg to $1\times10^{12}$ GC/kg, about $5\times10^9$ GC/kg to $5\times10^{12}$ GC/kg, about $5\times10^9$ GC/kg to $1\times10^{13}$ GC/kg, about $1\times10^{10}$ GC/kg to $5\times10^{10}$ GC/kg, about $1\times10^{10}$ GC/kg to $1\times10^{11}$ GC/kg, about $1\times10^{10}$ GC/kg to $5\times10^{11}$ GC/kg, about $1\times10^{10}$ GC/kg to $1\times10^{12}$ GC/kg, about $1\times10^{10}$ GC/kg to $5\times10^{12}$ GC/kg, about $1\times10^{10}$ GC/kg to $1\times10^{13}$ GC/kg, about $5\times10^{10}$ GC/kg to $1\times10^{11}$ GC/kg, about $5\times10^{10}$ GC/kg to $1\times10^{12}$ GC/kg, about $5\times10^{10}$ GC/kg to $5\times10^{12}$ GC/kg, about $5\times10^{10}$ GC/kg to $1\times10^{13}$ GC/kg, about $1\times10^{11}$ GC/kg to $5\times10^{11}$ GC/kg, about $1\times10^{11}$ GC/kg to $1\times10^{12}$ GC/kg, about $1\times10^{11}$ GC/kg to $5\times10^{12}$ GC/kg, about $1\times10^{11}$ GC/kg to $1\times10^{13}$ GC/kg, about $5\times10^{11}$ GC/kg to $1\times10^{12}$ GC/kg, or about $5\times10^{11}$ GC/kg to $1\times10^{13}$ GC/kg.

Actual administration of the AAV vector encoding a gene product of interest, expression system, or component thereof can be accomplished by using any physical method that will transport the recombinant AAV vector into the target tissue of the subject. For example, the recombinant AAV vector can be injected into muscle, the bloodstream, and/or directly into the liver. Capsid proteins of the recombinant AAV vector may be modified so that the recombinant AAV vector is targeted to a particular target tissue of interest such as muscle or bone marrow. Pharmaceutical compositions can be prepared as injectable formulations or as topical formulations to be delivered to the muscles by transdermal transport.

For intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the AAV vector as a free acid (DNA contains acidic phosphate groups) or a pharmacologically acceptable salt can be prepared in water suitably mixed with a surfactant such as hydroxypropylcellulose. A dispersion of the AAV vector can also be prepared in glycerol, liquid polyethylene glycols and mixtures thereof and in oils. Under ordinary conditions of storage and use, these preparations contain a preservative to prevent the growth of microorganisms.

The AAV vector to be used can be utilized in liquid or freeze-dried form (in combination with one or more suitable preservatives and/or protective agents to protect the virus during the freeze-drying process). For gene therapy (e.g., of neurological disorders which may be ameliorated by a specific gene product) a therapeutically effective dose of the recombinant virus expressing the therapeutic protein is administered to a host in need of such treatment. The use of the recombinant virus disclosed herein in the manufacture of a medicament for inducing immunity in, or providing gene therapy to, a host is within the scope of the present application. In some embodiments, the AAV can be administered to a cell that is subsequently transplanted into the host, for example a hematopoietic stem cell, embryonic stem cell, induced pluripotent stem cell, or the like.

In instances where human dosages for the AAV vectors have been established for at least some condition, those same dosages, or dosages that are between about 0.1% and 500%, more preferably between about 25% and 250% of the established human dosage can be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

The timing of administration of the treatment relative to the disease itself and duration of treatment will be determined by the circumstances surrounding the case. Duration of treatment could range from a single dose administered on a one-time basis to a life-long course of therapeutic treatments. In another embodiment of the present disclosure, a treatment regimen composed of a construct of Section I or Section II, or a DNA or an RNA virus encoding a construct of Section I, may include treatment of the subject once or multiple times. In another embodiment, treatment of the subject with a construct of Section I or Section II, or a DNA or an RNA virus encoding a construct of Section I, may occur multiple times until desired results are observed. It is appreciated that one skilled in the art would be able to select an appropriate number of treatments to achieve the desired response for purposes of the present disclosure. In another embodiment of the present disclosure, a subject may be treated with a construct of Section I or Section II, or a DNA or an RNA virus encoding a construct of Section I, multiple times at irregular intervals. In yet another embodiment, a subject may be treated with a construct of Section I or Section II, or a DNA or an RNA virus encoding a construct of Section I, multiple times at regular intervals. In still another embodiment, a subject may be treated with a construct of Section I or Section II, or a DNA or an RNA virus encoding a construct of Section I, multiple times at about at least 2-week or greater, at least 3-week or greater, at least 4-week or greater, at least 5-week or greater, at least 6-week or greater intervals. In another embodiment, a subject may be treated with a construct of Section I or Section II, or a DNA or an RNA virus encoding a construct of Section I, multiple times at about at least 2-week or greater to at least 3-week or greater, at least 3-week or greater to at least 4-week or greater, at least 4-week or greater to at least 5-week or greater, at least 5-week or greater to at least 6-week or greater intervals. It is appreciated that one skilled in the art would be able to select an appropriate interval of treatment to achieve the desired response for purposes of the present disclosure.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that changes may be made in the specific embodiments that are disclosed and still obtain a like or similar result without departing from the spirit and scope of the invention. Therefore, all matter set forth or shown in the accompanying drawings is to be interpreted as illustrative and not in a limiting sense.

IV. Methods for Using a Construct to Induce Apoptosis in a Cell

Another aspect of the present disclosure provides methods of inducing apoptosis in a cell. The method comprises contacting a cell with an effective amount of a construct of Section I or Section II, or a DNA or an RNA virus encoding a construct of Section I. Constructs of the present disclosure target a TRAIL trimer to mesothelin-positive cells in a manner that results in death of the cell to which the construct is bound (i.e., a cis-acting phenotype). In certain embodiment, constructs also result in bystander cell death (i.e., a trans-acting phenotype).

A variety of cells can be used in the method disclosed herein, provided the cell expresses cell surface human mesothelin and either DR4 (RefSeq NP_003835) or DR5 (NP_003833 or NP_671716). In general, the cell is a eukaryotic cell. In various aspects, the cell can be a human cell, a non-human mammalian cell, a non-mammalian vertebrate cell, an invertebrate cell, an insect cell, a plant cell, a yeast cell, or a single cell eukaryotic organism. In exemplary aspects, the cell is a human cell. The cell can be a primary cell or a cell line cell. The cell may be an adult cell, an embryonic cell, or a stem cell. The cell can be a normal cell, a diseased cell, or a cancerous cell.

In some embodiments, the cell can be a human cell line cell. Non-limiting examples of suitable cell lines include DU145 (metastatic cancer), SW490 (colon cancer), DLD-1 (colon cancer), KM20L2 (colon cancer), COLO 205 (colon cancer), HCC-2998, (colon cancer), HCT-1 16 (colon cancer), HCT-15 (colon cancer), HT29 (colon cancer), KM12 (colon cancer), SW-620 (colon cancer), SF-268 (CNS), SF-295 (CNS), SF-539 (CNS), SNB-19 (CNS), SNB-75 (CNS), U251 (CNS), CCRF-CEM (leukemia), HL-60 (TB) (leukemia), K-562 (leukemia), MOLT-4 (leukemia), RPMI-8226 (leukemia), SR (leukemia), A549 (non-small cell lung cancer), EKVX (non-small cell lung cancer), HOP-62 (non-small cell lung cancer), HOP-92 (non-small cell lung cancer), NCI-H226 (non-small cell lung cancer), NCI-H23 (non-small cell lung cancer), NCI-H322M (non-small cell lung cancer), NCI-H460 (non-small cell lung cancer), NCI-H522 (non-small cell lung cancer), LOX IMVI (melanoma), MALME-3M (melanoma), M14 (melanoma), MDA-MB-435 (melanoma), SK-MEL-2 (melanoma), SK-MEL-28 (melanoma), SK-MEL-5 U (melanoma), ACC-257 (melanoma), UACC-62 (melanoma), IGR-OV1 (ovarian), OVCAR-3 (ovarian), OVCAR-4 OVCAR-5 (ovarian), OVCAR-8 (ovarian), SK-OV-3 (ovarian), 786-0 (renal), A498 (renal), ACHN (renal), CAKI-1 (renal), RXF 393 (renal), SN12C (renal), TK-10 (renal), UO-31 (renal), PC-3 (prostate), DU-145 (prostate), MCF7 (breast), MDA-MB-231 (breast), MDA-MB-468 (breast), HS 578T (breast), BT-549 (breast), and T-47D (breast).

In other embodiments, the cell can be a primary human cell. For example, the cell can be diseased or cancerous cell obtained from a subject in need of treatment. The term "subject in need of treatment" is defined above in Section III. The cell can be in a purified form (partially or completely) or can be in a biological sample obtained from the subject (e.g., blood, plasma, lymphatic fluid, etc.). In an exemplary embodiment, the cell can be a circulating tumor cell.

Contacting a cell with an effective amount of a construct of Section I generally involves admixing the construct and the cell for a period of time sufficient to allow the epitope binding agent of the construct to bind mesothelin on the surface of the cell. This may occur in vitro or ex vivo. Contacting a cell with an effective amount of a construct of Section II generally involves transfecting a cell with a construct of Section II. Contacting a cell with an effective amount of a DNA or an RNA virus encoding a construct of Section I generally involves infecting a cell with an effective amount of viral particle. See, for example, Kuroki et al., PLoS ONE, 2017, 12(12): e0190125. This may occur in vitro or ex vivo. The term "effective amount", as used herein, means an amount of a construct that leads to measurable effect, e.g., engagement of a cell death receptor, signaling through a cell death receptor, apoptosis, etc. The effective amount may be determined by using the methods described in further detail in the examples.

| SEQ ID NO | SEQUENCE | DESCRIPTION |
|---|---|---|
| 1 | MAMMEVQGGPSLGQTCVLIVIFTVLLQSLCVAVTYVYFTNELKQMQDKYSK SGIACFLKEDDSYWDPNDEESMNSPCWQVKWQLRQLVRKMILRTSEETIST VQEKQQNISPLVRERGPQRVAAHITGTRGRSNTLSSPNSKNEKALGRKINS WESSRSGHSFLSNLHLRNGELVIHEKGFYYIYSQTYFRFQEEIKENTKNDK QMVQYIYKYTSYPDPILLMKSARNSCWSKDAEYGLYSIYQGGIFELKENDR IFVSVTNEHLIDMDHEASFFGAFLVG | Human TRAIL |
| 2 | LPPRTPPMILRTSEETISTVQEKQQNISPLVRERGPQRVAAHITGTRGRSN TLSSPNSKNEKALGRKINSWESSRSGHSFLSNLHLRNGELVIHEKGFYYIY SQTYFRFQEEIKENTKNDKQMVQYIYKYTSYPDPILLMKSARNSCWSKDAE | TR3 |

| SEQ ID NO | SEQUENCE | DESCRIPTION |
|---|---|---|
| | YGLYSIYQGGIFELKENDRIFVSVTNEHLIDMDHEASFFGAFLVGRSQNIS PLVRERGPQRVAAHITGTRGRSNTLSSPNSKNEKALGRKINSWESSRSGHS FLSNLHLRNGELVIHEKGFYYIYSQTYFRFQEEIKENTKNDKQMVQYIYKY TSYPDPILLMKSARNSCWSKDAEYGLYSIYQGGIFELKENDRIFVSVTNEH LIDMDHEASFFGAFLVGRSQNISPLVRERGPQRVAAHITGTRGRSNTLSSP NSKNEKALGRKINSWESSRSGHSFLSNLHLRNGELVIHEKGFYYIYSQTYF RFQEEIKENTKNDKQMVQYIYKYTSYPDPILLMKSARNSCWSKDAEYGLYS IYQGGIFELKENDRIFVSVTNEHLIDMDHEASFFGAFLVGRS | |
| 3 | MGIQGGSVLFGLLLVLAVFCHSGHSLPPRTPPMILRTSEETISTVQEKQQN ISPLVRERGPQRVAAHITGTRGRSNTLSSPNSKNEKALGRKINSWESSRSG HSFLSNLHLRNGELVIHEKGFYYIYSQTYFRFQEEIKENTKNDKQMVQYIY KYTSYPDPILLMKSARNSCWSKDAEYGLYSIYQGGIFELKENDRIFVSVTN EHLIDMDHEASFFGAFLVGRSQNISPLVRERGPQRVAAHITGTRGRSNTLS SPNSKNEKALGRKINSWESSRSGHSFLSNLHLRNGELVIHEKGFYYIYSQT YFRFQEEIKENTKNDKQMVQYIYKYTSYPDPILLMKSARNSCWSKDAEYGL YSIYQGGIFELKENDRIFVSVTNEHLIDMDHEASFFGAFLVGRSQNISPLV RERGPQRVAAHITGTRGRSNTLSSPNSKNEKALGRKINSWESSRSGHSFLS NLHLRNGELVIHEKGFYYIYSQTYFRFQEEIKENTKNDKQMVQYIYKYTSY PDPILLMKSARNSCWSKDAEYGLYSIYQGGIFELKENDRIFVSVTNEHLID MDHEASFFGAFLVGRS | Signal peptide (SP) + TR3 |
| 4 | EVEKTACPSGKKAPEIDESLIFYKKWELEACVDAALLATQMDRVNAIPFTY EQLDVLKHKLDELYPQGYPESVIQHLGYLFLKMSPEDIRKWNVTSLETLKA LLEVNKGHEMSPQVATLIDRFVKGRGQLDKDTLDTLTAFYPGYLCSLSPEE LSSVPPSSIWAVRPQDLDTCDPRQLDVLYPKARLAFQNMNGSEYFVKIQSF LGGAPTEDLKALSQQNVSMDLATFMKLRTDAVLPLTVAEVQKLLGPHVEGL KAEERHRPVRDWILRQRQDDLDTLGLGLQGGIPNGYLVLDLSMQEALSGTP CLLGPGPVLTVLALLLASTLA | Mesothelin (mature form) |
| 5 | QVQLQQSGPELEKPGASVKISCKASGYSFTGYTMNWVKQSHGKSLEWIGLI SSTPYNGASSYNQKFRGKATLTVDKSSSTAYMDLLSLTSEDSAVYFCARGGYD GRGFDYWGQGTTVTVSSGVGGSGGGGSGGGGSDIELTQSPAIMSASPGEKV TMTCSASSSVSYMHWYQQKSGTSPKRWIYDTSKLASGVPGRFSGSGSGNSY SLTISSVEAEDDATYYCQQWSGYPLTFGAGTKLEIKRA | |
| 6 | QVQLQQSGPGLVTPSQTLSLTCAISGDSVSSNSATWNWIRQSPSRGLEWLG RTYYRSKWYNDYAVSVKSRMSINPDTSKNQFSLQLNSVTPEDTAVYYCARG MMTYYYGMDVWGQGTTVTVSSGILGSGGGGSGGGGSGGGGSQPVLTQSSSL SASPGASASLTCTLRSGINVGPYRIYWYQQKPGSPPQYLLNYKSDSDKQQG SGVPSRFSGSKDASANAGVLLISGLRSEDEADYYCMIWHSSAAVFGGGTQL TVLS | P4 |
| 7 | QVQLVQSGAEVKRPGASVQVSCRASGYSINTYYMQWVRQAPGAGLEWMGVI NPSGVTSYAQKFQGRVTLTNDTSTNTVYMQLNSLTSADTAVYYCARWALWG DFGMDVWGKGTLVTVSSGGGGSGGGGSGGGGSDIQMTQSPSTLSASIGDRV TITCRASEGIYHWLAWYQQKPGKAPKLLIYKASSLASGAPSRFSGSGSGTD FTLTISSLQPDDFATYYCQQYSNYPLTFGGGTKLEIKRA | HN1 |
| 8 | QPVLTQSSSLSASPGASASLTCTLRSGINVGPYRIYWYQQKPGSPPQYLLN YKSDSDKQQGSGVPSRFSGSKDASANAGVLLISGLRSEDEADYYCMIWHSS AAVFGGGTQLTVLS | P4 VL |
| 9 | QVQLQQSGPGLVTPSQTLSLTCAISGDSVSSNSATWNWIRQSPSRGLEWLG RTYYRSKWYNDYAVSVKSRMSINPDTSKNQFSLQLNSVTPEDTAVYYCARG MMTYYYGMDVWGQGTTVTVSSGILGS | P4 VH |
| 10 | TLRSGINVGPYRIYWYQQ | P4 L1 |
| 11 | DKQQGSG | P4 L2 |
| 12 | MIWHSSAAVFGGG | P4 L3 |
| 13 | GDSVSSNSATW | P4 H1 |
| 14 | RTYYRSKWYN | P4 H2 |
| 15 | ARGMMTYYYGMDV | P4 H3 |
| 16 | DIQMTQSPSTLSASIGDRVTITCRASEGIYHWLAWYQQKPGKAPKLLIYKA SSLASGAPSRFSGSGSGTDFTLTISSLQPDDFATYYCQQYSNYPLTFGGGT KLEIKRA | HN1 VL |
| 17 | QVQLVQSGAEVKRPGASVQVSCRASGYSINTYYMQWVRQAPGAGLEWMGVI NPSGVTSYAQKFQGRVTLTNDTSTNTVYMQLNSLTSADTAVYYCARWALWG DFGMDVWGKGTLVTVSS | HN1 VH |

-continued

| SEQ ID NO | SEQUENCE | DESCRIPTION |
|---|---|---|
| 18 | EGIYHW | HN1 L1 |
| 19 | QQYSNYPLT | HN1 L3 |
| 20 | GYSINTYY | HN1 H1 |
| 21 | INPSGVT | HN1 H2 |
| 22 | ARWALWGDFGMDV | HN1 H3 |
| 23 | MGIQGGSVLFGLLLVLAVFCHSGHSLPPRTQVQLVQSGAEVKRPGASVQVS CRASGYSINTYYMQWVRQAPGAGLEWMGVINPSGVTSYAQKFQGRVTLTND TSTNTVYMQLNSLTSADTAVYYCARWALWGDFGMDVWGKGTLVTVSSGGGG SGGGGSGGGGSDIQMTQSPSTLSASIGDRVTITCRASEGIYHWLAWYQKPG KAPKLLIYKASSLASGAPSRFSGSGSGTDFTLTISSLQPDDFATYYCQQYS NYPLTFGGGTKLEIKRARTPPMILRTSEETISTVQEKQQNISPLVRERGPQ RVAAHITGTRGRSNTLSSPNSKNEKALGRKINSWESSRSGHSFLSNLHLRN GELVIHEKGFYYIYSQTYFRFQEEIKENTKNDKQMVQYIYKYTSYPDPILL MKSARNSCWSKDAEYGLYSIYQGGIFELKENDRIFVSVTNEHLIDMDHEAS FFGAFLVGRSQNISPLVRERGPQRVAAHITGTRGRSNTLSSPNSKNEKALG RKINSWESSRSGHSFLSNLHLRNGELVIHEKGFYYIYSQTYFRFQEEIKEN TKNDKQMVQYIYKYTSYPDPILLMKSARNSCWSKDAEYGLYSIYQGGIFEL KENDRIFVSVTNEHLIDMDHEASFFGAFLVGRSQNISPLVRERGPQRVAAH ITGTRGRSNTLSSPNSKNEKALGRKINSWESSRSGHSFLSNLHLRNGELVI HEKGFYYIYSQTYFRFQEEIKENTKNDKQMVQYIYKYTSYPDPILLMKSAR NSCWSKDAEYGLYSIYQGGIFELKENDRIFVSVTNEHLIDMDHEASFFGAF LVGRS | SP-HN1-TR3 |
| 24 | MGIQGGSVLFGLLLVLAVFCHSGHSLPPRTQVQLQQSGPGLVTPSQTLSLT CAISGDSVSSNSATWNWIRQSPSRGLEWLGRTYYRSKWYNDYAVSVKSRMS INPDTSKNQFSLQLNSVTPEDTAVYYCARGMMTYYYGMDVWGQTTVTVSS GILGSGGGGSGGGGSGGGGSQPVLTQSSSLSASPGASASLTCTLRSGINVG PYRIYWYQQKPGSPPQYLLNYKSDSDKQQGSGVPSRFSGSKDASANAGVLL ISGLRSEDEADYYCMIWHSSAAVFGGGTQLTVLSRTPPMILRTSEETISTV QEKQQNISPLVRERGPQRVAAHITGTRGRSNTLSSPNSKNEKALGRKINSW ESSRSGHSFLSNLHLRNGELVIHEKGFYYIYSQTYFRFQEEIKENTKNDKQ MVQYIYKYTSYPDPILLMKSARNSCWSKDAEYGLYSIYQGGIFELKENDRI FVSVTNEHLIDMDHEASFFGAFLVGRSQNISPLVRERGPQRVAAHITGTRG RSNTLSSPNSKNEKALGRKINSWESSRSGHSFLSNLHLRNGELVIHEKGFY YIYSQTYFRFQEEIKENTKNDKQMVQYIYKYTSYPDPILLMKSARNSCWSK DAEYGLYSIYQGGIFELKENDRIFVSVTNEHLIDMDHEASFFGAFLVGRSQ NISPLVRERGPQRVAAHITGTRGRSNTLSSPNSKNEKALGRKINSWESSRS GHSFLSNLHLRNGELVIHEKGFYYIYSQTYFRFQEEIKENTKNDKQMVQYI YKYTSYPDPILLMKSARNSCWSKDAEYGLYSIYQGGIFELKENDRIFVSVT NEHLIDMDHEASFFGAFLVGRS | SP-P4-TR3 |
| 25 | LPPRTQVQLVQSGAEVKRPGASVQVSCRASGYSINTYYMQWVRQAPGAGLE WMGVINPSGVTSYAQKFQGRVTLTNDTSTNTVYMQLNSLTSADTAVYYCAR WALWGDFGMDVWGKGTLVTVSSGGGGSGGGGSGGGGSDIQMTQSPSTLSAS IGDRVTITCRASEGIYHWLAWYQKPGKAPKLLIYKASSLASGAPSRFSGSG SGTDFTLTISSLQPDDFATYYCQQYSNYPLTFGGGTKLEIKRARTPPMILR TSEETISTVQEKQQNISPLVRERGPQRVAAHITGTRGRSNTLSSPNSKNEK ALGRKINSWESSRSGHSFLSNLHLRNGELVIHEKGFYYIYSQTYFRFQEEI KENTKNDKQMVQYIYKYTSYPDPILLMKSARNSCWSKDAEYGLYSIYQGGI FELKENDRIFVSVTNEHLIDMDHEASFFGAFLVGRSQNISPLVRERGPQRV AAHITGTRGRSNTLSSPNSKNEKALGRKINSWESSRSGHSFLSNLHLRNGE LVIHEKGFYYIYSQTYFRFQEEIKENTKNDKQMVQYIYKYTSYPDPILLMK SARNSCWSKDAEYGLYSIYQGGIFELKENDRIFVSVTNEHLIDMDHEASFF GAFLVGRSQNISPLVRERGPQRVAAHITGTRGRSNTLSSPNSKNEKALGRK INSWESSRSGHSFLSNLHLRNGELVIHEKGFYYIYSQTYFRFQEEIKENTK NDKQMVQYIYKYTSYPDPILLMKSARNSCWSKDAEYGLYSIYQGGIFELKE NDRIFVSVTNEHLIDMDHEASFFGAFLVGRS | HN1-TR3 |
| 26 | LPPRTQVQLQQSGPGLVTPSQTLSLTCAISGDSVSSNSATWNWIRQSPSRG LEWLGRTYYRSKWYNDYAVSVKSRMSINPDTSKNQFSLQLNSVTPEDTAVY YCARGMMTYYYGMDVWGQTTVTVSSGILGSGGGGSGGGGSGGGGSQPVLT QSSSLSASPGASASLTCTLRSGINVGPYRIYWYQQKPGSPPQYLLNYKSDS DKQQGSGVPSRFSGSKDASANAGVLLISGLRSEDEADYYCMIWHSSAAVFG GGTQLTVLSRTPPMILRTSEETISTVQEKQQNISPLVRERGPQRVAAHITG TRGRSNTLSSPNSKNEKALGRKINSWESSRSGHSFLSNLHLRNGELVIHEK GFYYIYSQTYFRFQEEIKENTKNDKQMVQYIYKYTSYPDPILLMKSARNSC WSKDAEYGLYSIYQGGIFELKENDRIFVSVTNEHLIDMDHEASFFGAFLVG RSQNISPLVRERGPQRVAAHITGTRGRSNTLSSPNSKNEKALGRKINSWES SRSGHSFLSNLHLRNGELVIHEKGFYYIYSQTYFRFQEEIKENTKNDKQMV QYIYKYTSYPDPILLMKSARNSCWSKDAEYGLYSIYQGGIFELKENDRIFV | P4-TR3 |

| SEQ ID NO | SEQUENCE | DESCRIPTION |
|---|---|---|
| | SVTNEHLIDMDHEASFFGAFLVGRSQNISPLVRERGPQRVAAHITGTRGRS NTLSSPNSKNEKALGRKINSWESSRSGHSFLSNLHLRNGELVIHEKGFYYI YSQTYFRFQEEIKENTKNDKQMVQYIYKYTSYPDPILLMKSARNSCWSKDA EYGLYSIYQGGIFELKENDRIFVSVTNEHLIDMDHEASFFGAFLVGRS | |

EXAMPLES

The following examples illustrate various iterations of the invention and are not intended to be limiting of the scope of any claim.

Example 1. Construction of a TRAIL Trimer Plasmid

Figure 4:
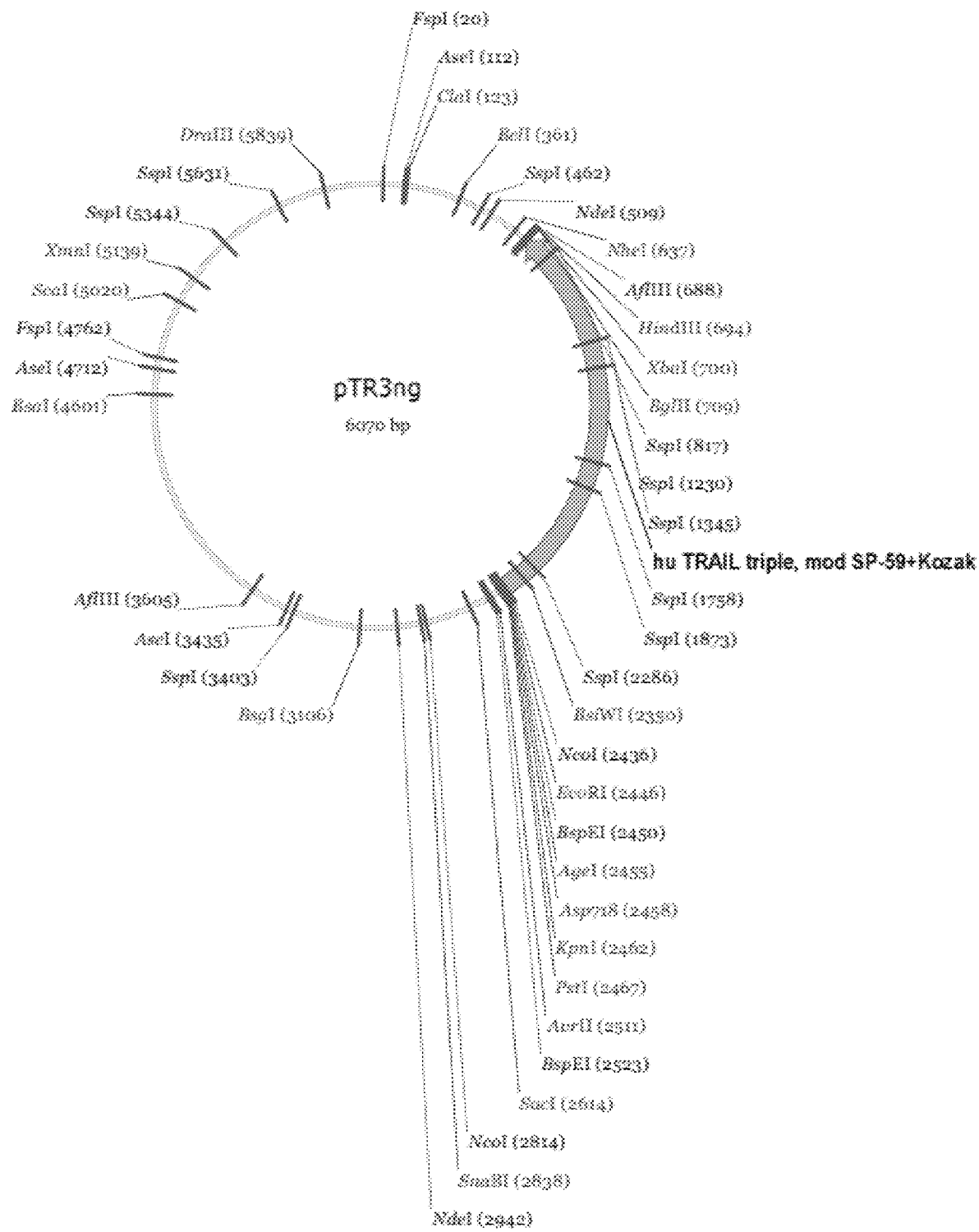
FIG. 4 shows a restriction map of plasmid pTR3.

Recombinant human TRAIL (aa 114-281, (SEQ ID NO: 1) was purchased from Enzo Life Sciences. The wild type, N-terminal ectodomain of human TRAIL (TR) described herein contains amino acids 91-281 (SEQ ID NO: 1) (domain I, compare FIG. 3 including the striped box; the white box represents aa 114-281 of rTRAIL). A 594 bp DNA fragment amplified by PCR from a human U937 cDNA library (Spitzer, D., et al., J. Immunol. 2007, 179: 2600-2608) was inserted via BsiWI (5') and HindIII (3') into sT-DAF (Spitzer, D., et al., Mol. Immunol. 2004, 40: 5 911-919). This basic TRAIL plasmid, designated pTRBgI, contains an additional BgIII site immediately upstream of TRAIL's native stop codon for subsequent cloning purposes. It also contains a signal peptide to ensure secretion of the protein. Following linearization of pTRBgI with BgIII and HindIII, the slightly smaller PCR-derived domains I' (5' BamHI and 3' HindIII), containing amino acids 108-281 of native TRAIL (SEQ ID NO: 1), were added stepwise resulting in pTR2 (intermediate) and pTR3, respectively (FIG. 4).

Example 2. Construction of a TRAIL Trimer Plasmid Further Comprising an Epitope-Binding Agent The non-targeted platform TR3 is easily accessible for further genetic modifications for targeted cancer therapy. Mesothelin targeting of TR3 can be achieved by insertion of a nucleotide sequence encoding an epitope-binding agent into the pTR3 plasmid. In this example, a nucleotide sequence of a single chain antibody fragment (scFv) was inserted into the pTR3 plasmid. To generate targeted constructs, the following cDNA sequences are custom-synthesized: 1) a 738 bp cDNA encoding for SS, an anti-mouse scFv that binds with high affinity to mesothelin (Chowdhury, et al., *PNAS.* 1998; 95(2):669-674); 2) a 795 bp fragment encoding for P4, an anti-human scFv that binds with high affinity to mesothelin (Bergan, et al., 2007, *Cancer Lett* 255: 263-274); and 3) a 732 bp fragment encoding for HN1, an anti-human scFv that binds with high affinity to mesothelin (Ho, et al., 2011, *International Journal of Cancer.* 128(9), 2020-2030). The 738 bp BsiWI scFv-SS fragment, the 795 bp BsiWI scFv-P4 fragment, or the 732 bp BsiWI scFv-HN1 fragment, is inserted into the BsiWI-linearized pTR3 plasmid to generate pSS-TR3 plasmid, pP4-TR3 plasmid, or pHN1-TR3 plasmid, respectively.

Example 3. Preparation and Confirmation of Constructs Described in Section I The pTR3, pSS-TR3, pP4-TR3, and pHN1-TR3 plasmids are transiently expressed in HEK293T cells using Opti-Mem serum-free medium (Gibco) and TransIT-293 (Mirus, MIR2700) transfection reagent, as per the manufacturer's instructions. To obtain concentrated TR3 protein stocks from harvested cells, the supernatants are applied to centrifugal filter devices with a 10 kDa molecular cut-off (Centricon Plus-20, Millipore, Bedford, MD).

Figure 5:
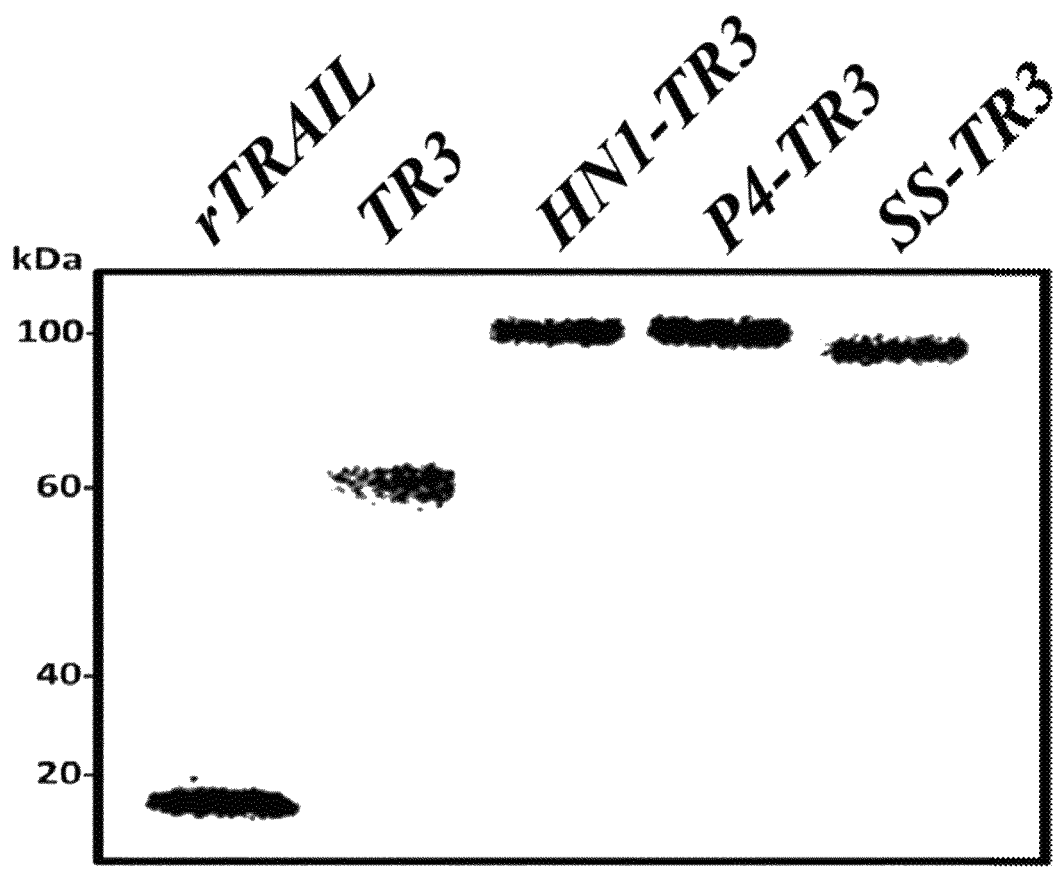
FIG. 5 shows the confirmation of the single chain character of the fusion to the TR3 drug platform in comparison to the conventional rTRAIL configuration. The single chain character of the fusion proteins are verified by Western blot analysis. Under reducing conditions, commercially available recombinant TRAIL (rTRAIL, aa 114-281) exhibits a molecular weight of 18 kDa and TR3 has a molecular weight of approximately 61 kDa, consistent with the calculated size. Insertion of single chain antibody fragments HN1, P4 and SS into TR3 increases the molecular weight of each targeted therapeutic as expected.

The single chain character of the TR3 proteins is verified by Western blot analysis. Under reducing conditions, commercially available recombinant TRAIL (rTRAIL, aa 114-281) exhibits a molecular weight of 18 kDa and TR3 has a molecular weight of approximately 61 kDa, consistent with the calculated size. Insertion of single chain antibody fragments HN1, P4 and SS into TR3 increases the molecular weight of each targeted therapeutic as expected (FIG. 5).

Figure 6:
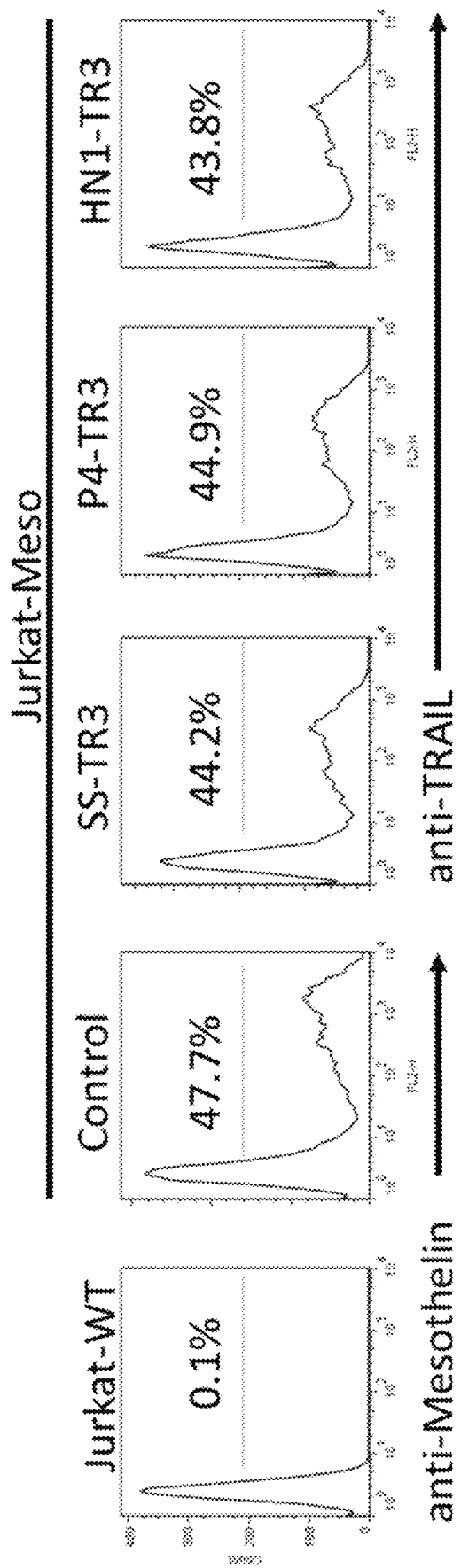
FIG. 6 shows that cells overexpressing mesothelin tether all scFv-containing TR3 variants to cell surface. Mature human mesothelin is inserted into the membrane of Jurkat cells via a glycosylphosphatidyl (GPI) anchor. Anti-mesothelin immunostaining confirms expression of human mesothelin on Jurkat-Meso cells using flow cytometry. Jurkat-Meso cells are treated with SS-TR3, P4-TR3, or HN1-TR3. Anti-TRAIL immunostaining confirms tethering of SS-TR3, P4-TR3, and HN1-TR3 to human mesothelin on Jurkat-Meso cells using flow cytometry.

Example 4. Cells Overexpressing Mesothelin Tether all scFv-Containing Constructs to Cell Surface Mature human mesothelin is inserted into the membrane of Jurkat cells via a glycosylphosphatidyl (GPI) anchor. Anti-mesothelin immunostaining confirms surface expression of human mesothelin on Jurkat-Meso cells using flow cytometry. To test the ability of scFv-containing TR3 variants to bind to cell surface human mesothelin, Jurkat-Meso cells are treated with SS-TR3, P4-TR3, or HN1-TR3. The staining pattern of anti-TRAIL immunostaining confirms the tethering of SS-TR3, P4-TR3, and HN1-TR3 to human mesothelin on Jurkat-Meso cells using flow cytometry (FIG. 6).

Figure 7A:
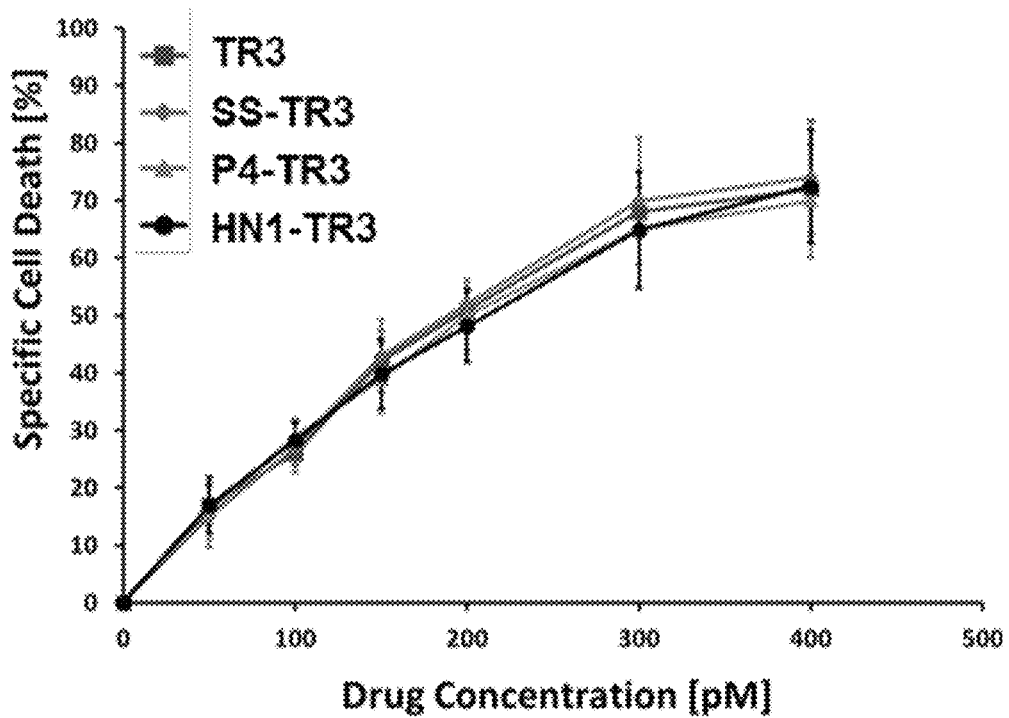
FIG. 7A-B shows that the TR3 variants SS-TR3, P4-TR3 and HN1-TR3 induce apoptosis in a mesothelin-expressing cancer model. Mesothelin-deficient Jurkat wild-type cells (FIG. 7A) and mesothelin-expressing Jurkat-Meso cells (FIG. 7B) are treated in vitro with increasing equimolar concentrations of TR3 (red) and the targeted variants SS-TR3 (green), P4-TR3 (blue) and HN1-TR3 (black). In the absence of mesothelin expression, all drugs are equally potent in cell viability assays. When mesothelin is present on the surface of the cancer cells, SS-TR3 is the most potent reagent, followed by P4-TR3 and HN1-TR3 (similar activity profiles), and TR3 is the least effective at inducing apoptosis.
Figure 7B:
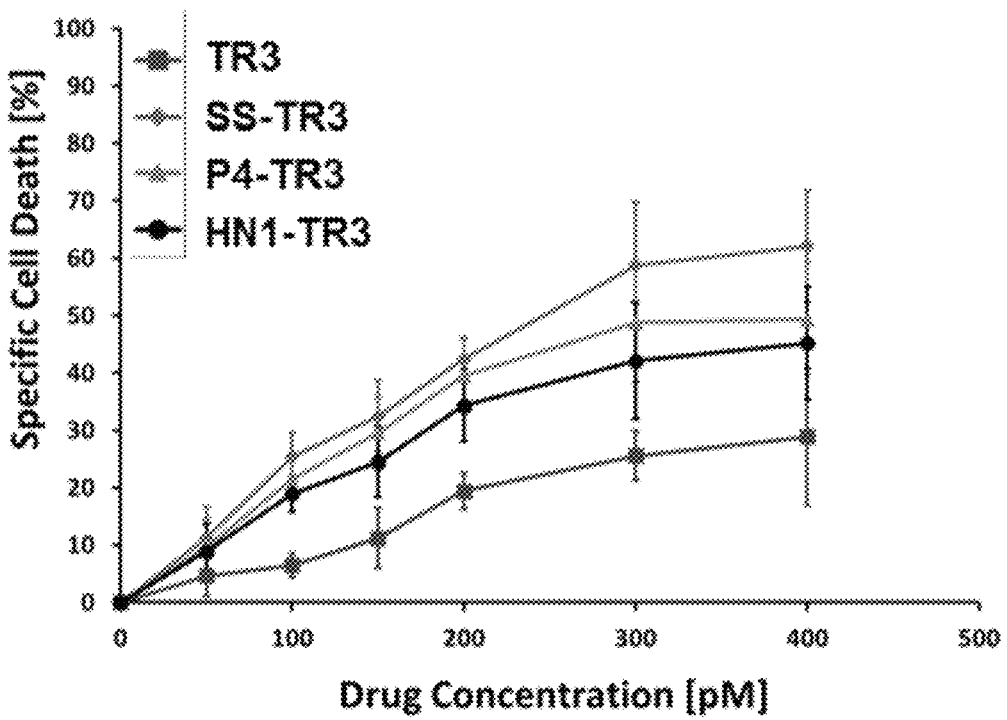

Example 5. SS-TR3, P4-TR3 and HN1-TR3 Induce Apoptosis in a Mesothelin-Expressing Cancer Model Mesothelin-deficient Jurkat wild-type cells and mesothelin-expressing Jurkat-Meso cells are treated in vitro with increasing equimolar concentrations of TR3 and the targeted variants SS-TR3, P4-TR3, and HN1-TR3. Cell viability of the treated cells was determined using the CellTiter-Glo kit (Promega) according to the manufacturer's instructions. Data are recorded with a luminescence plate reader (Molecular Devices, SpectraMAX-Gemini, SoftMax Version 5 software, Sunnyvale, California). In the absence of mesothelin expression, all constructs are equally potent in cell viability assays (FIG. 7A). When mesothelin is present on the surface of the cancer cells, SS-TR3 is the most potent, followed by P4-TR3 and HN1-TR3 (similar activity profiles), and TR3 is the least effective at inducing apoptosis (FIG. 7B).

Figure 8:
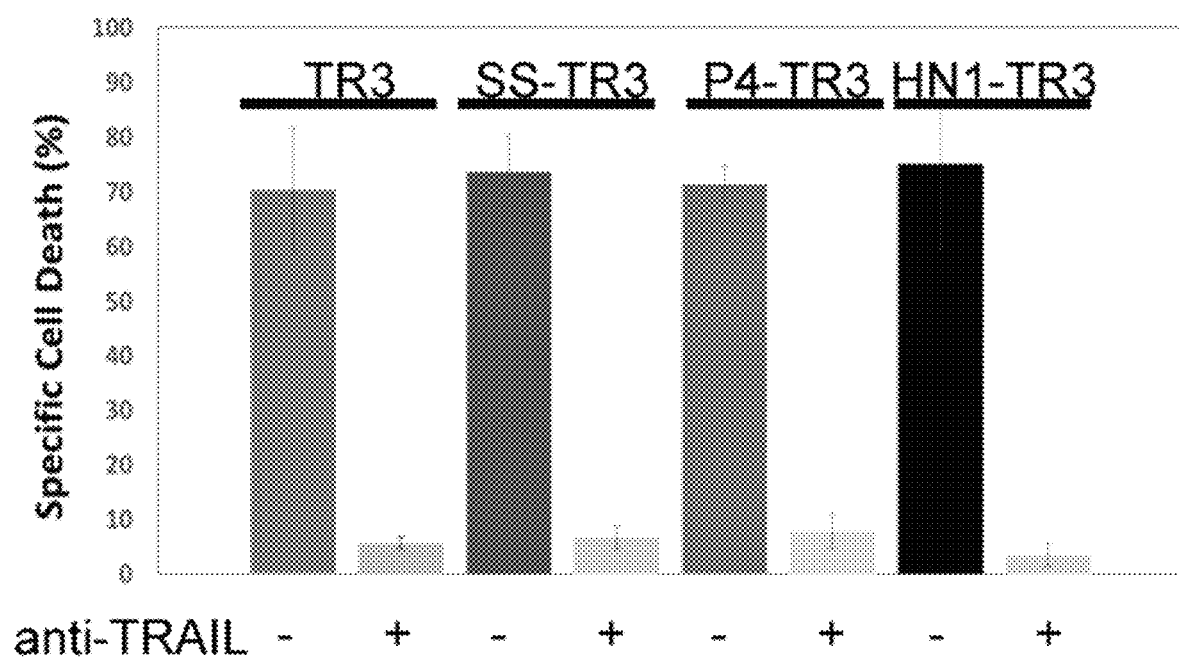
FIG. 8 shows that TR3 drug platforms engage in extrinsic death pathway via death receptor binding. Jurkat wild-type (WT) cells are treated with a constant amount of TR3, and the targeted variants SS-TR3, P4-TR3, and HN1-TR3 (70% specific cell death) in the presence of anti-TRAIL mAb, a blocker of death receptor engagement. Cells treated with DMSO are used as a control.

Example 6. The Delivery Moieties of the Targeted Biologics do not Interfere with TRAIL Death Receptor Recognition Jurkat wild-type cells are treated with a constant amount of TR3, SS-TR3, P4-TR3, and HN1-TR3 (70% specific cell death) in the presence of anti-TRAIL mAb, a blocker of death receptor engagement. Cells treated with the vehicle DMSO are used as a control. Cell viability of the treated cells was determined using the CellTiter-Glo kit (Promega) according to the manufacturer's instructions. Data are recorded with a luminescence plate reader (Molecular Devices, SpectraMAX-Gemini, SoftMax Version 5 software, Sunnyvale, California). The addition of anti-TRAIL mAb prevents cell specific death by all of the constructs (FIG. 8), indicating that the TR3 domain has unrestricted access to the death receptors expressed on the Jurkat cells.

Figure 9:
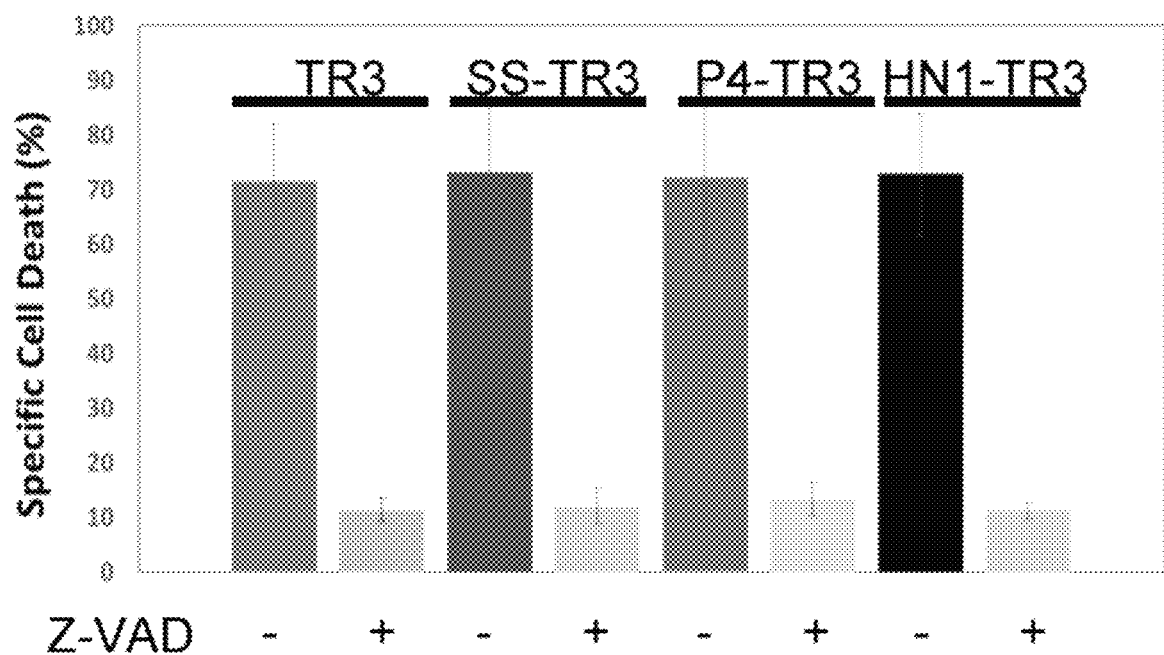
FIG. 9 shows that TR3 drug platforms engage in caspase-dependent apoptosis. Jurkat wild-type (WT) cells are treated with a constant amount of TR3, and the targeted variants SS-TR3, P4-TR3, and HN1-TR3 (70% specific cell death) in the presence of Z-VAD-FMK, a pan-caspase inhibitor to block the extrinsic death pathway. Cells treated with DMSO are used as a control.

The downstream effector of the extrinsic pathway, intracellular caspases, is blocked by using the pan-caspase inhibitor, Z-VAD-FMK (Enzo). Jurkat wild-type cells are treated with a constant amount of TR3, SS-TR3, P4-TR3, and HN1-TR3 (70% specific cell death) in the presence of Z-VAD-FMK or DMSO as a control. Cell death is completely blocked with Z-VAD-FMK, confirming that the constructs engage the extrinsic death pathway (FIG. 9).

Figure 10G:
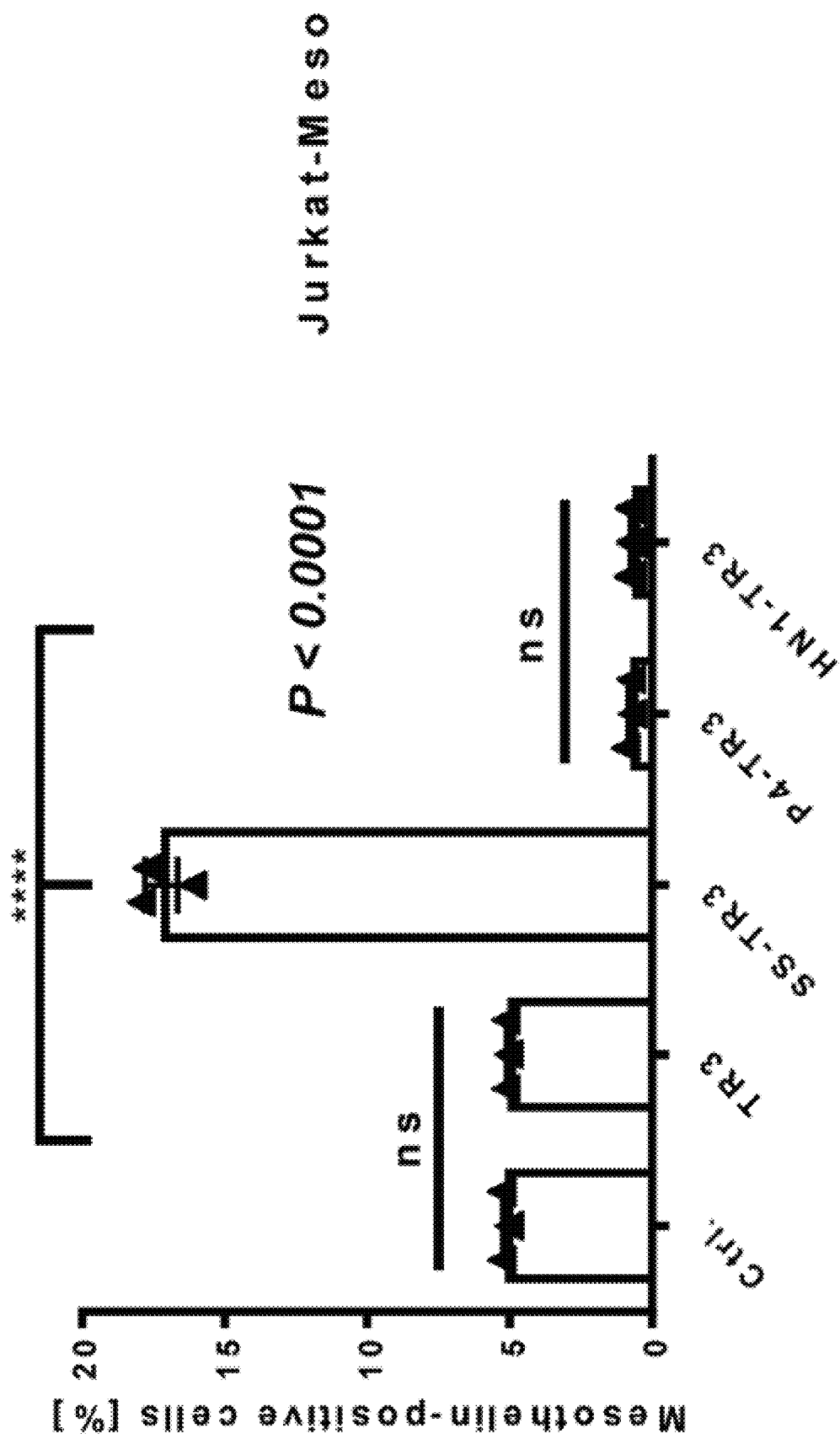

Example 7. P4-TR3 and HN1-TR3 Induce Apoptosis Via a Direct "Cis" Mechanism in a Mesothelin-Expressing Cancer Model Phenotypic characterization reveals the differential cell death mechanisms between SS-TR3 and the humanized variants P4-TR3 and HN1-TR3. SS-TR3 treatment results in a significant accumulation of cancer cells (from 5.01% to 17.7%, anti-mesothelin stain), in agreement with an established "trans" killing profile. In contrast, P4-TR3 and HN1-TR3 eliminate their cancer targets directly via a more desirable "cis" mechanism (from 5.01% to 0.92% and 0.75%, respectively) (FIG. 10).

Example 8. Treatment of Adherent Human Cancer Cells Expressing Endogenous Mesothelin with TR-3, P4-TR3, HN1-TR3 and SS-TR3

Figure 11A:
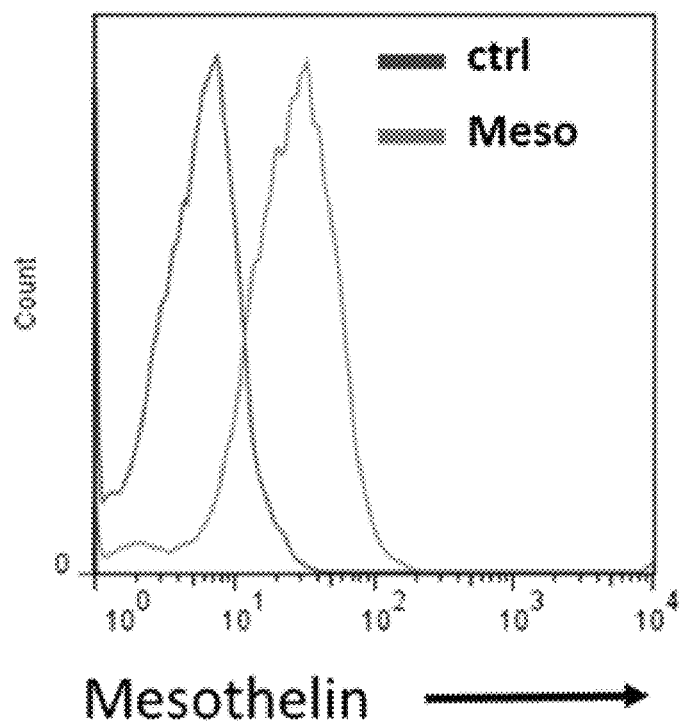
FIG. 11A-B shows treatment of adherent human ovarian cancer cells with TR3, P4-TR3, HN1-TR3 and SS-TR3. Endogenous cell-surface mesothelin expression in the ovarian cancer cell line OVCAR3 is confirmed by immunostaining with an anti-mesothelin antibody, detected by flow cytometry (FIG. 11A). OVCAR3 cells are treated with increasing concentrations of TR3, P4-TR3, HN1-TR3 or SS-TR3. After 24 hours, cell viability of drug-treated cells is determined using the CellTiter-Glo kit (Promega) (FIG. 11B).
Figure 11B:
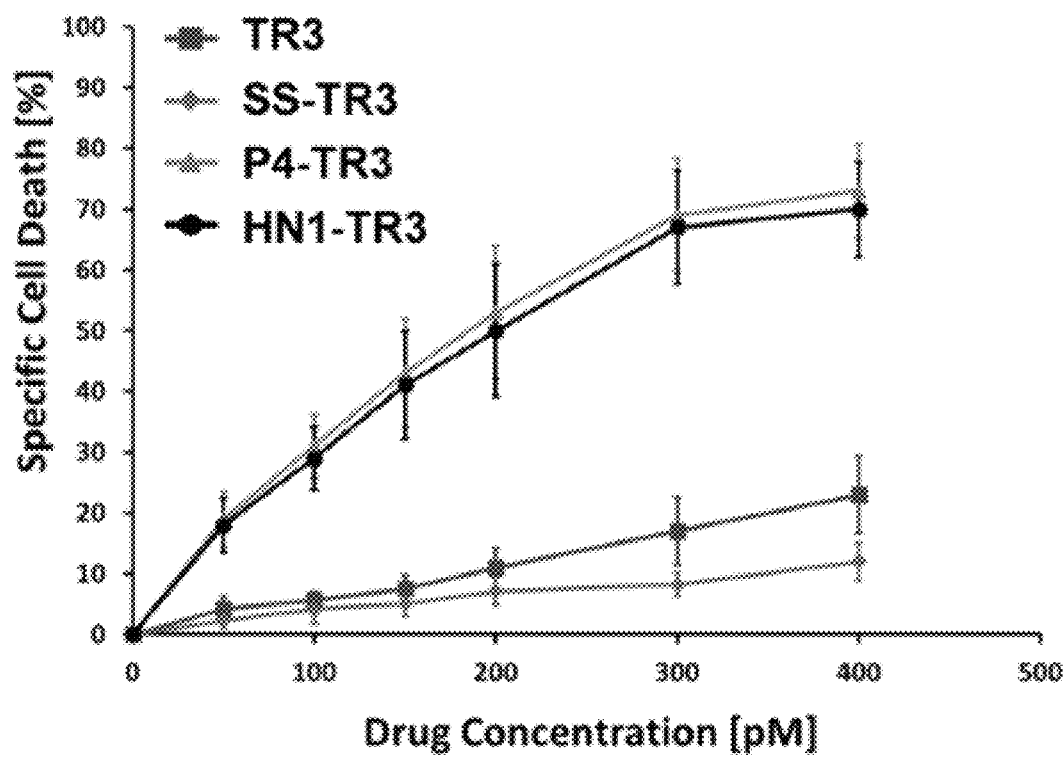
Figure 12A:
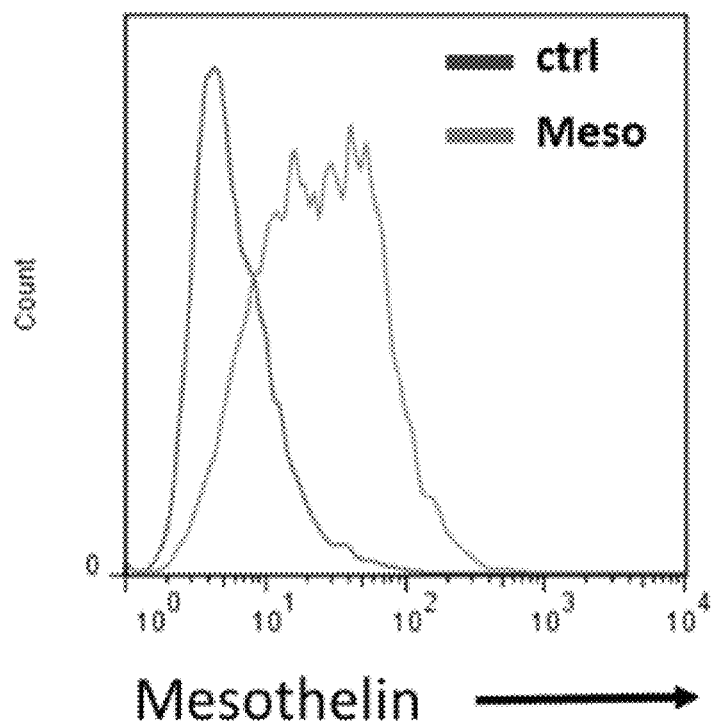
FIG. 12A-B shows treatment of adherent human pancreatic cancer cells with TR3, P4-TR3, HN1-TR3 and SS-TR3. Endogenous cell-surface mesothelin expression in the pancreatic cancer cell line BxPC-3 is confirmed by immunostaining with an anti-mesothelin antibody, detected by flow cytometry (FIG. 12A). BxPC-3 cells are treated with increasing concentrations of TR3, P4-TR3, HN1-TR3 or SS-TR3. After 24 hours, cell viability of drug-treated cells is determined using the CellTiter-Glo kit (Promega) (FIG. 12B).
Figure 12B:
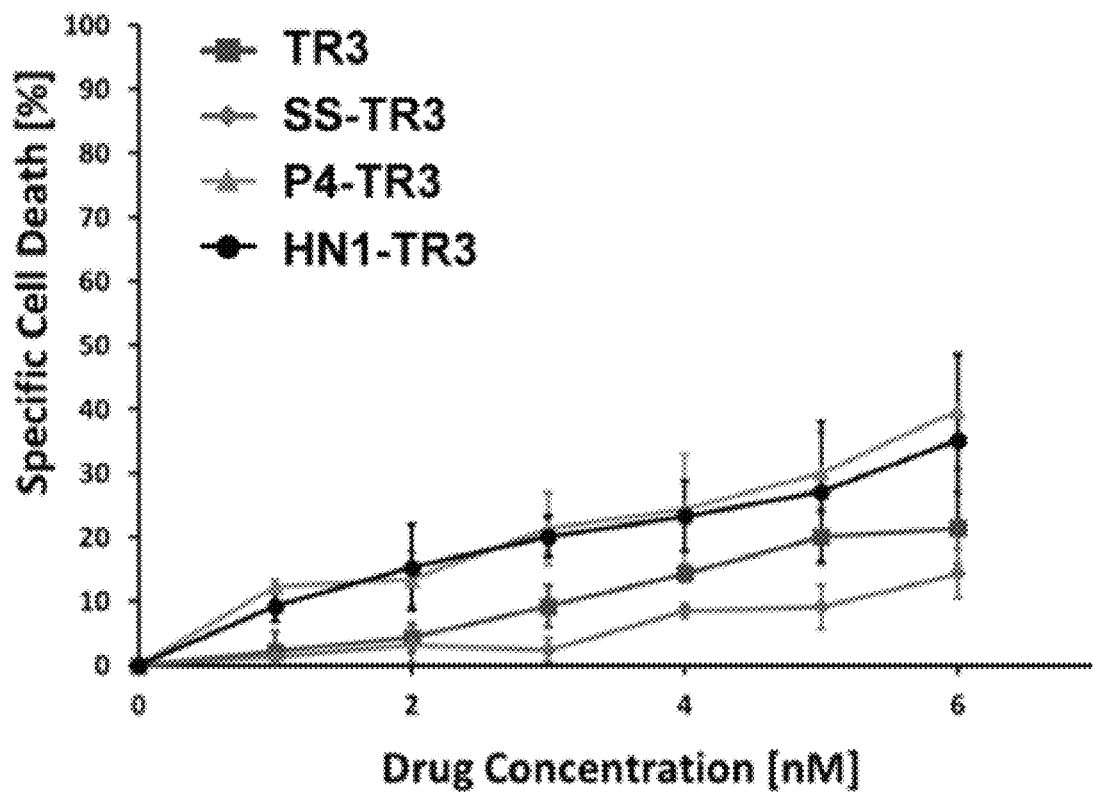
Figure 13A:
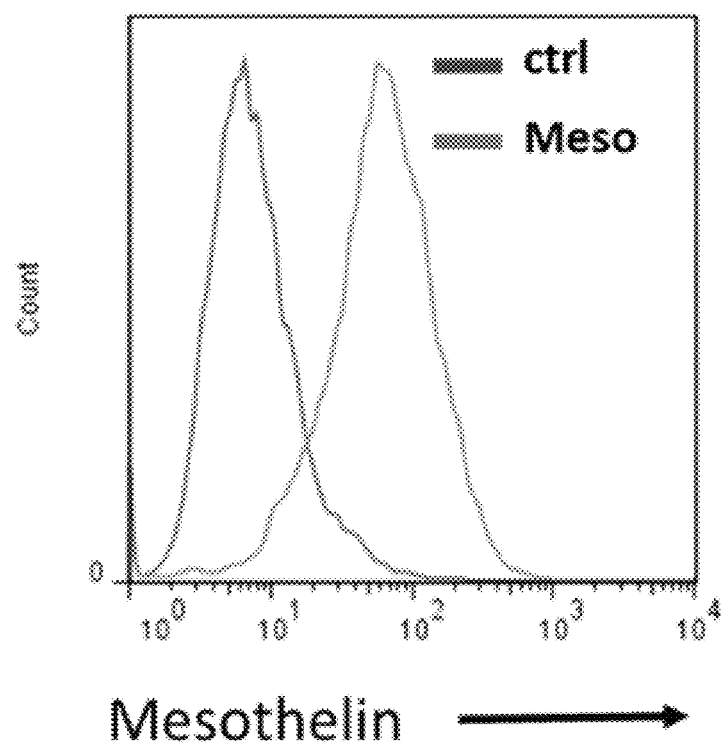
FIG. 13A-B shows treatment of adherent human pancreatic cancer cells AsPC-1 with TR3, P4-TR3, HN1-TR3 and SS-TR3. Endogenous cell-surface mesothelin expression in the pancreatic cancer cell line AsPC-1 is confirmed by immunostaining with an anti-mesothelin antibody, detected by flow cytometry (FIG. 13A). AsPC-1 cells are treated with increasing concentrations of TR-3, P4-TR3, HN1-TR3 or SS-TR3. After 24 hours, cell viability of drug-treated cells is determined using the CellTiter-Glo kit (Promega) (FIG. 13B).
Figure 13B:
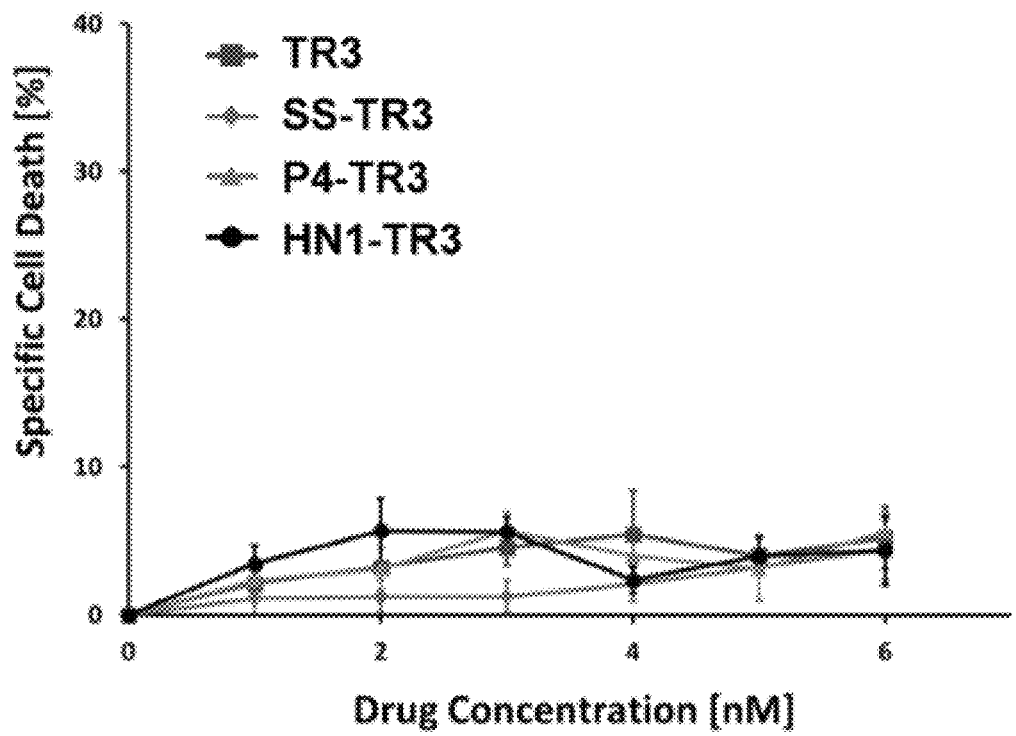

Three human, adherent cancer cell lines express endogenous mesothelin: ovarian cancer cell line OVCAR3 (FIG. 11A), pancreatic cancer cell line BxPC-3 (FIG. 12A), and adenocarcinoma cell line AsPC-1 (FIG. 13A). Each adherent cancer cell line is treated with increasing concentrations of TR-3, P4-TR3, HN1-TR3 or SS-TR3. Cell viability of the treated cells was determined using the CellTiter-Glo kit (Promega) according to the manufacturer's instructions. Data are recorded with a luminescence plate reader (Molecular Devices, SpectraMAX-Gemini, SoftMax Version 5 software, Sunnyvale, California). OVCAR3 cells treated with P4-TR3 and HN1-TR3 are readily eliminated whereas the SS-TR3 performs worse than TR3 (FIG. 11B). BxPC-3 cells demonstrated a similar profile (FIG. 12B). The data reveal the strong killing capacity of P4-TR3 and HN1-TR3, consistent with a proposed cis-killing phenotype. TR3 shows little killing capacity, while SS-TR3 is even less potent, consistent with an exclusive trans-killing phenotype. Some cancer cells are quite resistant to TRAIL therapy as seen with construct treatment of AsPC-1 cells (FIG. 13B); however, this observation indicates that AsPC-1 cells can be used to study the bystander killing properties of the constructs.

Figure 14:
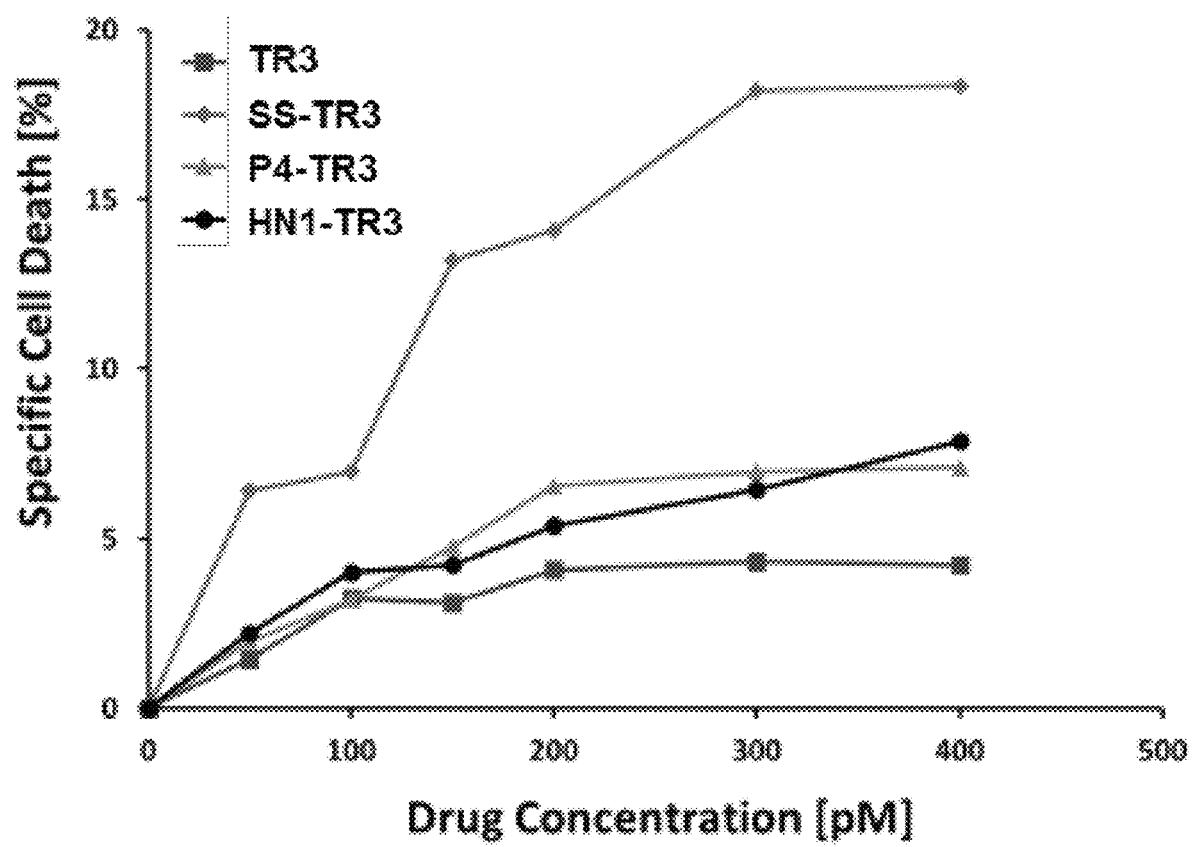
FIG. 14 shows a coculture of mesothelin-positive AsPC-1 with Jurkat bystander cells in the presence of non-targeted and targeted-TR3. TRAIL resistant, mesothelin-positive AsPC-1 pancreatic cancer cells are decorated with increasing concentrations of TR3, P4-TR3 and HN1-TR3 and SS-TR3 by incubating the cells with the TR3 constructs for 2 hours. TR3 constructs are removed by washing and decorated AsPC-1 cells are cocultured with WT Jurkat bystander cells for 24 hours. Cells are harvested and analyzed for viability.

Example 9. Coculture of Mesothelin-Positive AsPC-1 with Jurkat Bystander Cells in the Presence of Section I Constructs TRAIL resistant, mesothelin-positive AsPC-1 pancreatic cancer cells decorated with increasing concentrations of TR-3, P4-TR3 and HN1-TR3 and SS-TR3, washed in order to eliminate traces of the soluble constructs and are subsequently cocultured with WT Jurkat bystander cells for 24 hours. Cells are next analyzed for viability. SS-TR3-decorated AsPC-1 cells cultured in the presence of wild-type Jurkat cells leads to substantial cell death induction of the Jurkat bystander cells; however, P4-TR3- and HN1-TR3-decorated AsPC-1 cells have only a very limited ability to induce Jurkat bystander cell killing, similar to TR3 alone (FIG. 14). These data confirm the inability of SS-TR3 to kill mesothelin-positive cancer cells directly via a cis mechanism but is very much capable of killing bystander Jurkat cells via a trans mechanism. P4-TR3 and HN1-TR3 nearly exclusively kill via a cis mechanism and are nearly incapable to induce bystander killing (no trans killing).

What is claimed is:

1. A construct comprising the amino acid sequence set forth in SEQ ID NO: 25 or 26.

2. A method of inducing apoptosis in a tumor cell that expresses cell surface human mesothelin and either DR4 or DR5, comprising contacting the tumor cell with the construct of claim 1 or transducing a cell with a DNA virus or an RNA virus encoding the construct of claim 1.

3. A method of treating a cancer in a subject in need thereof, wherein cells of the cancer express cell surface human mesothelin and either DR4 or DR5, the method comprising administering to the subject the construct of claim 1 or a DNA or an RNA virus encoding the construct of claim 1.

4. The method of claim 3, wherein the cancer is selected from the group consisting of mesothelioma, papillary serous ovarian adenocarcinoma, clear cell ovarian carcinoma, mixed Mullerian ovarian carcinoma, endometroid mucinous ovarian carcinoma, pancreatic adenocarcinoma, ductal pancreatic adenocarcinoma, uterine serous carcinoma, lung adenocarcinoma, extrahepatic bile duct carcinoma, gastric adenocarcinoma, esophageal adenocarcinoma, colorectal adenocarcinoma, and breast adenocarcinoma.

* * * * *

SEQUENCE LISTING

```
<160> NUMBER OF SEQ ID NOS: 26

<210> SEQ ID NO 1
<211> LENGTH: 281
<212> TYPE: PRT
<213> ORGANISM: Homo sapiens

<400> SEQUENCE: 1

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95
```

```
Glu Glu Thr Ile Ser Thr Val Gln Glu Lys Gln Gln Asn Ile Ser Pro
            100                 105                 110
Leu Val Arg Glu Arg Gly Pro Gln Arg Val Ala Ala His Ile Thr Gly
        115                 120                 125
Thr Arg Gly Arg Ser Asn Thr Leu Ser Ser Pro Asn Ser Lys Asn Glu
130                 135                 140
Lys Ala Leu Gly Arg Lys Ile Asn Ser Trp Glu Ser Ser Arg Ser Gly
145                 150                 155                 160
His Ser Phe Leu Ser Asn Leu His Leu Arg Asn Gly Glu Leu Val Ile
                165                 170                 175
His Glu Lys Gly Phe Tyr Tyr Ile Tyr Ser Gln Thr Tyr Phe Arg Phe
            180                 185                 190
Gln Glu Glu Ile Lys Glu Asn Thr Lys Asn Asp Lys Gln Met Val Gln
        195                 200                 205
Tyr Ile Tyr Lys Tyr Thr Ser Tyr Pro Asp Pro Ile Leu Leu Met Lys
210                 215                 220
Ser Ala Arg Asn Ser Cys Trp Ser Lys Asp Ala Glu Tyr Gly Leu Tyr
225                 230                 235                 240
Ser Ile Tyr Gln Gly Gly Ile Phe Glu Leu Lys Glu Asn Asp Arg Ile
                245                 250                 255
Phe Val Ser Val Thr Asn Glu His Leu Ile Asp Met Asp His Glu Ala
            260                 265                 270
Ser Phe Phe Gly Ala Phe Leu Val Gly
        275                 280

<210> SEQ ID NO 2
<211> LENGTH: 552
<212> TYPE: PRT
<213> ORGANISM: Artificial Sequence
<220> FEATURE:
<223> OTHER INFORMATION: SYNTHESIZED

<400> SEQUENCE: 2

Leu Pro Pro Arg Thr Pro Pro Met Ile Leu Arg Thr Ser Glu Glu Thr
1               5                   10                  15
Ile Ser Thr Val Gln Glu Lys Gln Gln Asn Ile Ser Pro Leu Val Arg
            20                  25                  30
Glu Arg Gly Pro Gln Arg Val Ala Ala His Ile Thr Gly Thr Arg Gly
        35                  40                  45
Arg Ser Asn Thr Leu Ser Ser Pro Asn Ser Lys Asn Glu Lys Ala Leu
50                  55                  60
Gly Arg Lys Ile Asn Ser Trp Glu Ser Ser Arg Ser Gly His Ser Phe
65                  70                  75                  80
Leu Ser Asn Leu His Leu Arg Asn Gly Glu Leu Val Ile His Glu Lys
                85                  90                  95
Gly Phe Tyr Tyr Ile Tyr Ser Gln Thr Tyr Phe Arg Phe Gln Glu Glu
            100                 105                 110
Ile Lys Glu Asn Thr Lys Asn Asp Lys Gln Met Val Gln Tyr Ile Tyr
        115                 120                 125
Lys Tyr Thr Ser Tyr Pro Asp Pro Ile Leu Leu Met Lys Ser Ala Arg
130                 135                 140
Asn Ser Cys Trp Ser Lys Asp Ala Glu Tyr Gly Leu Tyr Ser Ile Tyr
145                 150                 155                 160
Gln Gly Gly Ile Phe Glu Leu Lys Glu Asn Asp Arg Ile Phe Val Ser
                165                 170                 175
```

Val Thr Asn Glu His Leu Ile Asp Met Asp His Glu Ala Ser Phe Phe
            180                 185                 190

Gly Ala Phe Leu Val Gly Arg Ser Gln Asn Ile Ser Pro Leu Val Arg
            195                 200                 205

Glu Arg Gly Pro Gln Arg Val Ala Ala His Ile Thr Gly Thr Arg Gly
210                 215                 220

Arg Ser Asn Thr Leu Ser Ser Pro Asn Ser Lys Asn Glu Lys Ala Leu
225                 230                 235                 240

Gly Arg Lys Ile Asn Ser Trp Glu Ser Ser Arg Ser Gly His Ser Phe
            245                 250                 255

Leu Ser Asn Leu His Leu Arg Asn Gly Glu Leu Val Ile His Glu Lys
            260                 265                 270

Gly Phe Tyr Tyr Ile Tyr Ser Gln Thr Tyr Phe Arg Phe Gln Glu Glu
            275                 280                 285

Ile Lys Glu Asn Thr Lys Asn Asp Lys Gln Met Val Gln Tyr Ile Tyr
            290                 295                 300

Lys Tyr Thr Ser Tyr Pro Asp Pro Ile Leu Leu Met Lys Ser Ala Arg
305                 310                 315                 320

Asn Ser Cys Trp Ser Lys Asp Ala Glu Tyr Gly Leu Tyr Ser Ile Tyr
            325                 330                 335

Gln Gly Gly Ile Phe Glu Leu Lys Glu Asn Asp Arg Ile Phe Val Ser
            340                 345                 350

Val Thr Asn Glu His Leu Ile Asp Met Asp His Glu Ala Ser Phe Phe
            355                 360                 365

Gly Ala Phe Leu Val Gly Arg Ser Gln Asn Ile Ser Pro Leu Val Arg
            370                 375                 380

Glu Arg Gly Pro Gln Arg Val Ala Ala His Ile Thr Gly Thr Arg Gly
385                 390                 395                 400

Arg Ser Asn Thr Leu Ser Ser Pro Asn Ser Lys Asn Glu Lys Ala Leu
            405                 410                 415

Gly Arg Lys Ile Asn Ser Trp Glu Ser Ser Arg Ser Gly His Ser Phe
            420                 425                 430

Leu Ser Asn Leu His Leu Arg Asn Gly Glu Leu Val Ile His Glu Lys
            435                 440                 445

Gly Phe Tyr Tyr Ile Tyr Ser Gln Thr Tyr Phe Arg Phe Gln Glu Glu
            450                 455                 460

Ile Lys Glu Asn Thr Lys Asn Asp Lys Gln Met Val Gln Tyr Ile Tyr
465                 470                 475                 480

Lys Tyr Thr Ser Tyr Pro Asp Pro Ile Leu Leu Met Lys Ser Ala Arg
            485                 490                 495

Asn Ser Cys Trp Ser Lys Asp Ala Glu Tyr Gly Leu Tyr Ser Ile Tyr
            500                 505                 510

Gln Gly Gly Ile Phe Glu Leu Lys Glu Asn Asp Arg Ile Phe Val Ser
            515                 520                 525

Val Thr Asn Glu His Leu Ile Asp Met Asp His Glu Ala Ser Phe Phe
            530                 535                 540

Gly Ala Phe Leu Val Gly Arg Ser
545                 550

<210> SEQ ID NO 3
<211> LENGTH: 577
<212> TYPE: PRT
<213> ORGANISM: Artificial Sequence
<220> FEATURE:

<223> OTHER INFORMATION: SYNTHESIZED

<400> SEQUENCE: 3

```
Met Gly Ile Gln Gly Gly Ser Val Leu Phe Gly Leu Leu Leu Val Leu
1               5                   10                  15

Ala Val Phe Cys His Ser Gly His Ser Leu Pro Pro Arg Thr Pro Pro
            20                  25                  30

Met Ile Leu Arg Thr Ser Glu Glu Thr Ile Ser Thr Val Gln Glu Lys
        35                  40                  45

Gln Gln Asn Ile Ser Pro Leu Val Arg Glu Arg Gly Pro Gln Arg Val
    50                  55                  60

Ala Ala His Ile Thr Gly Thr Arg Gly Arg Ser Asn Thr Leu Ser Ser
65                  70                  75                  80

Pro Asn Ser Lys Asn Glu Lys Ala Leu Gly Arg Lys Ile Asn Ser Trp
                85                  90                  95

Glu Ser Ser Arg Ser Gly His Ser Phe Leu Ser Asn Leu His Leu Arg
            100                 105                 110

Asn Gly Glu Leu Val Ile His Glu Lys Gly Phe Tyr Tyr Ile Tyr Ser
        115                 120                 125

Gln Thr Tyr Phe Arg Phe Gln Glu Glu Ile Lys Glu Asn Thr Lys Asn
    130                 135                 140

Asp Lys Gln Met Val Gln Tyr Ile Tyr Lys Tyr Thr Ser Tyr Pro Asp
145                 150                 155                 160

Pro Ile Leu Leu Met Lys Ser Ala Arg Asn Ser Cys Trp Ser Lys Asp
                165                 170                 175

Ala Glu Tyr Gly Leu Tyr Ser Ile Tyr Gln Gly Gly Ile Phe Glu Leu
            180                 185                 190

Lys Glu Asn Asp Arg Ile Phe Val Ser Val Thr Asn Glu His Leu Ile
        195                 200                 205

Asp Met Asp His Glu Ala Ser Phe Phe Gly Ala Phe Leu Val Gly Arg
    210                 215                 220

Ser Gln Asn Ile Ser Pro Leu Val Arg Glu Arg Gly Pro Gln Arg Val
225                 230                 235                 240

Ala Ala His Ile Thr Gly Thr Arg Gly Arg Ser Asn Thr Leu Ser Ser
                245                 250                 255

Pro Asn Ser Lys Asn Glu Lys Ala Leu Gly Arg Lys Ile Asn Ser Trp
            260                 265                 270

Glu Ser Ser Arg Ser Gly His Ser Phe Leu Ser Asn Leu His Leu Arg
        275                 280                 285

Asn Gly Glu Leu Val Ile His Glu Lys Gly Phe Tyr Tyr Ile Tyr Ser
    290                 295                 300

Gln Thr Tyr Phe Arg Phe Gln Glu Glu Ile Lys Glu Asn Thr Lys Asn
305                 310                 315                 320

Asp Lys Gln Met Val Gln Tyr Ile Tyr Lys Tyr Thr Ser Tyr Pro Asp
                325                 330                 335

Pro Ile Leu Leu Met Lys Ser Ala Arg Asn Ser Cys Trp Ser Lys Asp
            340                 345                 350

Ala Glu Tyr Gly Leu Tyr Ser Ile Tyr Gln Gly Gly Ile Phe Glu Leu
        355                 360                 365

Lys Glu Asn Asp Arg Ile Phe Val Ser Val Thr Asn Glu His Leu Ile
    370                 375                 380

Asp Met Asp His Glu Ala Ser Phe Phe Gly Ala Phe Leu Val Gly Arg
385                 390                 395                 400
```

```
Ser Gln Asn Ile Ser Pro Leu Val Arg Glu Arg Gly Pro Gln Arg Val
                405                 410                 415

Ala Ala His Ile Thr Gly Thr Arg Gly Arg Ser Asn Thr Leu Ser Ser
            420                 425                 430

Pro Asn Ser Lys Asn Glu Lys Ala Leu Gly Arg Lys Ile Asn Ser Trp
        435                 440                 445

Glu Ser Ser Arg Ser Gly His Ser Phe Leu Ser Asn Leu His Leu Arg
    450                 455                 460

Asn Gly Glu Leu Val Ile His Glu Lys Gly Phe Tyr Ile Tyr Ser
465                 470                 475                 480

Gln Thr Tyr Phe Arg Phe Gln Glu Glu Ile Lys Glu Asn Thr Lys Asn
                485                 490                 495

Asp Lys Gln Met Val Gln Tyr Ile Tyr Lys Tyr Thr Ser Tyr Pro Asp
            500                 505                 510

Pro Ile Leu Leu Met Lys Ser Ala Arg Asn Ser Cys Trp Ser Lys Asp
        515                 520                 525

Ala Glu Tyr Gly Leu Tyr Ser Ile Tyr Gln Gly Gly Ile Phe Glu Leu
    530                 535                 540

Lys Glu Asn Asp Arg Ile Phe Val Ser Val Thr Asn Glu His Leu Ile
545                 550                 555                 560

Asp Met Asp His Glu Ala Ser Phe Phe Gly Ala Phe Leu Val Gly Arg
                565                 570                 575

Ser

<210> SEQ ID NO 4
<211> LENGTH: 327
<212> TYPE: PRT
<213> ORGANISM: Artificial Sequence
<220> FEATURE:
<223> OTHER INFORMATION: SYNTHESIZED

<400> SEQUENCE: 4

Glu Val Glu Lys Thr Ala Cys Pro Ser Gly Lys Lys Ala Pro Glu Ile
1               5                   10                  15

Asp Glu Ser Leu Ile Phe Tyr Lys Lys Trp Glu Leu Glu Ala Cys Val
                20                  25                  30

Asp Ala Ala Leu Leu Ala Thr Gln Met Asp Arg Val Asn Ala Ile Pro
            35                  40                  45

Phe Thr Tyr Glu Gln Leu Asp Val Leu Lys His Lys Leu Asp Glu Leu
        50                  55                  60

Tyr Pro Gln Gly Tyr Pro Glu Ser Val Ile Gln His Leu Gly Tyr Leu
65                  70                  75                  80

Phe Leu Lys Met Ser Pro Glu Asp Ile Arg Lys Trp Asn Val Thr Ser
                85                  90                  95

Leu Glu Thr Leu Lys Ala Leu Leu Glu Val Asn Lys Gly His Glu Met
            100                 105                 110

Ser Pro Gln Val Ala Thr Leu Ile Asp Arg Phe Val Lys Gly Arg Gly
        115                 120                 125

Gln Leu Asp Lys Asp Thr Leu Asp Thr Leu Thr Ala Phe Tyr Pro Gly
    130                 135                 140

Tyr Leu Cys Ser Leu Ser Pro Glu Glu Leu Ser Ser Val Pro Pro Ser
145                 150                 155                 160

Ser Ile Trp Ala Val Arg Pro Gln Asp Leu Asp Thr Cys Asp Pro Arg
                165                 170                 175

Gln Leu Asp Val Leu Tyr Pro Lys Ala Arg Leu Ala Phe Gln Asn Met
```

```
                180                 185                 190
Asn Gly Ser Glu Tyr Phe Val Lys Ile Gln Ser Phe Leu Gly Gly Ala
            195                 200                 205
Pro Thr Glu Asp Leu Lys Ala Leu Ser Gln Gln Asn Val Ser Met Asp
        210                 215                 220
Leu Ala Thr Phe Met Lys Leu Arg Thr Asp Ala Val Leu Pro Leu Thr
225                 230                 235                 240
Val Ala Glu Val Gln Lys Leu Leu Gly Pro His Val Glu Gly Leu Lys
                245                 250                 255
Ala Glu Glu Arg His Arg Pro Val Arg Asp Trp Ile Leu Arg Gln Arg
            260                 265                 270
Gln Asp Asp Leu Asp Thr Leu Gly Leu Gly Leu Gln Gly Gly Ile Pro
        275                 280                 285
Asn Gly Tyr Leu Val Leu Asp Leu Ser Met Gln Glu Ala Leu Ser Gly
            290                 295                 300
Thr Pro Cys Leu Leu Gly Pro Gly Pro Val Leu Thr Val Leu Ala Leu
305                 310                 315                 320
Leu Leu Ala Ser Thr Leu Ala
                325

<210> SEQ ID NO 5
<211> LENGTH: 242
<212> TYPE: PRT
<213> ORGANISM: Artificial Sequence
<220> FEATURE:
<223> OTHER INFORMATION: SYNTHESIZED

<400> SEQUENCE: 5

Gln Val Gln Leu Gln Gln Ser Gly Pro Glu Leu Glu Lys Pro Gly Ala
1               5                   10                  15
Ser Val Lys Ile Ser Cys Lys Ala Ser Gly Tyr Ser Phe Thr Gly Tyr
            20                  25                  30
Thr Met Asn Trp Val Lys Gln Ser His Gly Lys Ser Leu Glu Trp Ile
        35                  40                  45
Gly Leu Ile Thr Pro Tyr Asn Gly Ala Ser Ser Tyr Asn Gln Lys Phe
    50                  55                  60
Arg Gly Lys Ala Thr Leu Thr Val Asp Lys Ser Ser Thr Ala Tyr
65              70                  75                  80
Met Asp Leu Leu Ser Leu Thr Ser Glu Asp Ser Ala Val Tyr Phe Cys
                85                  90                  95
Ala Arg Gly Gly Tyr Asp Gly Arg Gly Phe Asp Tyr Trp Gly Gln Gly
            100                 105                 110
Thr Thr Val Thr Val Ser Ser Gly Val Gly Gly Ser Gly Gly Gly Gly
        115                 120                 125
Ser Gly Gly Gly Gly Ser Asp Ile Glu Leu Thr Gln Ser Pro Ala Ile
    130                 135                 140
Met Ser Ala Ser Pro Gly Glu Lys Val Thr Met Thr Cys Ser Ala Ser
145                 150                 155                 160
Ser Ser Val Ser Tyr Met His Trp Tyr Gln Gln Lys Ser Gly Thr Ser
                165                 170                 175
Pro Lys Arg Trp Ile Tyr Asp Thr Ser Lys Leu Ala Ser Gly Val Pro
            180                 185                 190
Gly Arg Phe Ser Gly Ser Gly Ser Gly Asn Ser Tyr Ser Leu Thr Ile
        195                 200                 205
Ser Ser Val Glu Ala Glu Asp Asp Ala Thr Tyr Tyr Cys Gln Gln Trp
```

-continued

```
                210                 215                 220
Ser Gly Tyr Pro Leu Thr Phe Gly Ala Gly Thr Lys Leu Glu Ile Lys
225                 230                 235                 240

Arg Ala

<210> SEQ ID NO 6
<211> LENGTH: 259
<212> TYPE: PRT
<213> ORGANISM: Artificial Sequence
<220> FEATURE:
<223> OTHER INFORMATION: SYNTHESIZED

<400> SEQUENCE: 6

Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
                20                  25                  30

Ser Ala Thr Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Gly Met Asp Val
            100                 105                 110

Trp Gly Gln Gly Thr Thr Val Thr Val Ser Ser Gly Ile Leu Gly Ser
    115                 120                 125

Gly Gly Gly Gly Ser Gly Gly Gly Ser Gly Gly Gly Gly Ser Gln
            130                 135                 140

Pro Val Leu Thr Gln Ser Ser Ser Leu Ser Ala Ser Pro Gly Ala Ser
145                 150                 155                 160

Ala Ser Leu Thr Cys Thr Leu Arg Ser Gly Ile Asn Val Gly Pro Tyr
                165                 170                 175

Arg Ile Tyr Trp Tyr Gln Gln Lys Pro Gly Ser Pro Pro Gln Tyr Leu
            180                 185                 190

Leu Asn Tyr Lys Ser Asp Ser Asp Lys Gln Gln Gly Ser Gly Val Pro
    195                 200                 205

Ser Arg Phe Ser Gly Ser Lys Asp Ala Ser Ala Asn Ala Gly Val Leu
    210                 215                 220

Leu Ile Ser Gly Leu Arg Ser Glu Asp Glu Ala Asp Tyr Tyr Cys Met
225                 230                 235                 240

Ile Trp His Ser Ser Ala Ala Val Phe Gly Gly Gly Thr Gln Leu Thr
                245                 250                 255

Val Leu Ser

<210> SEQ ID NO 7
<211> LENGTH: 243
<212> TYPE: PRT
<213> ORGANISM: Artificial Sequence
<220> FEATURE:
<223> OTHER INFORMATION: SYNTHESIZED

<400> SEQUENCE: 7

Gln Val Gln Leu Val Gln Ser Gly Ala Glu Val Lys Arg Pro Gly Ala
1               5                   10                  15
```

Ser Val Gln Val Ser Cys Arg Ala Ser Gly Tyr Ser Ile Asn Thr Tyr
            20                  25                  30

Tyr Met Gln Trp Val Arg Gln Ala Pro Gly Ala Gly Leu Glu Trp Met
        35                  40                  45

Gly Val Ile Asn Pro Ser Gly Val Thr Ser Tyr Ala Gln Lys Phe Gln
50                  55                  60

Gly Arg Val Thr Leu Thr Asn Asp Thr Ser Asn Thr Val Tyr Met
65                  70                  75                  80

Gln Leu Asn Ser Leu Thr Ser Ala Asp Thr Ala Val Tyr Tyr Cys Ala
                85                  90                  95

Arg Trp Ala Leu Trp Gly Asp Phe Gly Met Asp Val Trp Gly Lys Gly
            100                 105                 110

Thr Leu Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Thr
130                 135                 140

Leu Ser Ala Ser Ile Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Ala
            180                 185                 190

Pro Ser Arg Phe Ser Gly Ser Gly Ser Gly Thr Asp Phe Thr Leu Thr
        195                 200                 205

Ile Ser Ser Leu Gln Pro Asp Asp Phe Ala Thr Tyr Tyr Cys Gln Gln
210                 215                 220

Tyr Ser Asn Tyr Pro Leu Thr Phe Gly Gly Gly Thr Lys Leu Glu Ile
225                 230                 235                 240

Lys Arg Ala

<210> SEQ ID NO 8
<211> LENGTH: 116
<212> TYPE: PRT
<213> ORGANISM: Artificial Sequence
<220> FEATURE:
<223> OTHER INFORMATION: SYNTHESIZED

<400> SEQUENCE: 8

Gln Pro Val Leu Thr Gln Ser Ser Leu Ser Ala Ser Pro Gly Ala
1               5                   10                  15

Ser Ala Ser Leu Thr Cys Thr Leu Arg Ser Gly Ile Asn Val Gly Pro
            20                  25                  30

Tyr Arg Ile Tyr Trp Tyr Gln Gln Lys Pro Gly Ser Pro Pro Gln Tyr
        35                  40                  45

Leu Leu Asn Tyr Lys Ser Asp Ser Asp Lys Gln Gln Gly Ser Gly Val
50                  55                  60

Pro Ser Arg Phe Ser Gly Ser Lys Asp Ala Ser Ala Asn Ala Gly Val
65                  70                  75                  80

Leu Leu Ile Ser Gly Leu Arg Ser Glu Asp Glu Ala Asp Tyr Tyr Cys
                85                  90                  95

Met Ile Trp His Ser Ser Ala Ala Val Phe Gly Gly Gly Thr Gln Leu
            100                 105                 110

Thr Val Leu Ser
        115

<210> SEQ ID NO 9
<211> LENGTH: 128
<212> TYPE: PRT
<213> ORGANISM: Artificial Sequence
<220> FEATURE:
<223> OTHER INFORMATION: SYNTHESIZED

<400> SEQUENCE: 9

Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Gly Met Asp Val
            100                 105                 110

Trp Gly Gln Gly Thr Thr Val Thr Val Ser Ser Gly Ile Leu Gly Ser
        115                 120                 125

<210> SEQ ID NO 10
<211> LENGTH: 18
<212> TYPE: PRT
<213> ORGANISM: Artificial Sequence
<220> FEATURE:
<223> OTHER INFORMATION: SYNTHESIZED

<400> SEQUENCE: 10

Thr Leu Arg Ser Gly Ile Asn Val Gly Pro Tyr Arg Ile Tyr Trp Tyr
1               5                   10                  15

Gln Gln

<210> SEQ ID NO 11
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 11

Asp Lys Gln Gln Gly Ser Gly
1               5

<210> SEQ ID NO 12
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 12

Met Ile Trp His Ser Ser Ala Ala Val Phe Gly Gly Gly
1               5                   10

<210> SEQ ID NO 13
<211> LENGTH: 11
<212> TYPE: PRT

```
<213> ORGANISM: Artificial Sequence
<220> FEATURE:
<223> OTHER INFORMATION: SYNTHESIZED

<400> SEQUENCE: 13

Gly Asp Ser Val Ser Ser Asn Ser Ala Thr Trp
1               5                   10

<210> SEQ ID NO 14
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 14

Arg Thr Tyr Tyr Arg Ser Lys Trp Tyr Asn
1               5                   10

<210> SEQ ID NO 15
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 15

Ala Arg Gly Met Met Thr Tyr Tyr Tyr Gly Met Asp Val
1               5                   10

<210> SEQ ID NO 16
<211> LENGTH: 109
<212> TYPE: PRT
<213> ORGANISM: Artificial Sequence
<220> FEATURE:
<223> OTHER INFORMATION: SYNTHESIZED

<400> SEQUENCE: 16

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Thr Phe Gly Gly Gly Thr Lys Leu Glu Ile Lys Arg Ala
            100                 105

<210> SEQ ID NO 17
<211> LENGTH: 119
<212> TYPE: PRT
<213> ORGANISM: Artificial Sequence
<220> FEATURE:
<223> OTHER INFORMATION: SYNTHESIZED

<400> SEQUENCE: 17

Gln Val Gln Leu Val Gln Ser Gly Ala Glu Val Lys Arg Pro Gly Ala
1               5                   10                  15
```

Ser Val Gln Val Ser Cys Arg Ala Ser Gly Tyr Ser Ile Asn Thr Tyr
            20                  25                  30

Tyr Met Gln Trp Val Arg Gln Ala Pro Gly Ala Gly Leu Glu Trp Met
        35                  40                  45

Gly Val Ile Asn Pro Ser Gly Val Thr Ser Tyr Ala Gln Lys Phe Gln
 50                  55                  60

Gly Arg Val Thr Leu Thr Asn Asp Thr Ser Asn Thr Val Tyr Met
 65                  70                  75                  80

Gln Leu Asn Ser Leu Thr Ser Ala Asp Thr Ala Val Tyr Tyr Cys Ala
                85                  90                  95

Arg Trp Ala Leu Trp Gly Asp Phe Gly Met Asp Val Trp Gly Lys Gly
            100                 105                 110

Thr Leu Val Thr Val Ser Ser
        115

<210> SEQ ID NO 18
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 18

Glu Gly Ile Tyr His Trp
1               5

<210> SEQ ID NO 19
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 19

Gln Gln Tyr Ser Asn Tyr Pro Leu Thr
1               5

<210> SEQ ID NO 20
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 20

Gly Tyr Ser Ile Asn Thr Tyr Tyr
1               5

<210> SEQ ID NO 21
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 21

Ile Asn Pro Ser Gly Val Thr
1               5

<210> SEQ ID NO 22
<211> LENGTH: 13
<212> TYPE: PRT
<213> ORGANISM: Artificial Sequence
<220> FEATURE:

<223> OTHER INFORMATION: SYNTHESIZED

<400> SEQUENCE: 22

Ala Arg Trp Ala Leu Trp Gly Asp Phe Gly Met Asp Val
1               5                   10

<210> SEQ ID NO 23
<211> LENGTH: 821
<212> TYPE: PRT
<213> ORGANISM: Artificial Sequence
<220> FEATURE:
<223> OTHER INFORMATION: SYNTHESIZED

<400> SEQUENCE: 23

Met Gly Ile Gln Gly Gly Ser Val Leu Phe Gly Leu Leu Leu Val Leu
1               5                   10                  15

Ala Val Phe Cys His Ser Gly His Ser Leu Pro Pro Arg Thr Gln Val
                20                  25                  30

Gln Leu Val Gln Ser Gly Ala Glu Val Lys Arg Pro Gly Ala Ser Val
            35                  40                  45

Gln Val Ser Cys Arg Ala Ser Gly Tyr Ser Ile Asn Thr Tyr Tyr Met
        50                  55                  60

Gln Trp Val Arg Gln Ala Pro Gly Ala Gly Leu Glu Trp Met Gly Val
65                  70                  75                  80

Ile Asn Pro Ser Gly Val Thr Ser Tyr Ala Gln Lys Phe Gln Gly Arg
                85                  90                  95

Val Thr Leu Thr Asn Asp Thr Ser Thr Asn Thr Val Tyr Met Gln Leu
            100                 105                 110

Asn Ser Leu Thr Ser Ala Asp Thr Ala Val Tyr Tyr Cys Ala Arg Trp
        115                 120                 125

Ala Leu Trp Gly Asp Phe Gly Met Asp Val Trp Gly Lys Gly Thr Leu
    130                 135                 140

Val Thr Val Ser Ser Gly Gly Gly Gly Ser Gly Gly Gly Gly Ser Gly
145                 150                 155                 160

Gly Gly Gly Ser Asp Ile Gln Met Thr Gln Ser Pro Ser Thr Leu Ser
                165                 170                 175

Ala Ser Ile Gly Asp Arg Val Thr Ile Thr Cys Arg Ala Ser Glu Gly
            180                 185                 190

Ile Tyr His Trp Leu Ala Trp Tyr Gln Lys Pro Gly Lys Ala Pro Lys
        195                 200                 205

Leu Leu Ile Tyr Lys Ala Ser Ser Leu Ala Ser Gly Ala Pro Ser Arg
    210                 215                 220

Phe Ser Gly Ser Gly Ser Gly Thr Asp Phe Thr Leu Thr Ile Ser Ser
225                 230                 235                 240

Leu Gln Pro Asp Asp Phe Ala Thr Tyr Tyr Cys Gln Gln Tyr Ser Asn
                245                 250                 255

Tyr Pro Leu Thr Phe Gly Gly Gly Thr Lys Leu Glu Ile Lys Arg Ala
            260                 265                 270

Arg Thr Pro Pro Met Ile Leu Arg Thr Ser Glu Glu Thr Ile Ser Thr
        275                 280                 285

Val Gln Glu Lys Gln Gln Asn Ile Ser Pro Leu Val Arg Glu Arg Gly
    290                 295                 300

Pro Gln Arg Val Ala Ala His Ile Thr Gly Thr Arg Gly Arg Ser Asn
305                 310                 315                 320

Thr Leu Ser Ser Pro Asn Ser Lys Asn Glu Lys Ala Leu Gly Arg Lys
                325                 330                 335

```
Ile Asn Ser Trp Glu Ser Ser Arg Ser Gly His Ser Phe Leu Ser Asn
            340                 345                 350

Leu His Leu Arg Asn Gly Glu Leu Val Ile His Glu Lys Gly Phe Tyr
            355                 360                 365

Tyr Ile Tyr Ser Gln Thr Tyr Phe Arg Phe Gln Glu Glu Ile Lys Glu
    370                 375                 380

Asn Thr Lys Asn Asp Lys Gln Met Val Gln Tyr Ile Tyr Lys Tyr Thr
385                 390                 395                 400

Ser Tyr Pro Asp Pro Ile Leu Leu Met Lys Ser Ala Arg Asn Ser Cys
                405                 410                 415

Trp Ser Lys Asp Ala Glu Tyr Gly Leu Tyr Ser Ile Tyr Gln Gly Gly
            420                 425                 430

Ile Phe Glu Leu Lys Glu Asn Asp Arg Ile Phe Val Ser Val Thr Asn
            435                 440                 445

Glu His Leu Ile Asp Met Asp His Glu Ala Ser Phe Phe Gly Ala Phe
            450                 455                 460

Leu Val Gly Arg Ser Gln Asn Ile Ser Pro Leu Val Arg Glu Arg Gly
465                 470                 475                 480

Pro Gln Arg Val Ala Ala His Ile Thr Gly Thr Arg Gly Arg Ser Asn
                485                 490                 495

Thr Leu Ser Ser Pro Asn Ser Lys Asn Glu Lys Ala Leu Gly Arg Lys
            500                 505                 510

Ile Asn Ser Trp Glu Ser Ser Arg Ser Gly His Ser Phe Leu Ser Asn
            515                 520                 525

Leu His Leu Arg Asn Gly Glu Leu Val Ile His Glu Lys Gly Phe Tyr
            530                 535                 540

Tyr Ile Tyr Ser Gln Thr Tyr Phe Arg Phe Gln Glu Glu Ile Lys Glu
545                 550                 555                 560

Asn Thr Lys Asn Asp Lys Gln Met Val Gln Tyr Ile Tyr Lys Tyr Thr
                565                 570                 575

Ser Tyr Pro Asp Pro Ile Leu Leu Met Lys Ser Ala Arg Asn Ser Cys
            580                 585                 590

Trp Ser Lys Asp Ala Glu Tyr Gly Leu Tyr Ser Ile Tyr Gln Gly Gly
            595                 600                 605

Ile Phe Glu Leu Lys Glu Asn Asp Arg Ile Phe Val Ser Val Thr Asn
610                 615                 620

Glu His Leu Ile Asp Met Asp His Glu Ala Ser Phe Phe Gly Ala Phe
625                 630                 635                 640

Leu Val Gly Arg Ser Gln Asn Ile Ser Pro Leu Val Arg Glu Arg Gly
                645                 650                 655

Pro Gln Arg Val Ala Ala His Ile Thr Gly Thr Arg Gly Arg Ser Asn
            660                 665                 670

Thr Leu Ser Ser Pro Asn Ser Lys Asn Glu Lys Ala Leu Gly Arg Lys
            675                 680                 685

Ile Asn Ser Trp Glu Ser Ser Arg Ser Gly His Ser Phe Leu Ser Asn
            690                 695                 700

Leu His Leu Arg Asn Gly Glu Leu Val Ile His Glu Lys Gly Phe Tyr
705                 710                 715                 720

Tyr Ile Tyr Ser Gln Thr Tyr Phe Arg Phe Gln Glu Glu Ile Lys Glu
                725                 730                 735

Asn Thr Lys Asn Asp Lys Gln Met Val Gln Tyr Ile Tyr Lys Tyr Thr
            740                 745                 750
```

```
Ser Tyr Pro Asp Pro Ile Leu Leu Met Lys Ser Ala Arg Asn Ser Cys
        755                 760                 765

Trp Ser Lys Asp Ala Glu Tyr Gly Leu Tyr Ser Ile Tyr Gln Gly Gly
        770                 775                 780

Ile Phe Glu Leu Lys Glu Asn Asp Arg Ile Phe Val Ser Val Thr Asn
785                 790                 795                 800

Glu His Leu Ile Asp Met Asp His Glu Ala Ser Phe Phe Gly Ala Phe
                805                 810                 815

Leu Val Gly Arg Ser
        820

<210> SEQ ID NO 24
<211> LENGTH: 838
<212> TYPE: PRT
<213> ORGANISM: Artificial Sequence
<220> FEATURE:
<223> OTHER INFORMATION: SYNTHESIZED

<400> SEQUENCE: 24

Met Gly Ile Gln Gly Gly Ser Val Leu Phe Gly Leu Leu Leu Val Leu
1               5                   10                  15

Ala Val Phe Cys His Ser Gly His Ser Leu Pro Pro Arg Thr Gln Val
                20                  25                  30

Gln Leu Gln Gln Ser Gly Pro Gly Leu Val Thr Pro Ser Gln Thr Leu
            35                  40                  45

Ser Leu Thr Cys Ala Ile Ser Gly Asp Ser Val Ser Ser Asn Ser Ala
        50                  55                  60

Thr Trp Asn Trp Ile Arg Gln Ser Pro Ser Arg Gly Leu Glu Trp Leu
65                  70                  75                  80

Gly Arg Thr Tyr Tyr Arg Ser Lys Trp Tyr Asn Asp Tyr Ala Val Ser
                85                  90                  95

Val Lys Ser Arg Met Ser Ile Asn Pro Asp Thr Ser Lys Asn Gln Phe
            100                 105                 110

Ser Leu Gln Leu Asn Ser Val Thr Pro Glu Asp Thr Ala Val Tyr Tyr
        115                 120                 125

Cys Ala Arg Gly Met Met Thr Tyr Tyr Gly Met Asp Val Trp Gly
130                 135                 140

Gln Gly Thr Thr Val Thr Val Ser Ser Gly Ile Leu Gly Ser Gly Gly
145                 150                 155                 160

Gly Gly Ser Gly Gly Gly Gly Ser Gly Gly Gly Ser Gln Pro Val
                165                 170                 175

Leu Thr Gln Ser Ser Leu Ser Ala Ser Pro Gly Ala Ser Ala Ser
        180                 185                 190

Leu Thr Cys Thr Leu Arg Ser Gly Ile Asn Val Gly Pro Tyr Arg Ile
        195                 200                 205

Tyr Trp Tyr Gln Gln Lys Pro Gly Ser Pro Pro Gln Tyr Leu Leu Asn
        210                 215                 220

Tyr Lys Ser Asp Ser Asp Lys Gln Gln Gly Ser Gly Val Pro Ser Arg
225                 230                 235                 240

Phe Ser Gly Ser Lys Asp Ala Ser Ala Asn Ala Gly Val Leu Leu Ile
                245                 250                 255

Ser Gly Leu Arg Ser Glu Asp Glu Ala Asp Tyr Tyr Cys Met Ile Trp
            260                 265                 270

His Ser Ser Ala Ala Val Phe Gly Gly Gly Thr Gln Leu Thr Val Leu
        275                 280                 285
```

```
Ser Arg Thr Pro Pro Met Ile Leu Arg Thr Ser Glu Thr Ile Ser
    290                 295                 300

Thr Val Gln Glu Lys Gln Gln Asn Ile Ser Pro Leu Val Arg Glu Arg
305                 310                 315                 320

Gly Pro Gln Arg Val Ala Ala His Ile Thr Gly Thr Arg Gly Arg Ser
                325                 330                 335

Asn Thr Leu Ser Ser Pro Asn Ser Lys Asn Glu Lys Ala Leu Gly Arg
                340                 345                 350

Lys Ile Asn Ser Trp Glu Ser Ser Arg Ser Gly His Ser Phe Leu Ser
            355                 360                 365

Asn Leu His Leu Arg Asn Gly Glu Leu Val Ile His Glu Lys Gly Phe
370                 375                 380

Tyr Tyr Ile Tyr Ser Gln Thr Tyr Phe Arg Phe Gln Glu Glu Ile Lys
385                 390                 395                 400

Glu Asn Thr Lys Asn Asp Lys Gln Met Val Gln Tyr Ile Tyr Lys Tyr
                405                 410                 415

Thr Ser Tyr Pro Asp Pro Ile Leu Leu Met Lys Ser Ala Arg Asn Ser
                420                 425                 430

Cys Trp Ser Lys Asp Ala Glu Tyr Gly Leu Tyr Ser Ile Tyr Gln Gly
            435                 440                 445

Gly Ile Phe Glu Leu Lys Glu Asn Asp Arg Ile Phe Val Ser Val Thr
450                 455                 460

Asn Glu His Leu Ile Asp Met Asp His Glu Ala Ser Phe Phe Gly Ala
465                 470                 475                 480

Phe Leu Val Gly Arg Ser Gln Asn Ile Ser Pro Leu Val Arg Glu Arg
                485                 490                 495

Gly Pro Gln Arg Val Ala Ala His Ile Thr Gly Thr Arg Gly Arg Ser
                500                 505                 510

Asn Thr Leu Ser Ser Pro Asn Ser Lys Asn Glu Lys Ala Leu Gly Arg
                515                 520                 525

Lys Ile Asn Ser Trp Glu Ser Ser Arg Ser Gly His Ser Phe Leu Ser
            530                 535                 540

Asn Leu His Leu Arg Asn Gly Glu Leu Val Ile His Glu Lys Gly Phe
545                 550                 555                 560

Tyr Tyr Ile Tyr Ser Gln Thr Tyr Phe Arg Phe Gln Glu Glu Ile Lys
                565                 570                 575

Glu Asn Thr Lys Asn Asp Lys Gln Met Val Gln Tyr Ile Tyr Lys Tyr
                580                 585                 590

Thr Ser Tyr Pro Asp Pro Ile Leu Leu Met Lys Ser Ala Arg Asn Ser
                595                 600                 605

Cys Trp Ser Lys Asp Ala Glu Tyr Gly Leu Tyr Ser Ile Tyr Gln Gly
            610                 615                 620

Gly Ile Phe Glu Leu Lys Glu Asn Asp Arg Ile Phe Val Ser Val Thr
625                 630                 635                 640

Asn Glu His Leu Ile Asp Met Asp His Glu Ala Ser Phe Phe Gly Ala
                645                 650                 655

Phe Leu Val Gly Arg Ser Gln Asn Ile Ser Pro Leu Val Arg Glu Arg
                660                 665                 670

Gly Pro Gln Arg Val Ala Ala His Ile Thr Gly Thr Arg Gly Arg Ser
                675                 680                 685

Asn Thr Leu Ser Ser Pro Asn Ser Lys Asn Glu Lys Ala Leu Gly Arg
                690                 695                 700

Lys Ile Asn Ser Trp Glu Ser Ser Arg Ser Gly His Ser Phe Leu Ser
```

```
                705                 710                 715                 720
Asn Leu His Leu Arg Asn Gly Glu Leu Val Ile His Glu Lys Gly Phe
                    725                 730                 735
Tyr Tyr Ile Tyr Ser Gln Thr Tyr Phe Arg Phe Gln Glu Glu Ile Lys
                    740                 745                 750
Glu Asn Thr Lys Asn Asp Lys Gln Met Val Gln Tyr Ile Tyr Lys Tyr
                    755                 760                 765
Thr Ser Tyr Pro Asp Pro Ile Leu Leu Met Lys Ser Ala Arg Asn Ser
                    770                 775                 780
Cys Trp Ser Lys Asp Ala Glu Tyr Gly Leu Tyr Ser Ile Tyr Gln Gly
785                 790                 795                 800
Gly Ile Phe Glu Leu Lys Glu Asn Asp Arg Ile Phe Val Ser Val Thr
                    805                 810                 815
Asn Glu His Leu Ile Asp Met Asp His Glu Ala Ser Phe Phe Gly Ala
                    820                 825                 830
Phe Leu Val Gly Arg Ser
                    835

<210> SEQ ID NO 25
<211> LENGTH: 796
<212> TYPE: PRT
<213> ORGANISM: Artificial Sequence
<220> FEATURE:
<223> OTHER INFORMATION: SYNTHESIZED

<400> SEQUENCE: 25

Leu Pro Pro Arg Thr Gln Val Gln Leu Val Gln Ser Gly Ala Glu Val
1               5                   10                  15
Lys Arg Pro Gly Ala Ser Val Gln Val Ser Cys Arg Ala Ser Gly Tyr
                    20                  25                  30
Ser Ile Asn Thr Tyr Tyr Met Gln Trp Val Arg Gln Ala Pro Gly Ala
                35                  40                  45
Gly Leu Glu Trp Met Gly Val Ile Asn Pro Ser Gly Val Thr Ser Tyr
            50                  55                  60
Ala Gln Lys Phe Gln Gly Arg Val Thr Leu Thr Asn Asp Thr Ser Thr
65                  70                  75                  80
Asn Thr Val Tyr Met Gln Leu Asn Ser Leu Thr Ser Ala Asp Thr Ala
                85                  90                  95
Val Tyr Tyr Cys Ala Arg Trp Ala Leu Trp Gly Asp Phe Gly Met Asp
                    100                 105                 110
Val Trp Gly Lys Gly Thr Leu Val Thr Val Ser Ser Gly Gly Gly Gly
                115                 120                 125
Ser Gly Gly Gly Gly Ser Gly Gly Gly Gly Ser Asp Ile Gln Met Thr
            130                 135                 140
Gln Ser Pro Ser Thr Leu Ser Ala Ser Ile Gly Asp Arg Val Thr Ile
145                 150                 155                 160
Thr Cys Arg Ala Ser Glu Gly Ile Tyr His Trp Leu Ala Trp Tyr Gln
                    165                 170                 175
Lys Pro Gly Lys Ala Pro Lys Leu Leu Ile Tyr Lys Ala Ser Ser Leu
                    180                 185                 190
Ala Ser Gly Ala Pro Ser Arg Phe Ser Gly Ser Gly Ser Gly Thr Asp
                195                 200                 205
Phe Thr Leu Thr Ile Ser Ser Leu Gln Pro Asp Asp Phe Ala Thr Tyr
            210                 215                 220
Tyr Cys Gln Gln Tyr Ser Asn Tyr Pro Leu Thr Phe Gly Gly Gly Thr
```

-continued

```
                225                 230                 235                 240
Lys Leu Glu Ile Lys Arg Ala Arg Thr Pro Pro Met Ile Leu Arg Thr
                    245                 250                 255

Ser Glu Glu Thr Ile Ser Thr Val Gln Glu Lys Gln Gln Asn Ile Ser
                260                 265                 270

Pro Leu Val Arg Glu Arg Gly Pro Gln Arg Val Ala Ala His Ile Thr
                275                 280                 285

Gly Thr Arg Gly Arg Ser Asn Thr Leu Ser Ser Pro Asn Ser Lys Asn
            290                 295                 300

Glu Lys Ala Leu Gly Arg Lys Ile Asn Ser Trp Glu Ser Ser Arg Ser
305                 310                 315                 320

Gly His Ser Phe Leu Ser Asn Leu His Leu Arg Asn Gly Glu Leu Val
                    325                 330                 335

Ile His Glu Lys Gly Phe Tyr Tyr Ile Tyr Ser Gln Thr Tyr Phe Arg
                340                 345                 350

Phe Gln Glu Glu Ile Lys Glu Asn Thr Lys Asn Asp Lys Gln Met Val
                355                 360                 365

Gln Tyr Ile Tyr Lys Tyr Thr Ser Tyr Pro Asp Pro Ile Leu Leu Met
            370                 375                 380

Lys Ser Ala Arg Asn Ser Cys Trp Ser Lys Asp Ala Glu Tyr Gly Leu
385                 390                 395                 400

Tyr Ser Ile Tyr Gln Gly Gly Ile Phe Glu Leu Lys Glu Asn Asp Arg
                    405                 410                 415

Ile Phe Val Ser Val Thr Asn Glu His Leu Ile Asp Met Asp His Glu
                420                 425                 430

Ala Ser Phe Phe Gly Ala Phe Leu Val Gly Arg Ser Gln Asn Ile Ser
                435                 440                 445

Pro Leu Val Arg Glu Arg Gly Pro Gln Arg Val Ala Ala His Ile Thr
            450                 455                 460

Gly Thr Arg Gly Arg Ser Asn Thr Leu Ser Ser Pro Asn Ser Lys Asn
465                 470                 475                 480

Glu Lys Ala Leu Gly Arg Lys Ile Asn Ser Trp Glu Ser Ser Arg Ser
                    485                 490                 495

Gly His Ser Phe Leu Ser Asn Leu His Leu Arg Asn Gly Glu Leu Val
                500                 505                 510

Ile His Glu Lys Gly Phe Tyr Tyr Ile Tyr Ser Gln Thr Tyr Phe Arg
                515                 520                 525

Phe Gln Glu Glu Ile Lys Glu Asn Thr Lys Asn Asp Lys Gln Met Val
            530                 535                 540

Gln Tyr Ile Tyr Lys Tyr Thr Ser Tyr Pro Asp Pro Ile Leu Leu Met
545                 550                 555                 560

Lys Ser Ala Arg Asn Ser Cys Trp Ser Lys Asp Ala Glu Tyr Gly Leu
                    565                 570                 575

Tyr Ser Ile Tyr Gln Gly Gly Ile Phe Glu Leu Lys Glu Asn Asp Arg
                580                 585                 590

Ile Phe Val Ser Val Thr Asn Glu His Leu Ile Asp Met Asp His Glu
                595                 600                 605

Ala Ser Phe Phe Gly Ala Phe Leu Val Gly Arg Ser Gln Asn Ile Ser
            610                 615                 620

Pro Leu Val Arg Glu Arg Gly Pro Gln Arg Val Ala Ala His Ile Thr
625                 630                 635                 640

Gly Thr Arg Gly Arg Ser Asn Thr Leu Ser Ser Pro Asn Ser Lys Asn
                    645                 650                 655
```

```
Glu Lys Ala Leu Gly Arg Lys Ile Asn Ser Trp Glu Ser Ser Arg Ser
                660                 665                 670

Gly His Ser Phe Leu Ser Asn Leu His Leu Arg Asn Gly Glu Leu Val
            675                 680                 685

Ile His Glu Lys Gly Phe Tyr Tyr Ile Tyr Ser Gln Thr Tyr Phe Arg
        690                 695                 700

Phe Gln Glu Glu Ile Lys Glu Asn Thr Lys Asn Asp Lys Gln Met Val
705                 710                 715                 720

Gln Tyr Ile Tyr Lys Tyr Thr Ser Tyr Pro Asp Pro Ile Leu Leu Met
                725                 730                 735

Lys Ser Ala Arg Asn Ser Cys Trp Ser Lys Asp Ala Glu Tyr Gly Leu
            740                 745                 750

Tyr Ser Ile Tyr Gln Gly Gly Ile Phe Glu Leu Lys Glu Asn Asp Arg
        755                 760                 765

Ile Phe Val Ser Val Thr Asn Glu His Leu Ile Asp Met Asp His Glu
770                 775                 780

Ala Ser Phe Phe Gly Ala Phe Leu Val Gly Arg Ser
                790                 795
```

<210> SEQ ID NO 26
<211> LENGTH: 813
<212> TYPE: PRT
<213> ORGANISM: Artificial Sequence
<220> FEATURE:
<223> OTHER INFORMATION: SYNTHESIZED

<400> SEQUENCE: 26

```
Leu Pro Pro Arg Thr Gln Val Gln Leu Gln Gln Ser Gly Pro Gly Leu
1               5                   10                  15

Val Thr Pro Ser Gln Thr Leu Ser Leu Thr Cys Ala Ile Ser Gly Asp
            20                  25                  30

Ser Val Ser Ser Asn Ser Ala Thr Trp Asn Trp Ile Arg Gln Ser Pro
        35                  40                  45

Ser Arg Gly Leu Glu Trp Leu Gly Arg Thr Tyr Tyr Arg Ser Lys Trp
    50                  55                  60

Tyr Asn Asp Tyr Ala Val Ser Val Lys Ser Arg Met Ser Ile Asn Pro
65                  70                  75                  80

Asp Thr Ser Lys Asn Gln Phe Ser Leu Gln Leu Asn Ser Val Thr Pro
                85                  90                  95

Glu Asp Thr Ala Val Tyr Tyr Cys Ala Arg Gly Met Met Thr Tyr Tyr
            100                 105                 110

Tyr Gly Met Asp Val Trp Gly Gln Gly Thr Thr Val Thr Val Ser Ser
        115                 120                 125

Gly Ile Leu Gly Ser Gly Gly Gly Gly Ser Gly Gly Gly Gly Ser Gly
    130                 135                 140

Gly Gly Gly Ser Gln Pro Val Leu Thr Gln Ser Ser Ser Leu Ser Ala
145                 150                 155                 160

Ser Pro Gly Ala Ser Ala Ser Leu Thr Cys Thr Leu Arg Ser Gly Ile
                165                 170                 175

Asn Val Gly Pro Tyr Arg Ile Tyr Trp Tyr Gln Gln Lys Pro Gly Ser
            180                 185                 190

Pro Pro Gln Tyr Leu Leu Asn Tyr Lys Ser Asp Ser Asp Lys Gln Gln
        195                 200                 205

Gly Ser Gly Val Pro Ser Arg Phe Ser Gly Ser Lys Asp Ala Ser Ala
    210                 215                 220
```

```
Asn Ala Gly Val Leu Leu Ile Ser Gly Leu Arg Ser Glu Asp Glu Ala
225                 230                 235                 240

Asp Tyr Tyr Cys Met Ile Trp His Ser Ser Ala Ala Val Phe Gly Gly
            245                 250                 255

Gly Thr Gln Leu Thr Val Leu Ser Arg Thr Pro Pro Met Ile Leu Arg
                260                 265                 270

Thr Ser Glu Glu Thr Ile Ser Thr Val Gln Glu Lys Gln Gln Asn Ile
            275                 280                 285

Ser Pro Leu Val Arg Glu Arg Gly Pro Gln Arg Val Ala Ala His Ile
            290                 295                 300

Thr Gly Thr Arg Gly Arg Ser Asn Thr Leu Ser Ser Pro Asn Ser Lys
305                 310                 315                 320

Asn Glu Lys Ala Leu Gly Arg Lys Ile Asn Ser Trp Glu Ser Ser Arg
                325                 330                 335

Ser Gly His Ser Phe Leu Ser Asn Leu His Leu Arg Asn Gly Glu Leu
                340                 345                 350

Val Ile His Glu Lys Gly Phe Tyr Tyr Ile Tyr Ser Gln Thr Tyr Phe
            355                 360                 365

Arg Phe Gln Glu Glu Ile Lys Glu Asn Thr Lys Asn Asp Lys Gln Met
370                 375                 380

Val Gln Tyr Ile Tyr Lys Tyr Thr Ser Tyr Pro Asp Pro Ile Leu Leu
385                 390                 395                 400

Met Lys Ser Ala Arg Asn Ser Cys Trp Ser Lys Asp Ala Glu Tyr Gly
                405                 410                 415

Leu Tyr Ser Ile Tyr Gln Gly Gly Ile Phe Glu Leu Lys Glu Asn Asp
                420                 425                 430

Arg Ile Phe Val Ser Val Thr Asn Glu His Leu Ile Asp Met Asp His
            435                 440                 445

Glu Ala Ser Phe Phe Gly Ala Phe Leu Val Gly Arg Ser Gln Asn Ile
450                 455                 460

Ser Pro Leu Val Arg Glu Arg Gly Pro Gln Arg Val Ala Ala His Ile
465                 470                 475                 480

Thr Gly Thr Arg Gly Arg Ser Asn Thr Leu Ser Ser Pro Asn Ser Lys
                485                 490                 495

Asn Glu Lys Ala Leu Gly Arg Lys Ile Asn Ser Trp Glu Ser Ser Arg
            500                 505                 510

Ser Gly His Ser Phe Leu Ser Asn Leu His Leu Arg Asn Gly Glu Leu
            515                 520                 525

Val Ile His Glu Lys Gly Phe Tyr Tyr Ile Tyr Ser Gln Thr Tyr Phe
            530                 535                 540

Arg Phe Gln Glu Glu Ile Lys Glu Asn Thr Lys Asn Asp Lys Gln Met
545                 550                 555                 560

Val Gln Tyr Ile Tyr Lys Tyr Thr Ser Tyr Pro Asp Pro Ile Leu Leu
                565                 570                 575

Met Lys Ser Ala Arg Asn Ser Cys Trp Ser Lys Asp Ala Glu Tyr Gly
            580                 585                 590

Leu Tyr Ser Ile Tyr Gln Gly Gly Ile Phe Glu Leu Lys Glu Asn Asp
            595                 600                 605

Arg Ile Phe Val Ser Val Thr Asn Glu His Leu Ile Asp Met Asp His
            610                 615                 620

Glu Ala Ser Phe Phe Gly Ala Phe Leu Val Gly Arg Ser Gln Asn Ile
625                 630                 635                 640
```

-continued

```
Ser Pro Leu Val Arg Glu Arg Gly Pro Gln Arg Val Ala Ala His Ile
            645                 650                 655

Thr Gly Thr Arg Gly Arg Ser Asn Thr Leu Ser Ser Pro Asn Ser Lys
            660                 665                 670

Asn Glu Lys Ala Leu Gly Arg Lys Ile Asn Ser Trp Glu Ser Ser Arg
            675                 680                 685

Ser Gly His Ser Phe Leu Ser Asn Leu His Leu Arg Asn Gly Glu Leu
            690                 695                 700

Val Ile His Glu Lys Gly Phe Tyr Tyr Ile Tyr Ser Gln Thr Tyr Phe
705                 710                 715                 720

Arg Phe Gln Glu Glu Ile Lys Glu Asn Thr Lys Asn Asp Lys Gln Met
                725                 730                 735

Val Gln Tyr Ile Tyr Lys Tyr Thr Ser Tyr Pro Asp Pro Ile Leu Leu
                740                 745                 750

Met Lys Ser Ala Arg Asn Ser Cys Trp Ser Lys Asp Ala Glu Tyr Gly
            755                 760                 765

Leu Tyr Ser Ile Tyr Gln Gly Gly Ile Phe Glu Leu Lys Glu Asn Asp
            770                 775                 780

Arg Ile Phe Val Ser Val Thr Asn Glu His Leu Ile Asp Met Asp His
785                 790                 795                 800

Glu Ala Ser Phe Phe Gly Ala Phe Leu Val Gly Arg Ser
                805                 810
```